US010011627B2

(12) United States Patent
Zhong et al.

(10) Patent No.: US 10,011,627 B2
(45) Date of Patent: Jul. 3, 2018

(54) C-ARYL GLUCOSIDE DERIVATIVE, PREPARATION METHODS THEREOF, AND MEDICAL APPLICATIONS THEREOF

(71) Applicant: YOUNGENE THERAPEUTICS CO., LTD, (Shanghai) Pilot Free Trade Zone (CN)

(72) Inventors: Huijuan Zhong, Jiangsu (CN); Jianchun Liao, Jiangsu (CN); Hongping Yu, Jiangsu (CN); Yaochang Xu, Jiangsu (CN); Qing Li, Jiangsu (CN); Jianghua Chen, Jiangsu (CN); Peng Gao, Jiangsu (CN); Songliang Tan, Jiangsu (CN); Shaobao Wang, Jiangsu (CN)

(73) Assignee: YOUNGENE THERAPEUTICS CO., LTD, China (Shanghai) Pilot Free Trade Zone (CN)

( * ) Notice: Subject to any disclaimer, the term of this patent is extended or adjusted under 35 U.S.C. 154(b) by 169 days.

(21) Appl. No.: 14/917,792

(22) PCT Filed: Aug. 19, 2014

(86) PCT No.: PCT/CN2014/084717
§ 371 (c)(1),
(2) Date: Mar. 9, 2016

(87) PCT Pub. No.: WO2015/032272
PCT Pub. Date: Mar. 12, 2015

(65) Prior Publication Data
US 2016/0222047 A1  Aug. 4, 2016

(30) Foreign Application Priority Data
Sep. 9, 2013  (CN) .......................... 2013 1 0408357

(51) Int. Cl.
| C07H 7/06 | (2006.01) |
| C07H 9/04 | (2006.01) |
| C07D 409/10 | (2006.01) |
| C07D 409/14 | (2006.01) |
| A61K 31/00 | (2006.01) |
| C07H 7/04 | (2006.01) |
| A61K 31/7048 | (2006.01) |
| C07D 493/08 | (2006.01) |

(52) U.S. Cl.
CPC .............. *C07H 7/06* (2013.01); *A61K 31/00* (2013.01); *A61K 31/7048* (2013.01); *C07D 409/10* (2013.01); *C07D 409/14* (2013.01); *C07D 493/08* (2013.01); *C07H 7/04* (2013.01); *C07H 9/04* (2013.01)

(58) Field of Classification Search
None
See application file for complete search history.

(56) References Cited

U.S. PATENT DOCUMENTS

| 2003/0114390 A1 | 6/2003 | Washburn et al. |
| 2013/0130997 A1* | 5/2013 | Yang ........................ C07H 7/04 514/25 |

FOREIGN PATENT DOCUMENTS

| CN | 1407990 A | 4/2003 |
| EP | 2604612 A1 | 6/2013 |
| JP | 2003511458 A | 3/2003 |
| JP | 2004359630 A | 12/2004 |
| WO | 0127128 A1 | 4/2001 |
| WO | 2004013118 A1 | 2/2004 |
| WO | 2010074219 A1 | 7/2010 |
| WO | 2011048112 A1 | 4/2011 |
| WO | 2011048148 A2 | 4/2011 |
| WO | 2012019496 A1 | 2/2012 |
| WO | 2012140597 A1 | 10/2012 |

(Continued)

OTHER PUBLICATIONS

International Search Report dated Oct. 9, 2014 in International Application No. PCT/CN2014/084717.

(Continued)

*Primary Examiner* — Shaojia A Jiang
*Assistant Examiner* — Dale R Miller
(74) *Attorney, Agent, or Firm* — Panitch Schwarze Belisario & Nadel LLP

(57) ABSTRACT

C-aryl glucoside derivatives, preparation methods thereof, and medical applications thereof are described. Specifically, compounds represented by formula I, and, tautomers, enantiomers, diastereomers, racemates, and pharmaceutically acceptable salts of the compounds, preparation methods thereof, pharmaceutical compositions containing the compounds, and applications thereof are described. Compounds of formula (I) are useful as therapeutic agents, and particularly as sodium-dependent glucose contransporter protein (SGLT) inhibitors.

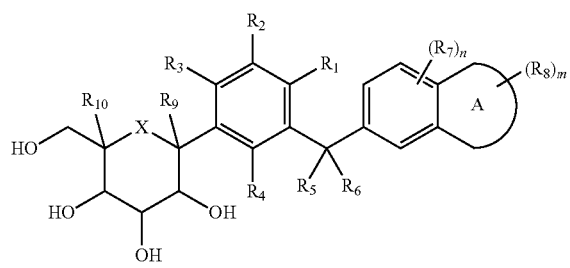

(I)

10 Claims, No Drawings

(56) References Cited

FOREIGN PATENT DOCUMENTS

WO      2012165914 A2    12/2012

OTHER PUBLICATIONS

Han et al., "Dapagliflozin, a Selective SGLT2 Inhibitor, Improves Glucose Homeostasis in Normal and Diabetic Rats," Diabetes, vol. 57, pp. 1723-1729 (Jun. 2008).
Office Action dated Apr. 1, 2017 in CN Application No. 2014-80048856.4.
Office Action dated Sep. 11, 2017 in CN Application No. 2014-80048856.4.
Office Action dated Sep. 22, 2017 in JP Application No. 2016-539403.
Supplemental European Search Report dated Apr. 6, 2017 in EP Application No. 14841970.8.
Supplemental European Search Report dated Jan. 4, 2017 in EP Application No. 14841970.8.

* cited by examiner

C-ARYL GLUCOSIDE DERIVATIVE, PREPARATION METHODS THEREOF, AND MEDICAL APPLICATIONS THEREOF

CROSS-REFERENCE TO RELATED APPLICATION

This application is a Section 371 of International Application No. PCT/CN2014/084717, filed Aug. 19, 2014, which was published in the Chinese language on Mar. 12, 2015 under International Publication No. WO 2015/032272 A1, and the disclosure of which is herein incorporated by reference.

FIELD OF THE INVENTION

The present invention relates to the field of drugs, and specifically relates to a C-aryl glucoside derivative, a preparation method thereof, and medical applications thereof.

BACKGROUND OF THE INVENTION

Diabetes is a metabolic disorder with recurrent or persistent hyperglycemia. Abnormal levels of blood glucose can lead to some serious and long-term complications, including cardiovascular disease, chronic renal failure, retinal damage, nerve damage, microvascular damage and obesity.

In the early stages of diabetes treatment, control of diet and exercise therapies are the preferred method for controlling blood glucose. When control of blood glucose is difficult to achieve with these methods, insulin or oral hypoglycemic drugs are needed for the treatment. There have been a variety of hypoglycemic drugs used currently in clinical treatment, including biguanide compounds, sulfonylurea compounds, insulin resistance improving agents, α-glucosidase inhibitors and so on. However, each of these drugs has various toxic effects and side effects, and is unable to meet the needs of long-term treatment. For example, biguanide compounds can cause lactic acidosis; sulfonylurea compounds can lead to hypoglycemia; insulin resistance improving agents can induce edema and heart failure, and α-glucosidase inhibitors can cause abdominal pain, distention, diarrhea and other symptoms. Because of the above situation, it is necessary to develop safer and more effective novel anti-diabetic drugs to meet the needs of diabetes treatment.

Studies have found that the regulation of cells regarding the process of glucose transport is mainly achieved by promoting the two protein family members of glucose transporter protein (GLUTs) (passive transport) and sodium-dependent glucose co-transporter protein (SGLTs) (active transport). SGLTs family members with glucose transporter function are mainly distributed in the intestine and the proximal tubule of the kidney and so on. Accordingly, it can be inferred that the SGLTs family members play a key role in glucose absorption in the intestine and glucose reuptake in the kidney, and they will become one of the ideal potential targets for treating diabetes.

In particular, SLGT-1 protein is one of the family members that is mainly distributed in the intestinal mucosal cells of the small intestine, with little expression in cardiac muscle and the kidney. It is mainly collaborative with GLUTs proteins to regulate glucose absorption in the intestine. Another one of the family members is SGLT-2, which is mainly responsible for regulating glucose reuptake in the kidneys due to its high level of expression in the kidneys, i.e., when glucose in urine passes through the glomerulus, it can actively attach to the epithelial cells of the renal tubule and be transported into the cells and recycled. During this process, SGLT-2 is responsible for 90% of reabsorption, and the remaining 10% of reabsorption is completed by SGLT-1. The theory of SGLT-2 as a major transport protein has been further confirmed in animal tests. SGLT-2 mRNA levels in rat renal cortex cells are reduced by specific SGLT-2 antisense oligonucleotides, thereby significantly inhibiting the reuptake of rat renal glucose. Based on these findings, it can be inferred that if a SGLTs (SGLT-1/SGLT-2) protein inhibitor is developed, through the regulation of its glucose transport function, it is possible to control intestinal absorption of glucose on the one hand, and on the other hand, to inhibit the reuptake of renal glucose and enhance discharge of glucose from the urine, thereby achieving a more systematic hypoglycemic effect. Therefore, a dual action inhibitor can be an ideal drug for treating diabetes.

Additionally, studies also found that SGLTs protein inhibitors can be useful for the treatment of diabetes-related complications, such as retinopathy, neuropathy, nephropathy, insulin resistance caused by glucose metabolism disorders, hyperinsulinemia, hyperlipidemia, obesity and so on. SGLTs protein inhibitors can be combined with the existing therapeutic agents, such as sulfonamides, thiazolidinediones, metformin, and insulin, etc. Without affecting efficacy, the dosage of drugs can be reduced to avoid or reduce the occurrence of adverse effects, thereby improving the adaptability of the patient to the treatment.

In summary, as a novel drug for treating diabetes, SGLTs protein inhibitor has good development prospects. Therefore, there is an urgent need to develop an effective compound that is safe and has good pharmacokinetic properties for the treatment of diabetes and related metabolic disorders.

SUMMARY OF THE INVENTION

The object of the present invention is to solve the above technical problems and provide a compound of formula (I), a tautomer, enantiomer, diastereomer, or racemate thereof, or a pharmaceutically acceptable salt thereof:

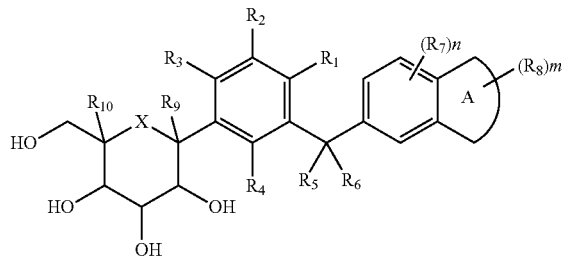

wherein:

ring A fused with the attached phenyl is selected from the group consisting of 5- to 7-membered cycloalkyl, 5- to 7-membered heterocyclyl, 5- to 7-membered aryl and 5- to 7-membered heteroaryl, wherein the 5- to 7-membered cycloalkyl, 5- to 7-membered heterocyclyl, 5- to 7-membered aryl and 5- to 7-membered heteroaryl are each independently and optionally substituted by one or more groups selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

wherein the $C_{1-8}$alkyl, $C_{3-8}$cycloalkyl, 3- to 8-membered heterocyclyl, $C_{5-10}$aryl and 5- to 10-membered heteroaryl are each independently and optionally substituted by one or more groups selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)OR$_{11}$, —NR$_{12}$R$_{13}$ and —C(O)NR$_{12}$;

$R_1$, $R_2$, $R_3$ and $R_4$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$;

wherein the $C_{1-8}$alkyl, $C_{3-8}$cycloalkyl, 3- to 8-membered heterocyclyl, $C_{5-10}$aryl and 5- to 10-membered heteroaryl are each independently and optionally substituted by one or more groups selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

or, $R_1$ and $R_2$ or $R_1$ and $R_3$ are taken together with the carbons of the attached phenyl to form a 5- to 7-membered cycloalkyl, 5- to 7-membered heterocyclyl, 5- to 7-membered aryl and 5- to 7-membered heteroaryl, wherein the 5- to 7-membered cycloalkyl, 5- to 7-membered heterocyclyl, 5- to 7-membered aryl and 5- to 7-membered heteroaryl are each independently and optionally substituted by one or more groups selected from the group consisting of halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$ cycloalkoxy, —S(O)$_p$R$_{11}$, —C(O)R$_{11}$, —C(O)OR$_{11}$, —NR$_{12}$R$_{13}$ and —C(O)NR$_{12}$;

$R_5$ and $R_6$ are each independently selected from the group consisting of hydrogen, deuterium, halogen, hydroxy, oxo, cyano, nitro, $C_{1-4}$alkyl, $C_{3-6}$cycloalkyl, $C_{1-4}$alkoxy, trihalomethyl and dihalomethyl;

$R_7$ and $R_8$ are each independently selected from the group consisting of hydrogen, deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

wherein the $C_{1-8}$alkyl, $C_{3-8}$cycloalkyl, 3- to 8-membered heterocyclyl, $C_{5-10}$aryl and 5- to 10-membered heteroaryl are each independently and optionally substituted by one or more groups selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

$R_9$ and $R_{10}$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$;

or, $R_9$ and $R_{10}$ are taken together with the carbons of the attached ring to form a 5- to 7-membered cycloalkyl, 5- to 7-membered heterocyclyl, 5- to 7-membered aryl and 5- to 7-membered heteroaryl, wherein the 5- to 7-membered cycloalkyl, 5- to 7-membered heterocyclyl, 5- to 7-membered aryl and 5- to 7-membered heteroaryl are each independently and optionally substituted by one or more groups selected from the group consisting of halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

$R_{11}$, $R_{12}$ and $R_{13}$ are selected from the group consisting of hydrogen and $C_{1-4}$alkyl;

X is selected from the group consisting of oxygen and sulphur;

m, n, and p are each 0, 1 or 2.

In a preferred embodiment, the present invention relates to a stereoisomer of the compound of formula (I), such as a compound of formula (I') or a pharmaceutically acceptable salt thereof:

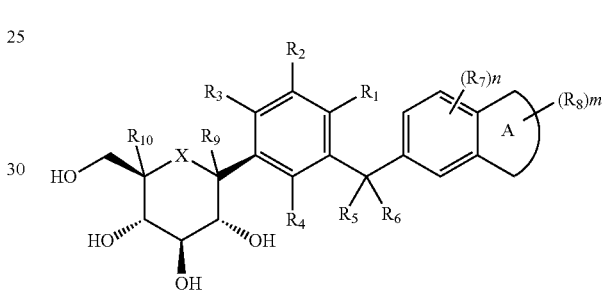

I' wherein ring A, $R_1$, $R_2$, $R_3$, $R_4$, $R_5$, $R_6$, $R_7$, $R_8$, $R_9$, $R_{10}$, $R_{11}$, $R_{12}$, $R_{13}$, X, m, n and p are as defined in formula (I).

In another preferred embodiment of the present invention, ring A fused with attached phenyl is a 5- to 7-membered cycloalkyl, 5- to 7-membered heterocyclyl, 5- to 7-membered aryl or 5- to 7-membered heteroaryl which is taken together with the attached phenyl to form a structure selected from the group consisting of:

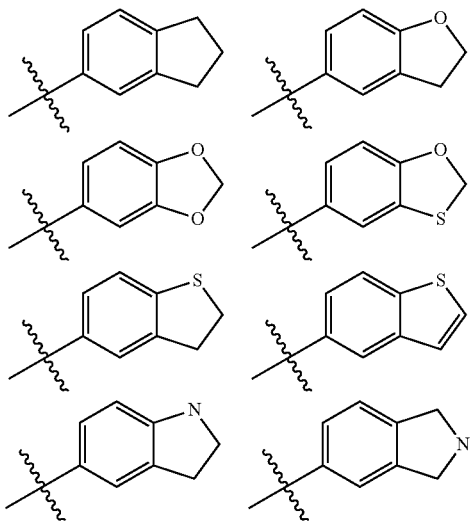

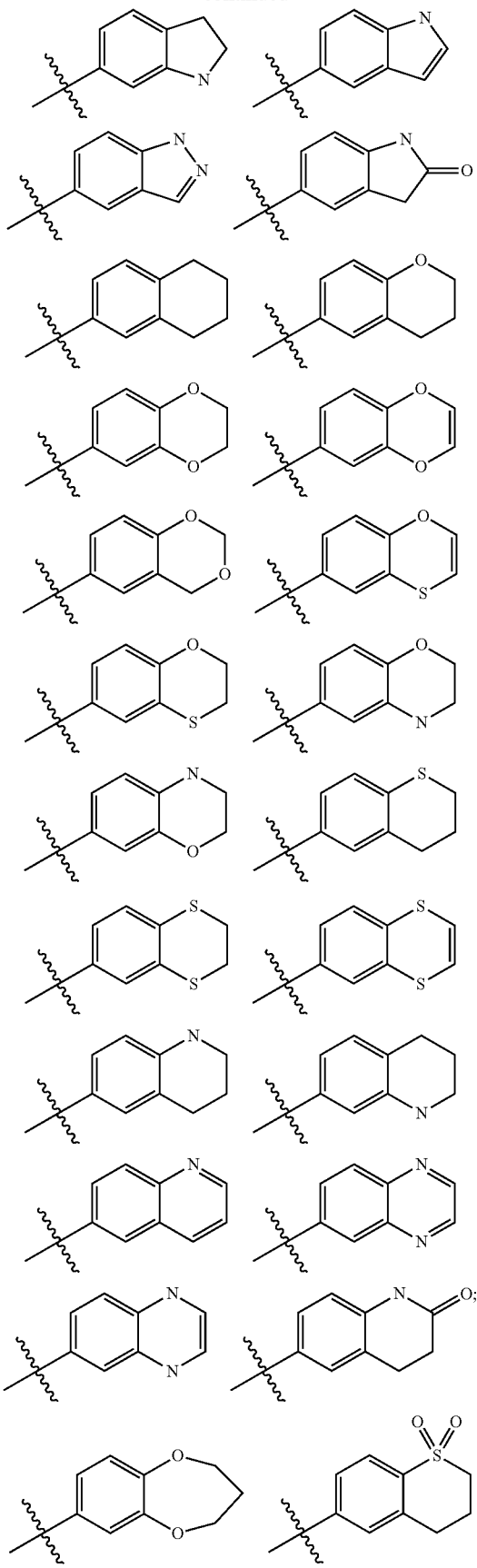
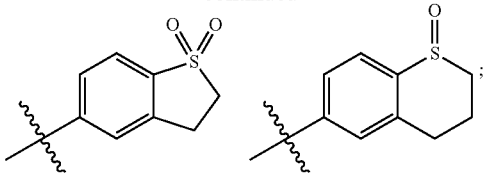
R₁ and R₂ are taken together with the carbons of the attached phenyl to form a 5- to 7-membered cycloalkyl, 5- to 7-membered heterocyclyl, 5- to 7-membered aryl or 5- to 7-membered heteroaryl which is taken together with the attached phenyl to form a structure selected from the group consisting of:
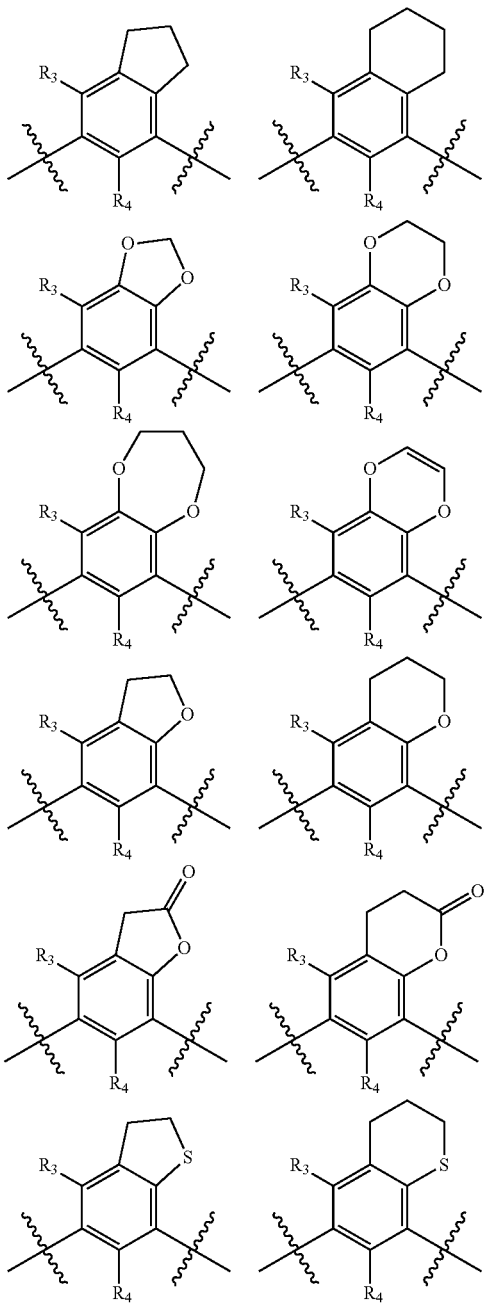

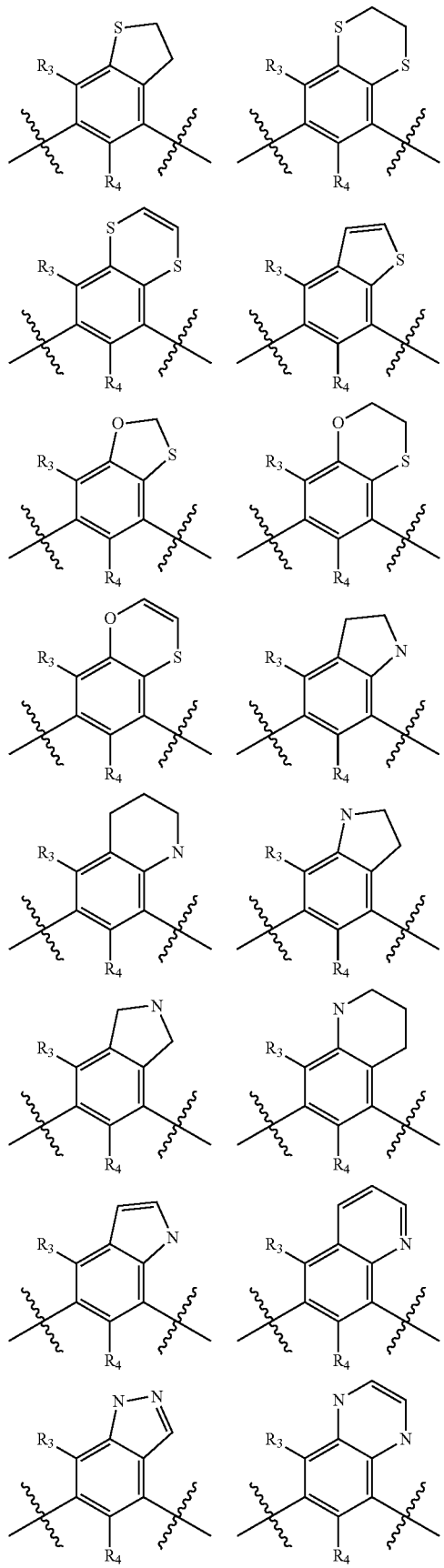
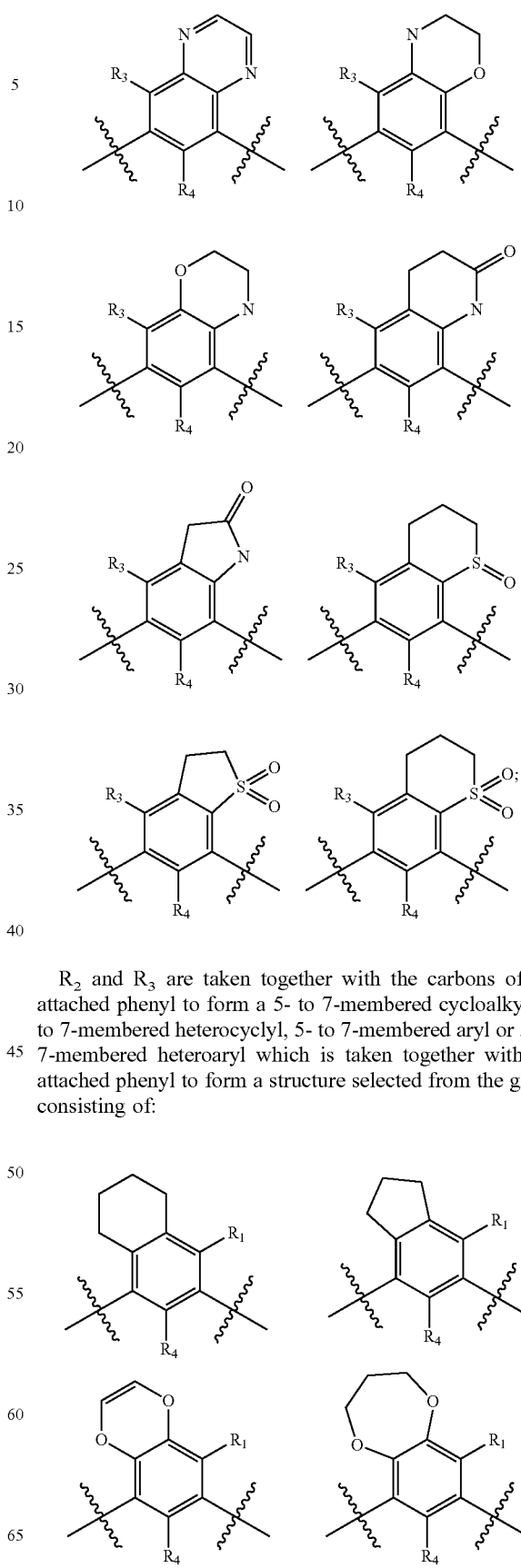
$R_2$ and $R_3$ are taken together with the carbons of the attached phenyl to form a 5- to 7-membered cycloalkyl, 5- to 7-membered heterocyclyl, 5- to 7-membered aryl or 5- to 7-membered heteroaryl which is taken together with the attached phenyl to form a structure selected from the group consisting of:

-continued
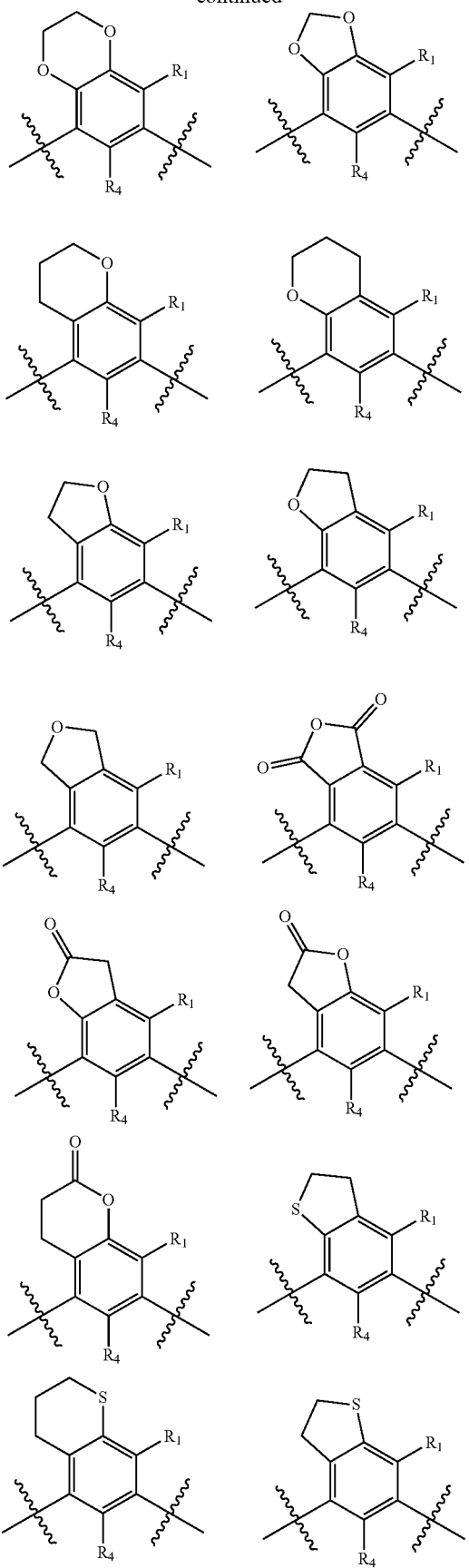
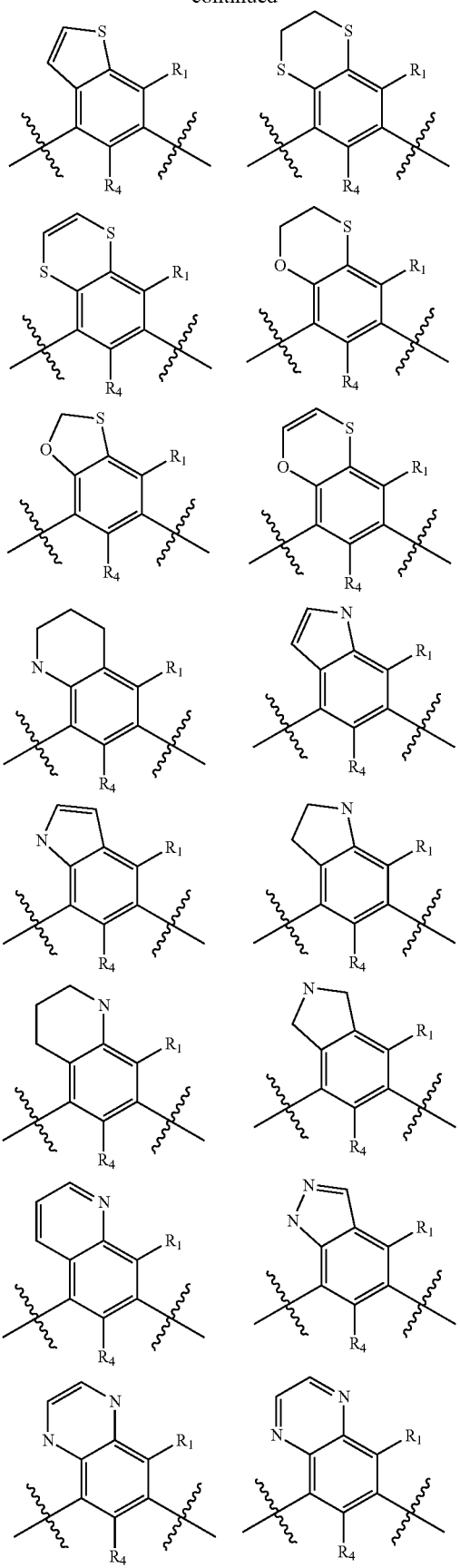

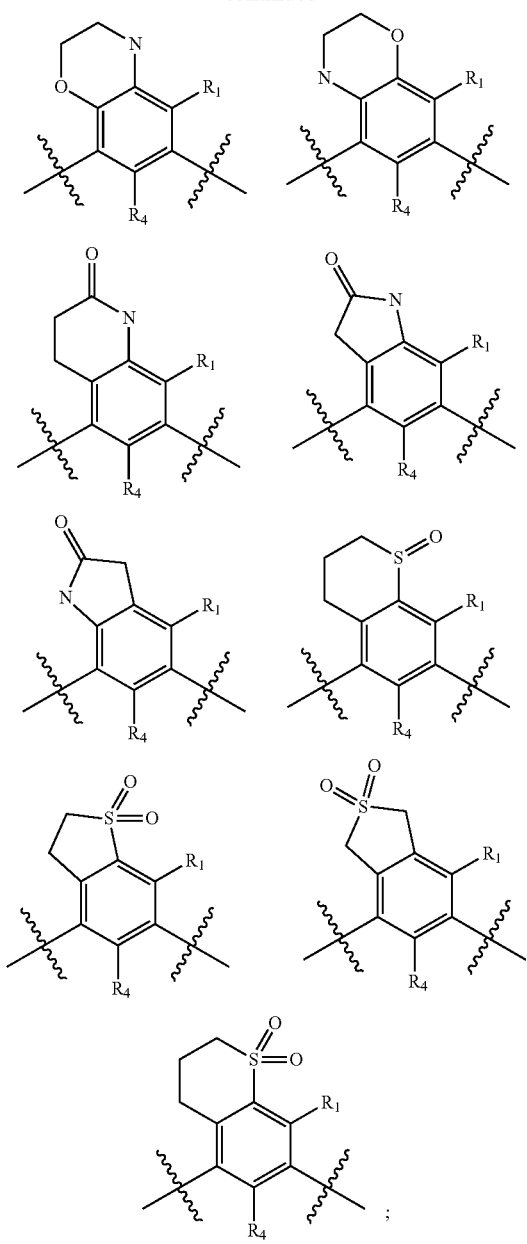
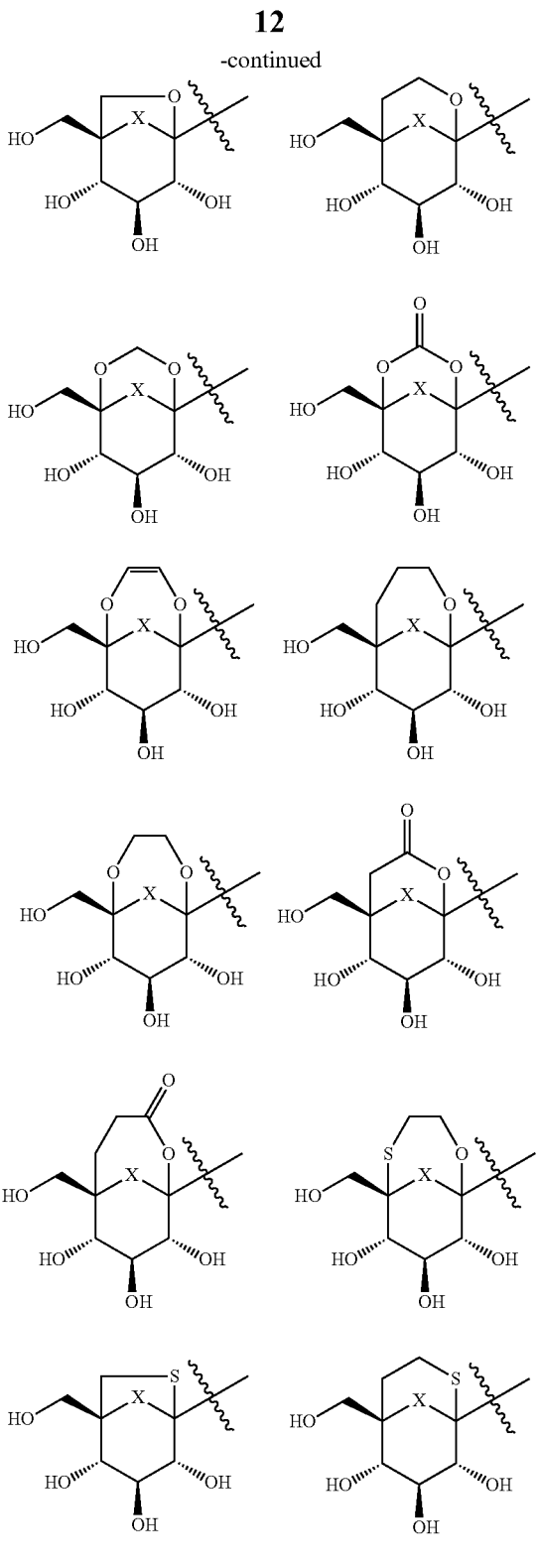
R₉ and R₁₀ are taken together with the carbons of the attached ring to form 5- to 7-membered cycloalkyl, 5- to 7-membered heterocyclyl, 5- to 7-membered aryl or 5- to 7-membered heteroaryl which is taken together with the attached ring to form a structure selected from the group consisting of:
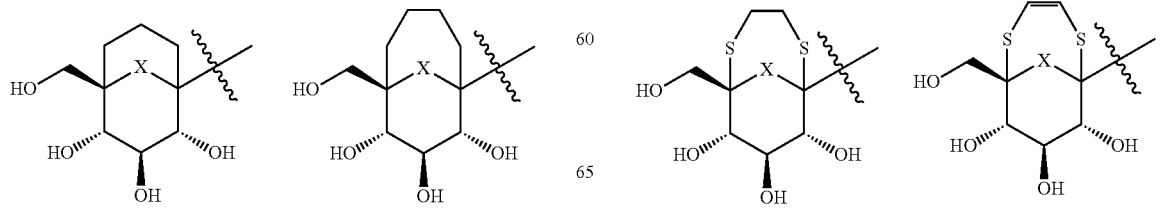

-continued

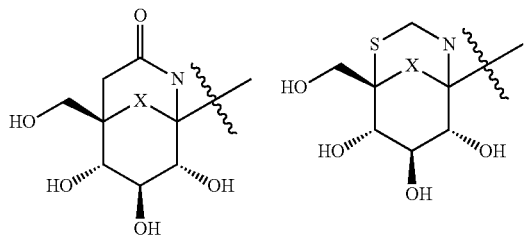

In a further preferred embodiment, the compound of formula (I) or the compound of formula (I') comprises a compound of formula (I-a) or a pharmaceutically acceptable salt thereof:

I-a

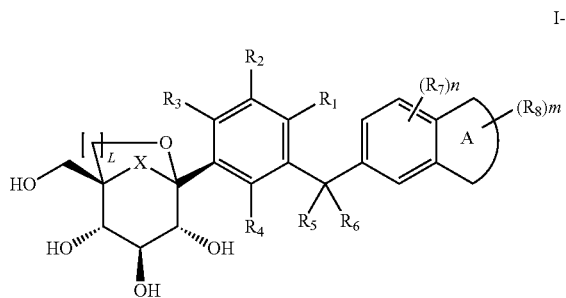

wherein:

$R_9$ and $R_{10}$ together represent —O—$(CH_2)_L$—, and $R_9$ and $R_{10}$ are taken together with the carbons of the attached ring to form a 5-7-membered heterocyclyl on the corresponding position of formula (I-a), wherein the 5- to 7-membered heterocyclyl is optionally substituted by one or more groups selected from the group consisting of halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

ring A, $R_1$, $R_2$, $R_3$, $R_4$, $R_5$, $R_6$, $R_7$, $R_8$, $R_{11}$, $R_{12}$, $R_{13}$, X, m, n and p are as defined in formula (I), L is 1, 2 or 3;

wherein, when X is oxygen and ring A fused with the attached phenyl is selected from the group consisting of a 5-membered heterocyclyl and 5-membered heteroaryl, the structure formed together with ring A and the attached phenyl does not include the following structures:

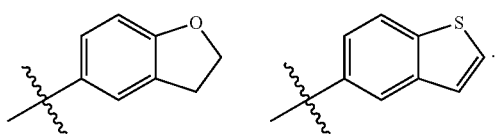 [SMILES: *c1ccc2c(c1)CCO2 ; *c1ccc2sccc2c1]

In a further preferred embodiment, the present invention relates to a compound of formula (I-a1) or a pharmaceutically acceptable salt thereof:

I-a1

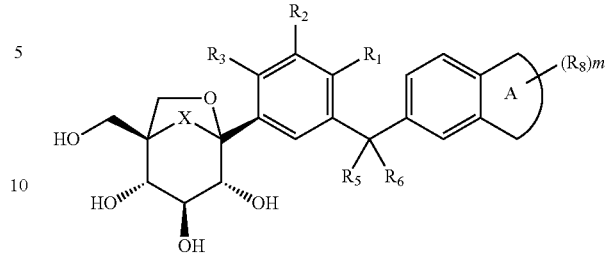

wherein:

ring A, $R_1$, $R_2$, $R_3$, $R_5$, $R_6$, $R_8$, $R_{11}$, $R_{12}$, $R_{13}$, X, m and p are as defined in formula (I);

provided that when X is oxygen and ring A fused with the attached phenyl is selected from the group consisting of a 5-membered heterocyclyl and 5-membered heteroaryl, the structure formed together with ring A and the attached phenyl does not include the following structures:

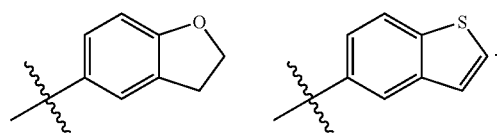 [SMILES: *c1ccc2c(c1)CCO2 ; *c1ccc2sccc2c1]

In a further preferred embodiment, the present invention relates to a compound of formula (I-a2) or a pharmaceutically acceptable salt thereof:

I-a2

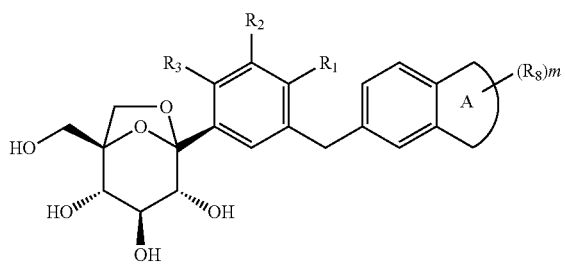

wherein:

ring A, $R_1$, $R_2$, $R_3$, $R_8$, $R_{11}$, $R_{12}$, $R_{13}$, m and p are as defined in formula (I);

provided that when X is oxygen and ring A fused with the attached phenyl is selected from the group consisting of a 5-membered heterocyclyl and 5-membered heteroaryl, the structure formed together with ring A and the attached phenyl does not include the following structures:

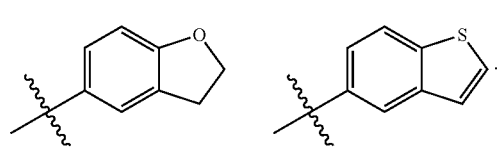 [SMILES: *c1ccc2c(c1)CCO2 ; *c1ccc2sccc2c1]

In a further preferred embodiment, the present invention relates to a compound of formula (I-a3) or a pharmaceutically acceptable salt thereof:

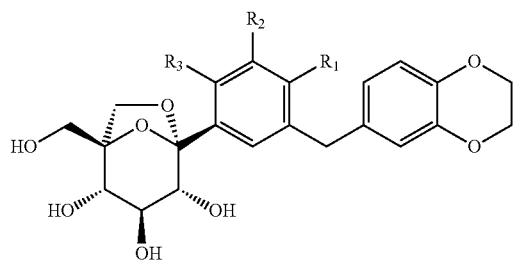

I-a3 wherein:

R$_1$, R$_2$ and R$_3$ are each independently selected from the group consisting of hydrogen, halogen, hydroxy, cyano, nitro, C$_{1-8}$alkyl, C$_{3-8}$cycloalkyl, C$_{1-8}$alkoxy, C$_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$; and R$_{11}$, R$_{12}$, R$_{13}$ and p are as defined in formula (I).

The compounds of formula (I, I', I-a, I-a1, I-a2 and I-a3) of the present invention include, but are not limited to, the following exemplary compounds:

| Example No. | Structure | Name |
|---|---|---|
| Example 1 | 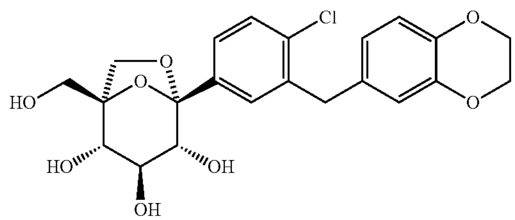 [SMILES: OC[C@@]12CO[C@@](c3ccc(Cl)c(Cc4ccc5c(c4)OCCO5)c3)(O1)[C@H](O)[C@@H](O)[C@@H]2O] | (1S,2S,3S,4R,5S)-5-(4-chloro-3-((2,3-dihydrobenzo[b][1,4]dioxin-6-yl)methyl)phenyl)-1-(hydroxymethyl)-6,8-dioxabicyclo[3.2.1]octane-2,3,4-triol |
| Example 2 | 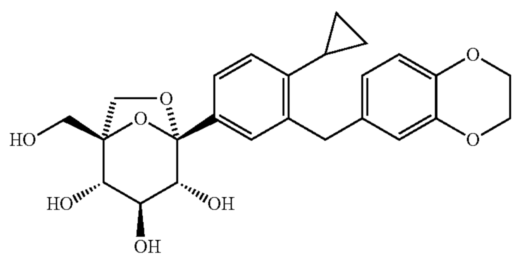 [SMILES: OC[C@@]12CO[C@@](c3ccc(C4CC4)c(Cc4ccc5c(c4)OCCO5)c3)(O1)[C@H](O)[C@@H](O)[C@@H]2O] | (1S,2S,3S,4R,5S)-5-(4-cyclopropyl-3-((2,3-dihydrobenzo[b][1,4]dioxin-6-yl)methyl)phenyl)-1-(hydroxymethyl)-6,8-dioxabicyclo[3.2.1]octane-2,3,4-triol |
| Example 7 | 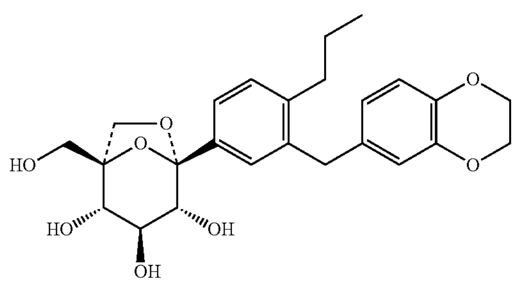 [SMILES: CCCc1ccc([C@]23OC[C@](CO)(O2)[C@@H](O)[C@H](O)[C@H]3O)cc1Cc1ccc2c(c1)OCCO2] | (1S,2S,3S,4R,5S)-5-(3-((2,3-dihydrobenzo[b][1,4]dioxin-6-yl)methyl)-4-propylphenyl)-1-(hydroxymethyl)-6,8-dioxabicyclo[3.2.1]octane-2,3,4-triol |
| Example 8 | 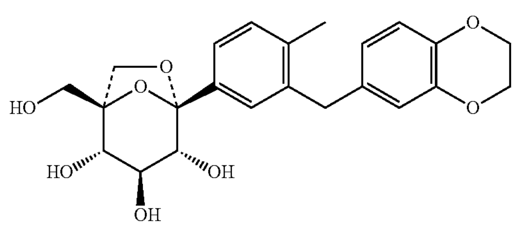 [SMILES: Cc1ccc([C@]23OC[C@](CO)(O2)[C@@H](O)[C@H](O)[C@H]3O)cc1Cc1ccc2c(c1)OCCO2] | (1S,2S,3S,4R,5S)-5-(3-((2,3-dihydrobenzo[b][1,4]dioxin-6-yl)methyl)-4-methylphenyl)-1-(hydroxymethyl)-6,8-dioxabicyclo[3.2.1]octane-2,3,4-triol |
| Example 9 | 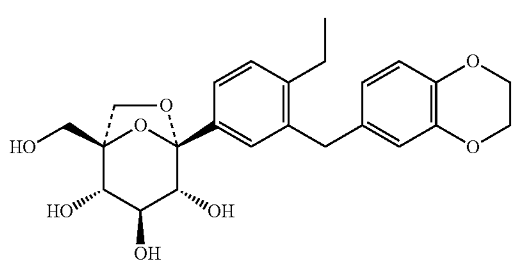 [SMILES: CCc1ccc([C@]23OC[C@](CO)(O2)[C@@H](O)[C@H](O)[C@H]3O)cc1Cc1ccc2c(c1)OCCO2] | (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol |

In a further preferred embodiment, the compound of formula (I) comprises a compound of formula (I-b) or a pharmaceutically acceptable salt thereof:

I-b

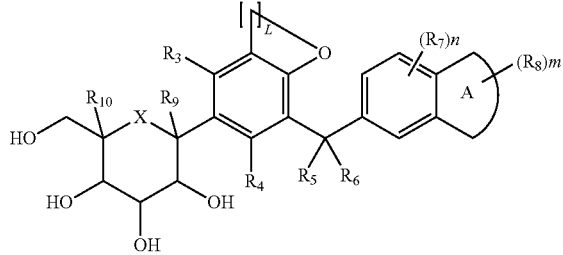

wherein:

$R_1$ and $R_2$ together represent —O—$(CH_2)_L$—, and $R_1$ and $R_2$ are taken together with the carbons of the attached phenyl to form a 5-7-membered heterocyclyl on the corresponding position of formula (I-b), wherein the 5- to 7-membered heterocyclyl is optionally substituted by one or more groups selected from the group consisting of halogen, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

$R_9$ and $R_{10}$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$;

ring A, $R_3$, $R_4$, $R_5$, $R_6$, $R_7$, $R_8$, $R_{11}$, $R_{12}$, $R_{13}$, X, m, n and p are as defined in formula (I), and L is 1, 2 or 3.

In a further preferred embodiment, the present invention relates to a compound of formula (I-b1) or a pharmaceutically acceptable salt thereof, I-b1

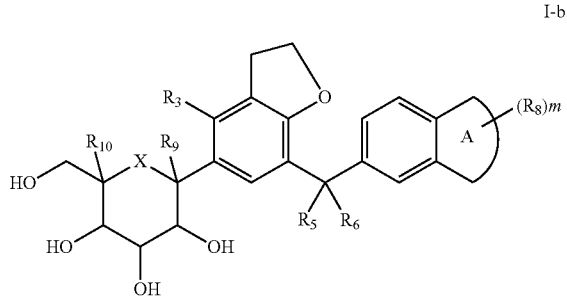

wherein:

$R_9$ and $R_{10}$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$; and ring A, $R_3$, $R_5$, $R_6$, $R_8$, $R_{11}$, $R_{12}$, $R_{13}$, X, m and p are as defined in formula (I).

In a further preferred embodiment, the present invention relates to a compound of formula (I-b2) or a pharmaceutically acceptable salt thereof:

I-b2

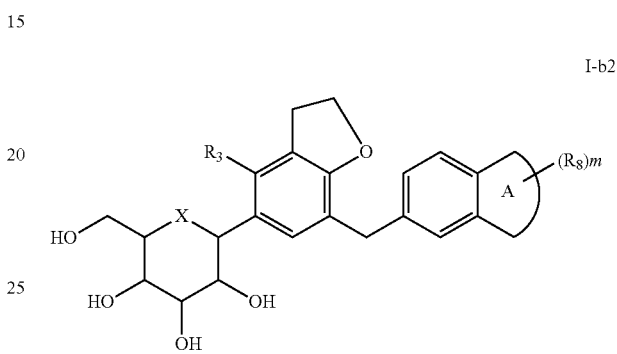

wherein ring A, $R_3$, $R_8$, $R_{11}$, $R_{12}$, $R_{13}$, X, m and p are as defined in formula (I).

In another preferred embodiment, the present invention relates to a compound of formula (I-b3) or a pharmaceutically acceptable salt thereof:

I-b3

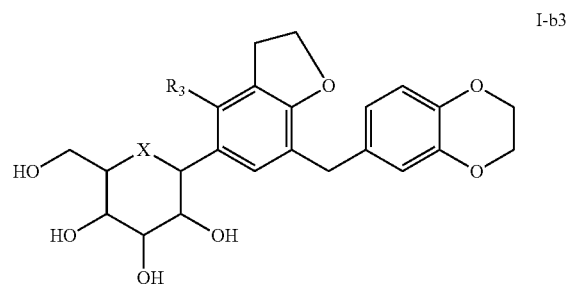

wherein $R_3$, $R_{11}$, $R_{12}$, $R_{13}$ and p are as defined in formula (I).

The compounds of formula (I, I', I-b, I-b1, I-b2 and I-b3) of the present invention include, but are not limited to, the following exemplary compounds:

| Example No | Structure | Name |
|---|---|---|
| Example 3 | 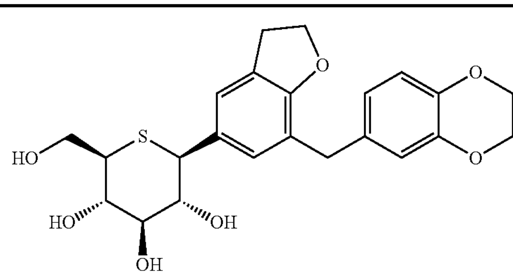 | (2S,3R,4R,5S,6R)-2-(7-((2,3-dihydrobenzo[b][1,4]dioxin-6-yl)methyl)-2,3-dihydrobenzofuran-5-yl)-6-(hydroxymethyl)tetrahydro-2H-thiopyran-3,4,5-triol |

In a further preferred embodiment, the compound of formula (I) comprises a compound of formula (I-c) or a pharmaceutically acceptable salt thereof:

I-c

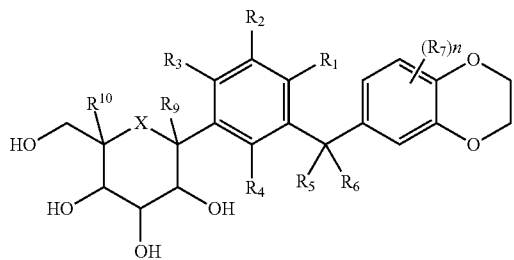

wherein:

$R_1$, $R_2$, $R_3$ and $R_4$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$;

wherein the $C_{1-8}$alkyl, $C_{3-8}$cycloalkyl, 3- to 8-membered heterocyclyl, $C_{5-10}$aryl and 5- to 10-membered heteroaryl are each independently and optionally substituted by one or more groups selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

$R_9$ and $R_{10}$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$; and $R_5$, $R_6$, $R_7$, $R_{11}$, $R_{12}$, $R_{13}$, X, n and p are as defined in formula (I).

In a further preferred embodiment, the present invention relates to a compound of formula (I-c1) or a pharmaceutically acceptable salt thereof:

I-c1

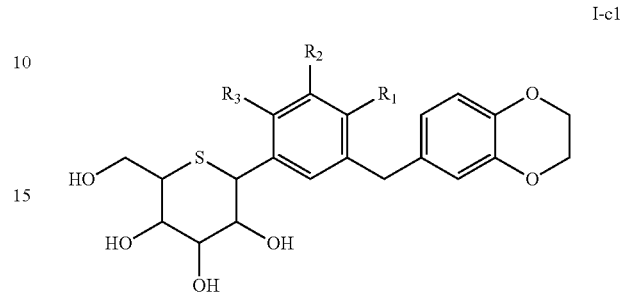

wherein:

$R_1$, $R_2$ and $R_3$ are each independently selected from the group consisting of hydrogen, halogen, hydroxy, cyano, nitro, $C_{1-8}$alkyl, $C_{2-8}$alkenyl, $C_{2-8}$alkynyl, $C_{3-8}$cycloalkyl, $C_{1-8}$alkoxy, $C_{3-8}$cycloalkoxy, 3- to 8-membered heterocyclyl, $C_{5-10}$aryl, 5- to 10-membered heteroaryl, —S(O)$_p$R$_{11}$, —C(O)R$_{11}$, —C(O)OR$_{11}$, —NR$_{12}$R$_{13}$ and —C(O)NR$_{12}$; and $R_{11}$, $R_{12}$, $R_{13}$ and p are as defined in formula (I).

In a further preferred embodiment, $R_1$, $R_2$ and $R_3$ are each independently selected from the group consisting of hydrogen, fluorine, bromine, iodine, hydroxy, cyano, nitro, $C_{1-8}$alkyl, $C_{3-8}$cycloalkyl, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$; and $R_{11}$, $R_{12}$, $R_{13}$ and p are as defined in formula (I).

The compounds of formula (I, I', I-c, and I-c1) of the present invention include, but are not limited to, the following exemplary compounds:

| Example No. | Structure | Name |
| --- | --- | --- |
| Example 4 | 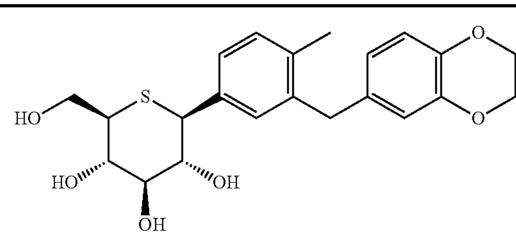 | (2S,3R,4R,5S,6R)-2-(3-((2,3-dihydrobenzo[b][1,4]dioxin-6-yl)methyl)-4-methylphenyl)-6-(hydroxymethyl)tetrahydro-2H-thiopyran-3,4,5-triol |
| Example 5 | 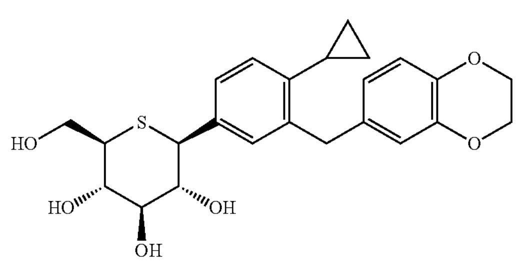 [SMILES: OC[C@H]1S[C@@H](c2ccc(C3CC3)c(Cc3ccc4c(c3)OCCO4)c2)[C@H](O)[C@@H](O)[C@@H]1O] | (2S,3R,4R,5S,6R)-2-(4-cyclopropyl-3-((2,3-dihydrobenzo[b][1,4]dioxin-6-yl)methyl)phenyl)-6-(hydroxymethyl)tetrahydro-2H-thiopyran-3,4,5-triol |

| Example No. | Structure | Name |
|---|---|---|
| Example 6 | 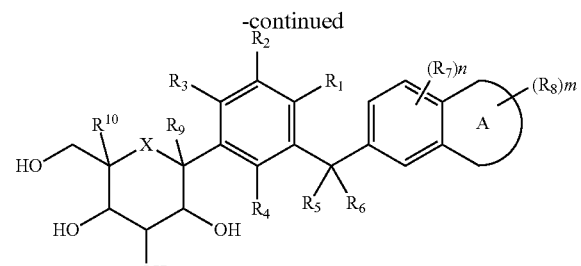 | (2S,3R,4R,5S,6R)-2-(5-((2,3-dihydrobenzo[b][1,4]dioxin-6-yl)methyl)-2-hydroxy-4-methylphenyl)-6-(hydroxymethyl)tetrahydro-2H-thiopyran-3,4,5-triol |

In another aspect, the present invention provides a process for preparing the compound of formula (I), comprising the following steps of: condensing a compound of formula (II) with a compound of formula (III) to provide a compound of formula (IV), converting the compound of formula (IV) according to the different definitions of $R_9$ and $R_{10}$ into a compound of formula (V), and then deprotecting the compound of formula (V) to provide the compound of formula (I) as follows:

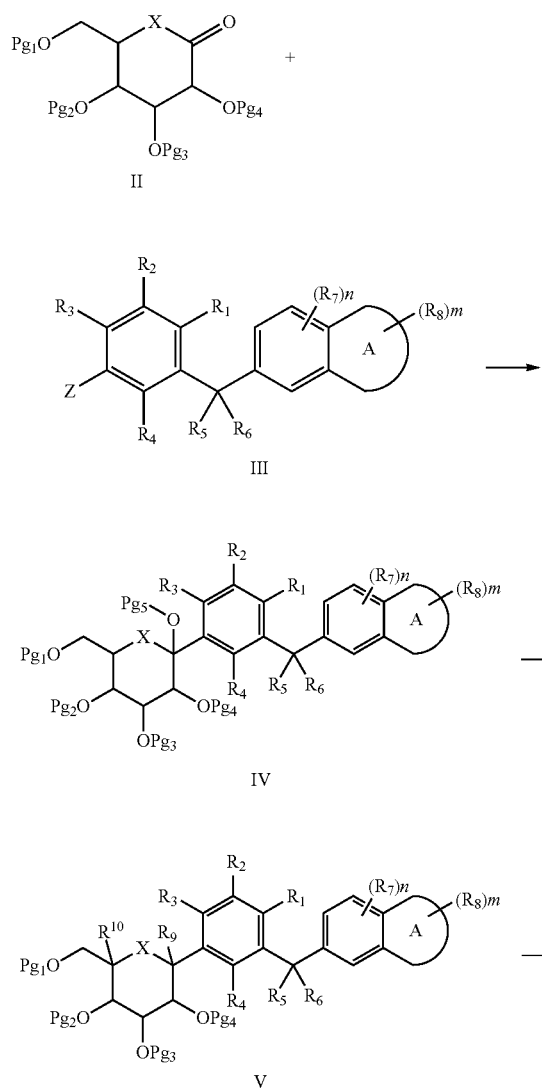

wherein:

Z is halogen; $Pg_1$, $Pg_2$, $Pg_3$ and $Pg_4$ are each independently a hydroxy protecting group which can be the same or different; $Pg_5$ is selected from the group consisting of hydrogen and a hydroxy protecting group; and ring A, $R_1$, $R_2$, $R_3$, $R_4$, $R_5$, $R_6$, $R_7$, $R_8$, $R_9$, $R_{10}$, $R_{11}$, $R_{12}$, $R_{13}$, X, m, n and p are as defined in formula (I).

In a further preferred embodiment, Z is selected from the group consisting of bromine and iodine; $Pg_1$, $Pg_2$, $Pg_3$ and $Pg_4$ are each independently selected from the group consisting of benzyl, trimethylsilyl and acetyl; and $Pg_5$ is selected from the group consisting of hydrogen and $C_{1-3}$alkyl.

In another aspect, the present invention provides a pharmaceutical composition comprising a therapeutically effective amount of a compound of formula (I), or a tautomer, enantiomer, diastereomer, or racemate thereof, or a pharmaceutically acceptable salt thereof, and a pharmaceutically acceptable carrier.

In another aspect, the present invention relates to use of a compound of formula (I), or a tautomer, enantiomer, diastereomer, or racemate thereof or a pharmaceutically acceptable salt thereof in the preparation of a Sodium-dependent glucose transporter (SGLT) protein inhibitor medicament.

Furthermore, the present invention relates to use of a compound of formula (I), or a tautomer, enantiomer, diastereomer, or racemate thereof, or a pharmaceutically acceptable salt thereof in the preparation of a SGLT-1 protein inhibitor medicament, SGLT-2 protein inhibitor medicament, or SGLT-1 and SGLT-2 dual protein inhibitor medicament.

In another aspect, the present invention relates to use of the compound I, or the tautomer, enantiomer, diastereomer, or racemate thereof, or the pharmaceutically acceptable salt thereof, or the pharmaceutical composition thereof in the preparation of a medicament for treating or delaying the development or the attack of a disease selected from the group consisting of diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications or atherosclerosis and hypertension.

In another aspect, the present invention relates to a method of treating diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetic complications or atherosclerosis or hypertension, comprising a step of administering to a patient in need thereof a therapeutically effective amount of the compound, or the tautomer, enantiomer, diastereomer, or racemate thereof, or the pharmaceutically acceptable salt thereof.

After extensive research, the inventors have surprisingly found that compounds of formula (I) showed very excellent inhibition effects of sodium-dependent glucose transporter proteins (SGLTs) and hypoglycemic effects. In addition to significant inhibition of SGLT-2, it also has good inhibition of SGLT-1, so it can be used to prepare an SGLT-2 and SGLT-1 dual protein inhibitor. It can also be independently used to prepare a SGLT-2 protein inhibitor or a SGLT-1 protein inhibitor.

DETAILED DESCRIPTION OF THE INVENTION

Unless otherwise stated, the terms used in the specification and claims have the following meanings.

"$C_{1-8}$alkyl" refers to a saturated aliphatic straight-chain and branched-chain hydrocarbon group including 1 to 8 carbon atoms, such as methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1, 1,2-methylpropyl, 1, 1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched chain isomers thereof, etc.

The alkyl can be substituted or unsubstituted. When substituted, the substituent can be substituted on any available connection points, and preferably the substituent group(s) is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$; wherein the $C_{1-8}$alkyl, $C_{3-8}$cycloalkyl, 3- to 8-membered heterocyclyl, $C_{5-10}$aryl and 5- to 10-membered heteroaryl are each optionally substituted with one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Cycloalkyl" refers to a saturated or partially unsaturated, monocyclic or polycyclic hydrocarbon substituent, "$C_{3-8}$cycloalkyl" refers to a cycloalkyl group including 3 to 8 carbon atoms. "5- to 7-membered cycloalkyl" refers to a cycloalkyl group including 5 to 7 carbon atoms, for example:

Non-limiting examples of monocyclic cycloalkyl groups include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc.

Polycyclic cycloalkyl group includes a cycloalkyl having a spiro ring, fused ring and bridged ring. "Spiro cycloalkyl" refers to a polycyclic group with rings connected through one common carbon atom (called a spiro atom), wherein these rings can contain one or more double bonds, but none of the rings has a completely conjugated π-electron system. According to the number of spiro atoms shared between the rings, the spiro cycloalkyl is divided into mono-spiro cycloalkyl, di-spiro cycloalkyl and poly-spiro cycloalkyl, Non-limiting examples of mono-spiro cycloalkyl include:

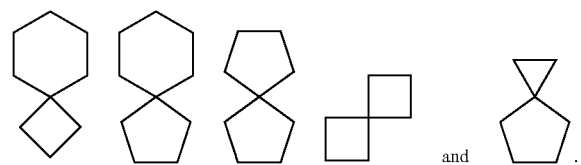

"Fused cycloalkyl" refers to an all-carbon polycyclic group in which each ring in the system shares an adjacent pair of carbon atoms with another ring, wherein one or more rings can contain one or more double bonds, but none of the rings has completely conjugated π-electron system. According to the number of rings, the fused cycloalkyl is divided into bicyclic, tricyclic, tetracyclic and polycyclic fused cycloalkyl. Non-limiting examples of fused cycloalkyl include:

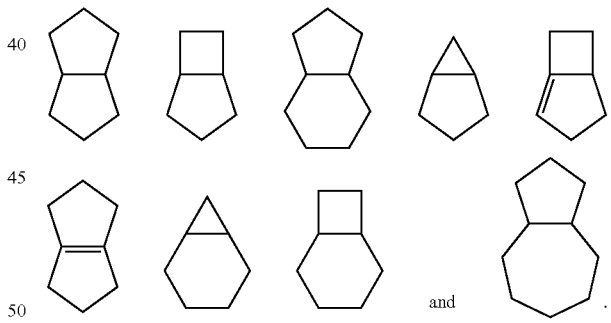

"Bridged cycloalkyl" refers to an all-carbon polycyclic group in which any two rings in the system share two disconnected carbon atoms, wherein the rings can contain one or more double bonds, but none of the rings has a completely conjugated n-electron system. According to the number of rings, bridged cycloalkyl is divided into bicyclic, tricyclic, tetracyclic and polycyclic bridged cycloalkyl. Non-limiting examples of fused cycloalkyl include:

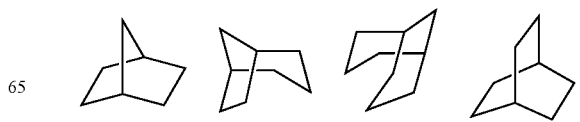

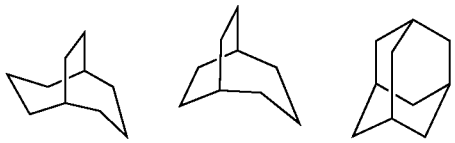

The cycloalkyl can be fused to the ring of aryl, heteroaryl or heterocyclyl, wherein the ring connected with the parent structure is cycloalkyl. Non-limiting examples include indanyl, tetrahydro-naphthyl, benzo cycloheptyl, etc.

The cycloalkyl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Heterocyclyl" refers to a saturated or partially unsaturated monocyclic or polycyclic hydrocarbon substituent, wherein one or more ring atoms are heteroatoms selected from the group consisting of nitrogen, oxygen and S(O)$_p$ (wherein p is an integer from 0 to 2), but the cyclic part does not include —O—O—, —O—S— or —S—S—, and the remaining ring atoms are carbon. "5- to 7-membered heterocyclyl" refers to a heterocyclyl group including 5 to 7 ring atoms, and "3- to 8-membered heterocyclyl" refers to a heterocyclyl group including 3 to 8 ring atoms.

Non-limiting examples of monocyclic heterocyclyl include pyrrolidinyl, piperidinyl, piperazinyl, morpholinyl, thiomorpholinyl, homopiperazinyl, etc.

Polycyclic heterocyclyl group includes a heterocyclyl having a spiro ring, fused ring and bridged ring. "Spiro heterocyclyl" refers to a polycyclic heterocyclyl group with rings connected through one common atom (called a spiro atom) shared between the rings, wherein one or more ring atoms are heteroatoms selected from the group consisting of nitrogen, oxygen and S(O)$_p$ (wherein p is an integer from 0 to 2), and the remaining ring atoms are carbon. These rings can contain one or more double bonds, but none of the rings has a completely conjugated π-electron system. According to the number of spiro atoms shared between the rings, the spiro heterocyclyl is divided into mono-Spiro heterocyclyl, di-spiro heterocyclyl and poly-spiro heterocyclyl. Non-limiting examples of spiro heterocyclyl include:

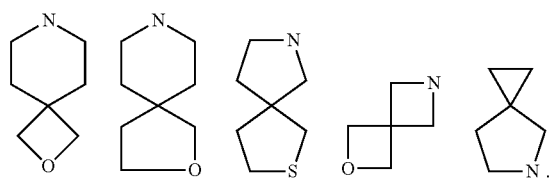

"Fused heterocyclyl" refers to a polycyclic heterocyclyl group in which each ring in the system shares an adjacent pair of atoms with another ring, wherein one or more rings can contain one or more double bonds, but none of the rings has a completely conjugated π-electron system, wherein one or more ring atoms are heteroatoms selected from the group consisting of nitrogen, oxygen and S(O)$_p$ (wherein p is an integer from 0 to 2), and the remaining ring atoms are carbon. According to the number of rings, fused heterocyclyl is divided into bicyclic, tricyclic, tetracyclic and polycyclic fused heterocyclyl. Non-limiting examples of fused heterocyclyl include:

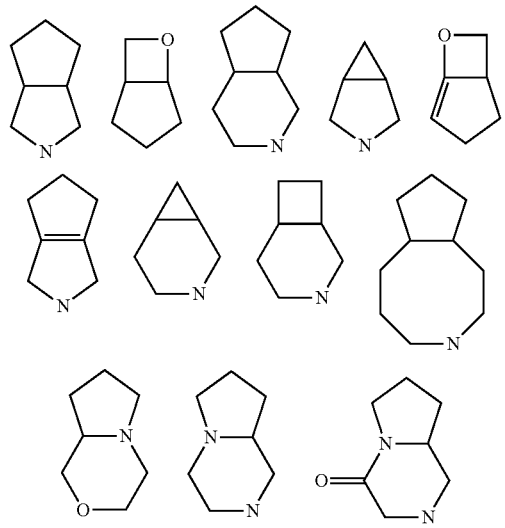

"Bridged heterocyclyl" refers to a polycyclic heterocyclyl group in which any two rings in the system share two disconnected carbon atoms. The rings can contain one or more double bonds, but none of the rings has a completely conjugated π-electron system, wherein one or more ring atoms are heteroatoms selected from the group consisting of nitrogen, oxygen and S(O)$_p$ (wherein p is an integer from 0 to 2), and the remaining ring atoms are carbon. According to the number of rings, bridged heterocyclyl is divided into bicyclic, tricyclic, tetracyclic and polycyclic bridged heterocyclyl. Non-limiting examples of bridged heterocyclyl include:

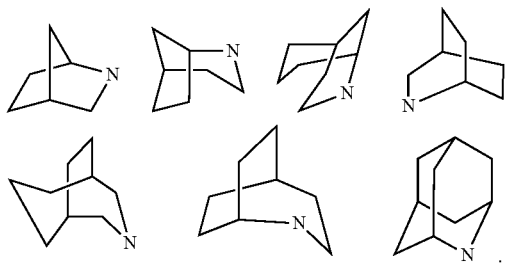

The heterocyclyl can be fused to the ring of aryl, heteroaryl or cycloalkyl, wherein the ring connected with the parent structure is heterocyclyl, and non-limiting examples include:

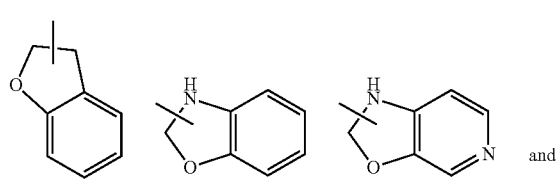

and

-continued

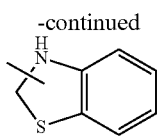

The heterocyclyl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Aryl" refers to an all-carbon monocyclic ring or polycyclic fused ring (namely, a ring in the system shares an adjacent pair of carbon atoms with another ring) with a conjugated π-electron system. "5- to 7-membered aryl" refers to an all-carbon aryl including 5 to 7 carbon atoms, such as phenyl and naphthyl. The aryl may be fused to the ring of a heteroaryl, heterocyclyl or cycloalkyl, wherein the ring connected with the parent structure is aryl, and non-limiting examples include:

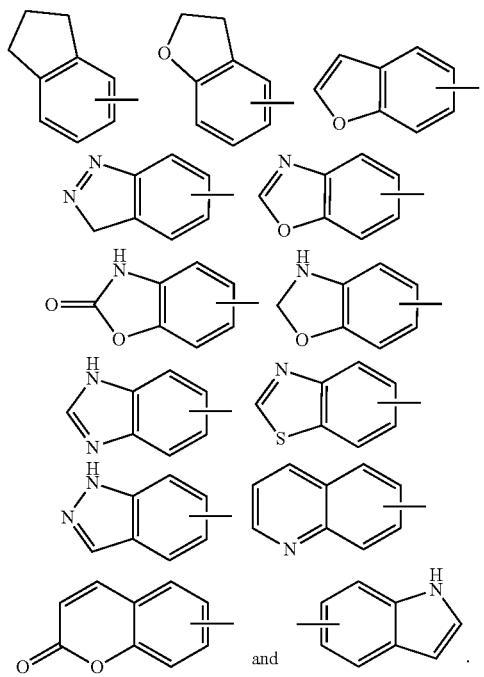

The aryl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Heteroaryl" refers to a heteroaromatic system comprising 1 to 4 heteroatoms, wherein the heteroatom comprises nitrogen, oxygen or S(O)$_p$ (wherein p is an integer from 0 to 2). "5- to 7-membered heteroaryl" refers to a heteroaromatic system including 5 to 7 ring atoms. "5- to 10-membered heteroaryl" refers to a heteroaromatic system including 5 to 10 ring atoms, such as furyl, thienyl, pyridyl, pyrrolyl, N-alkyl pyrrolyl, pyrimidinyl, pyrazinyl, imidazolyl, tetrazolyl, etc. The heteroaryl can be fused to the ring of aryl, heterocyclyl or cycloalkyl, wherein the ring connected with the parent structure is heteroaryl, and non-limiting examples include:

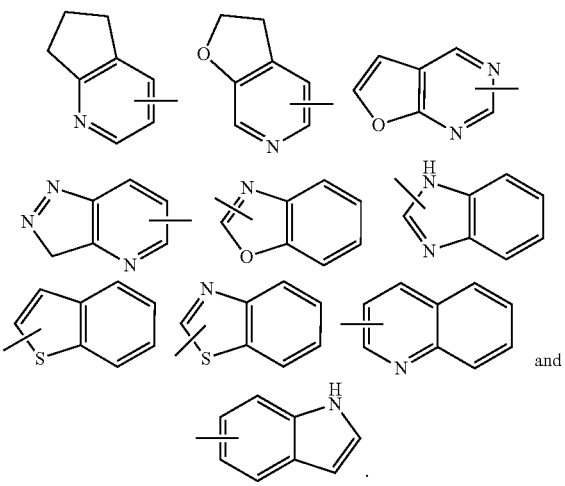

The heteroaryl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Alkenyl" refers to an alkyl group as defined above that has at least two carbon atoms and at least one carbon-carbon double bond, "$C_{2-8}$alkenyl" refers to a straight-chain or branched-chain alkenyl including 2 to 8 carbon atoms, for example, vinyl, 1-propenyl, 2-propenyl, 1-, 2- and 3-butenyl etc.

The alkenyl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Alkynyl" refers to an alkyl group as defined above that has at least two carbon atoms and at least one carbon-carbon triple bond, "$C_{2-8}$alkynyl" refers to a straight-chain or branched-chain alkynyl including 2 to 8 carbon atoms, for example, ethynyl, 1-propynyl, 2-propynyl, 1-, 2- and 3-butynyl, etc.

The alkynyl can be substituted or unsubstituted. When substituted, preferably the substituent is one or more groups independently selected from the group consisting of deuterium, halogen, hydroxy, cyano, nitro, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$.

"Alkoxy" refers to —O-(alkyl), wherein the alkyl group is as defined above, "$C_{1-8}$alkoxy" refers to an alkoxy including 1 to 8 carbon atoms, and non-limiting examples include methoxy, ethoxy, propoxy, butoxy, etc.

The alkoxy can be substituted or unsubstituted. When substituted, preferably the substituent is one or more groups independently selected from the group consisting of deuterium, halogen, hydroxy, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, $-S(O)_pR_{11}$, $-C(O)R_{11}$, $-C(O)OR_{11}$, $-NR_{12}R_{13}$ and $-C(O)NR_{12}$.

"Cycloalkoxy" refers to —O-(unsubstituted cycloalkyl), wherein the cycloalkyl group is as defined above. "$C_{3-8}$ cycloalkoxy" refers to a cycloalkoxy including 3 to 8 carbon atoms, and non-limiting examples include cyclopropyloxy, cyclobutyloxy, cyclopentyloxy, cyclohexyloxy, etc.

The cycloalkoxy can be substituted or unsubstituted. When substituted, preferably the substituent is one or more groups independently selected from the group consisting of deuterium, halogen, hydroxy, $C_{1-8}$alkyl, $C_{2-8}$alkenyl, $C_{2-8}$alkynyl, $C_{3-8}$cycloalkyl, 3- to 8-membered heterocyclyl, $C_{5-10}$aryl, 5- to 10-membered heteroaryl, $C_{1-6}$alkoxy, $C_{3-8}$cycloalkoxy, $-S(O)_pR_{11}$, $-C(O)R_{11}$, $-C(O)OR_{11}$, $-NR_{12}R_{13}$ and $-C(O)NR_{12}$.

"Deuterium" is heavy hydrogen. It is a stable form isotope of hydrogen, and the element symbol is "D" "Halogen" refers to fluorine, chlorine, bromine or iodine.

"$-S(O)_pR_{11}$" refers to $R_{11}$-substituted sulfur, sulfinyl, sulfonyl.

"$-C(O)R_{11}$" refers to $R_{11}$-substituted carbonyl.

"$-C(O)OR_{11}$" refers to $R_{11}$-substituted oxygen formyl.

"$-NR_{12}R_{13}$" refers to $R_{12}$-, $R_{13}$-substituted amino.

"$-C(O)NR_{12}$" refers to $R_{12}$-substituted carbamoyl.

"⌇" refers to a mixture with an uncertain ratio of α-, β-configuration product, preferably a mixture mainly comprising α-configuration, more preferably a mixture comprising more than 90% by weight of α-configuration. The "α-configuration" is also shown by "⌇", and the β-configuration is also shown by "⧹".

"Optional" or "optionally" means that the subsequently described event or circumstance can, but need not occur. Its meaning includes the instances in which the event or circumstance does or does not occur. For example, "heterocyclyl optionally substituted by alkyl" means that the alkyl can be, but need not be present. Its meaning includes the instances in which heterocyclyl is substituted or unsubstituted by alkyl.

"Substituted" refers to one or more hydrogen atoms of the group, preferably up to 5, more preferably 1 to 3 hydrogen atoms, each independently substituted by a corresponding number of substituent groups. It goes without saying that the substituents exist in their only possible positions. The person skilled in the art can determine whether the substitution is possible or impossible by experiment or theory without paying too much effort. For example, the combination of amino or hydroxy having free hydrogen and carbon atoms having an unsaturated bonds (e.g. olefinic) may be unstable.

A "pharmaceutical composition" refers to a mixture comprising one or more compounds described in the present invention or physiologically/pharmaceutically acceptable salts or prodrugs thereof and other components such as physiologically/pharmaceutically acceptable carriers and excipients. The purpose of a pharmaceutical composition is to facilitate administration of a compound to an organism, which will help absorption of the active ingredient, thereby realizing biological activity.

The following examples are used to further describe the present invention, but these examples are not intended to limit the scope of the present invention.

Structures of compounds were identified by nuclear magnetic resonance (NMR) and/or liquid chromatography-mass spectrometry (LC-MS).

NMR chemical shifts (δ) are given in $10^{-6}$ (ppm). NMR was determined by a Bruker AVANCE-400 instrument. The solvents were deuterated dimethyl sulfoxide (DMSO-$d_6$), deuterated chloroform (CDCl$_3$) and deuterated methanol (CD$_3$OD). The internal standard was tetramethylsilane (TMS).

LC-MS was determined by an Agilent 1200 Infinity Series mass spectrometer. High performance liquid chromatography (HPLC) was determined by an Agilent 1200DAD high pressure liquid chromatography spectrometer (Sunfire C18 150×4.6 mm chromatographic column).

For thin-layer silica gel chromatography (TLC), Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as a carrier.

The known starting materials used in the examples of the present invention can be synthesized by methods known in the art or are commercially available from ABCR GmbH & Co. KG, Acros Organics, Aldrich Chemical Company, Darui Chemical Company, etc.

Argon or nitrogen atmosphere means that a reaction flask is equipped with about a 1 L volume argon or nitrogen balloon.

Hydrogen atmosphere means that a reaction flask is equipped with about a 1 L hydrogen balloon.

For pressure hydrogenation reactions, Parr 3916EKX hydrogenated instrument and clear blue QL-500 hydrogen generator or HC2-SS hydrogenated instrument was used.

The hydrogenation reaction was usually conducted by vacuumizing, and filling with hydrogen, repeatedly for three times.

For the microwave reaction, an Anton Paar Monowave 300 microwave reactor was used.

Unless otherwise stated, the following reactions were under nitrogen or argon atmosphere.

Unless otherwise stated in the examples, the solution refers to an aqueous solution.

Unless otherwise stated in the examples, the reaction temperature was room temperature.

Room temperature is the optimum reaction temperature, and ranged from 20° C. to 30° C.

The reaction progress in the examples was monitored by thin layer chromatography (TLC), and the system of developing solvent included: dichloromethane and methanol system, n-hexane and ethyl acetate system. The volume ratio of solvent was adjusted according to the polarity of the compound.

The elution system for purification of the compounds by column chromatography and thin layer chromatography included: A: dichloromethane and methanol system, B: n-hexane and ethyl acetate system. The volume ratio of solvent was adjusted according to the polarity of the compound, and a small amount of ammonia and acetic acid can be added.

EXAMPLES

Example 1: (1S,2S,3S,4R,5S)-5-(4-chloro-3-((2,3-dihydrobenzo[b][1,4]dioxin-6-yl)methyl)phenyl)-1-(hydroxymethyl)-6,8-dioxabicyclo[3.2.1]octane-2,3,4-triol

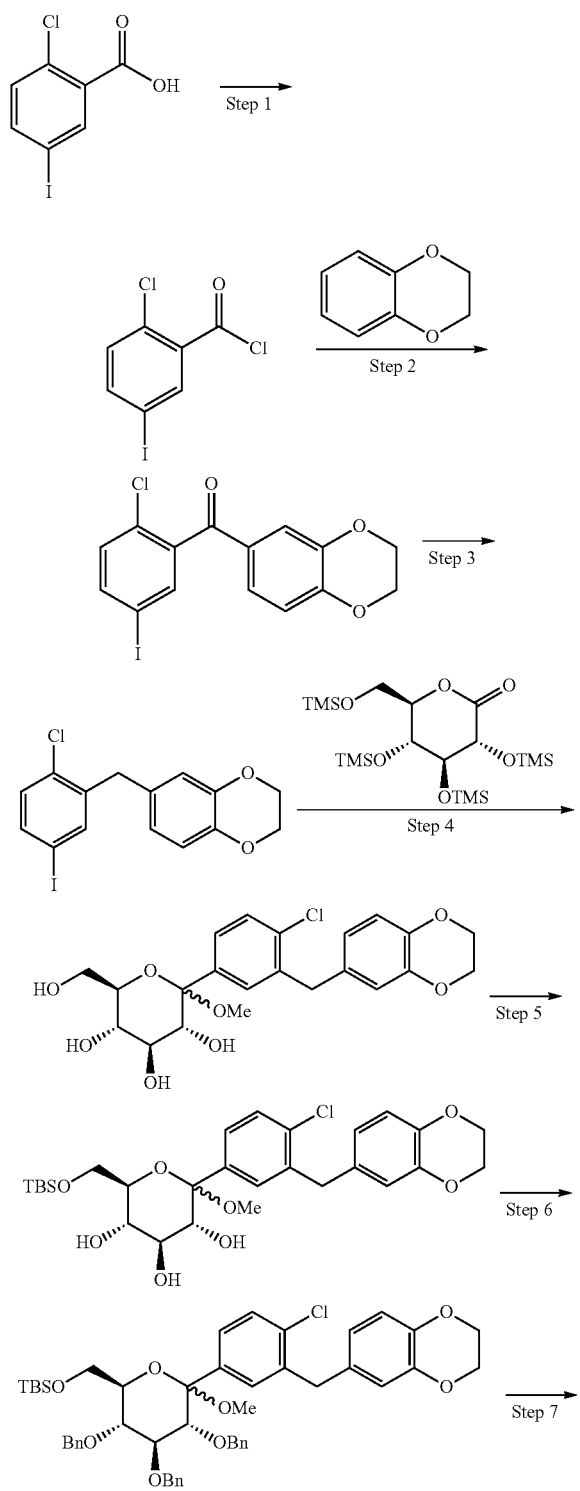

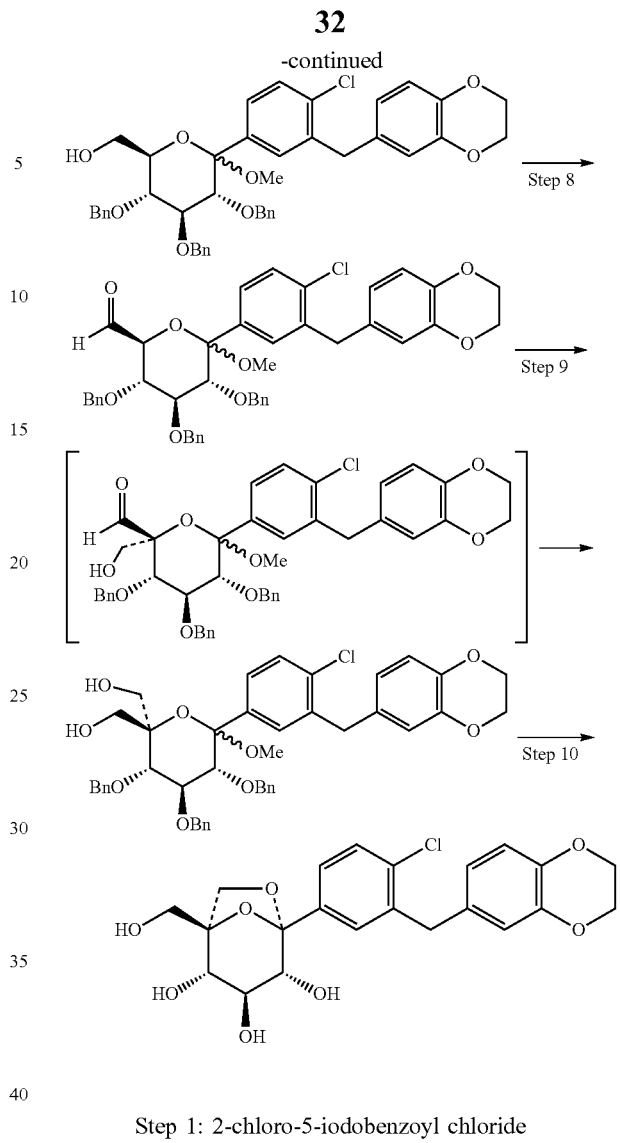

Step 1: 2-chloro-5-iodobenzoyl chloride

To a dried flask, 5-iodo-2-chlorobenzoic acid (20.0 g, 70.8 mmol) and dichloromethane (60 mL) were added. The reaction mixture was stirred, then oxalyl chloride (9.8 g, 77.9 mmol) and DMF (0.2 mL) were slowly added dropwise, and some bubbles were observed. The reaction mixture was stirred at room temperature for 7 hours. The solvent and excess oxalyl chloride were removed by rotary evaporation to give a gray solid, which was used directly in the next step without further purification.

Step 2: (2-chloro-5-iodophenyl)-(2,3-dihydrobenzo[b][1,4]dioxin-6-yl)methanone

The above crude 2-chloro-5-iodobenzoyl chloride was dissolved in dichloromethane (60 mL), then 2,3-dihydrobenzo[b][1,4]dioxine (9.9 g, 73 mmol) was added. The reaction mixture was stirred in an ice-water bath, and aluminium trichloride (10.1 g, 77 mmol) was added in batches. The reaction mixture was stirred for 16 hours at room temperature. The reaction solution was poured into ice water, the organic phase was separated, and the aqueous phase was extracted with EtOAc. The organic phases were combined, and washed successively with 1M hydrochloric acid, 1M KOH aqueous solution and saturated brine, then dried over anhydrous sodium sulfate and concentrated to give the title product (28 g, yield of two steps: 98.7%).

$^1$H NMR (400 MHz, CDCl$_3$) δ 7.72 (dd, J=8.4, 1.6 Hz, 1H), 7.83 (d, J=1.6 Hz, 1H), 7.35 (s, 1H), 7.32 (dd, J=8.4, 1.6 Hz, 1H), 7.16 (d, J=8.4 Hz, 1H), 6.92 (d, J=8.4 Hz, 1H), 4.31 (m, 4H).

Step 3: 6-(2-chloro-5-iodobenzyl)-2,3-dihydrobenzo[b][1,4]dioxine (2-chloro-5-iodophenyl)-(2,3-dihydrobenzo[b][1,4]dioxin-6-yl)methanone (28 g, 69.9 mmol) was dissolved in a mixed solvent of dichloromethane (30 mL) and acetonitrile (100 mL), then triethylsilane (45 mL, 282 mmol) was added. The reaction mixture was stirred in an ice-water bath, and BF$_3$.Et$_2$O (18 mL, 143 mmol) was added dropwise under N$_2$. The reaction mixture was heated to 50° C. for 16 hours, 4M KOH aqueous solution was added after it was cooled. The organic phase was separated, and the aqueous phase was extracted with EtOAc. The organic phases were combined and washed successively with 2M KOH solution and saturated brine, and then dried over anhydrous sodium sulfate and concentrated. The resulting residue was purified by column chromatography to give the product (26.2 g, yield: 97%).

$^1$H NMR (400 MHz, CDCl$_3$) δ 7.46 (m, 2H), 7.08 (d, J=8.4 Hz, 1H), 6.80 (d, J=8.4 Hz, 1H), 6.65 (m, 2H), 4.24 (s, 4H), 3.92 (s, 2H)

Step 4: (3R,4S,5S,6R)-2-(4-chloro-3-((2,3-dihydrobenzo[b][1,4]dioxin-6-yl)meth yl)phenyl)-6-(hydroxymethyl)-2-methoxytetrahydro-2H-pyran-3,4,5-triol 6-(2-chloro-5-iodobenzyl)-2,3-dihydrobenzo[b][1,4]dioxine (5.0 g, 12.95 mmol) was dissolved in a mixed solvent of THF (20 mL) and toluene (20 mL). The reaction mixture was cooled to −78° C., then a solution of n-BuLi in n-hexane (1.6M, 12.5 mL, 20 mmol) was added. The reaction mixture was stirred at this temperature for 40 minutes. A solution of (3R,4S,5R,6R)-3,4,5-tris(trimethylsilyloxy)-6-trimethylsilyloxymethyl-tetrahydropyran-2-one (6.5 g, 14.25 mmol) in toluene (15 mL) was added dropwise to the above system. The reaction mixture was stirred at −78° C. for 2 hours, then a solution of MsOH (3.0 g, 31.2 mmol) in methanol (6 mL) was added. The reaction mixture was stirred at room temperature overnight.

Saturated sodium bicarbonate aqueous solution was added, the reaction mixture was extracted with EtOAc, the organic phase was washed twice with saturated brine, and then dried over anhydrous sodium sulfate and concentrated. The resulting residue was purified by column chromatography to give the title product (2.4 g, yield: 41%).

$^1$H NMR (400 MHz, MeOD) δ 7.37 (s, 1H), 7.22 (m, 2H), 6.70 (d, J=8.0 Hz, 1H), 6.60 (m, 2H), 4.06 (s, 4H), 3.90 (m, 5H), 3.54 (m, 2H), 3.18 (d, J=8.0 Hz, 1H), 2.89 (s, 3H).

Step 5: (3R,4S,5S,6R)-6-(((tert-butyldimethylsilyl)oxy)methyl)-2-(4-chloro-3-((2,3-dihydrobenzo[b][1,4]dioxin-6-yl)methyl)phenyl)-2-methoxytetrahydro-2H-pyran-3,4,5-triol (3R,4S,5S,6R)-2-(4-chloro-3-((2,3-dihydrobenzo[b][1,4]dioxin-6-yl)methyl)phenyl)-6-(hydroxymethyl)-2-methoxytetrahydro-2H-pyran-3,4,5-triol (2.3 g, 5.1 mmol) was dissolved in dichloromethane (20 mL), then DMAP (0.061 g, 0.51 mmol) and imidazole (1.05 g, 15.5 mmol) were added, and then TBSCl (1.2 g, 7.65 mmol) was added in batches under N$_2$. The reaction mixture was stirred at room temperature overnight.

Saturated ammonium chloride aqueous solution was added, the organic phase was separated and washed successively with water and saturated brine, and then dried over anhydrous sodium sulfate and concentrated. The resulting residue was purified by column chromatography to give the title product (2.28 g, yield: 79%).

$^1$H NMR (400 MHz, CDCl$_3$) δ 7.37 (m, 3H), 6.75 (dd, J=7.6, 1.2 Hz), 4.21 (s, 4H), 3.95 (m, 5H), 3.66 (m, 2H), 3.22 (m, 2H), 3.09 (s, 3H), 2.87 (br, 1H), 2.28 (br, 1H), 0.91 (s, 9H), 0.12 (s, 3H), 0.09 (s, 3H).

Step 6: tert-butyldimethyl(((2R,3R,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-yl)methoxy)silane (3R,4S,5S,6R)-6-(((tert-butyldimethylsilyl)oxy)methyl)-2-(4-chloro-3-((2,3-dihydrobenzo[b][1,4]dioxin-6-yl)methyl)phenyl)-2-methoxytetrahydro-2H-pyran-3,4,5-triol (2.4 g, 4.23 mmol) was dissolved in a mixed solvent of THF (21 mL) and DMF (7 mL), then 60% sodium hydride (761 mg, 19.1 mmol) was added at 0° C. The reaction mixture was stirred at room temperature for 30 minutes, then benzyl bromide (3.6 g, 21.2 mmol) was added. The reaction mixture was stirred at room temperature for 5 hours. Saturated ammonium chloride aqueous solution was added, the reaction mixture was extracted with ethyl acetate, the organic phase was washed successively with water and saturated brine, and then dried over anhydrous sodium sulfate and concentrated. The resulting residue was purified by column chromatography to give the title product (3.3 g, yield: 93%).

$^1$H NMR (400 MHz, CDCl$_3$) δ 7.53-6.93 (m, 16H), 7.00 (dd, J=7.6, 1.6 Hz, 2H), 6.66 (m, 3H), 4.95-4.83 (m, 3H), 4.72 (d, J=10.7 Hz, 1H), 4.50 (d, J=10.5 Hz, 1H), 4.23-3.60 (m, 13H), 3.06 (s, 3H), 0.93 (s, 9H), 0.11 (s, 3H), 0.78 (s, 3H).

Step 7: ((2R,3R,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-yl)methanol Tert-butyldimethyl(((2R,3R,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-yl)methoxy)silane (2.5 g, 3.0 mmol) was dissolved in methanol (8 mL), then acetyl chloride (38 mg, 0.45 mmol) was added. The reaction mixture was stirred at room temperature for 1 hour, and concentrated under reduced pressure, then the resulting residue was purified by column chromatography to give the title product (1.6 g, yield: 73.7%).

$^1$H NMR (400 MHz, CDCl$_3$) δ 7.31 (m, 13H), 7.20 (m, 3H), 6.97 (m, 2H), 6.73 (d, J=8.4 Hz, 1H), 6.65 (m, 2H), 4.89 (m, 3H), 4.68 (d, J=10.8 Hz, 1H), 4.46 (d, J=10.8 Hz, 1H), 4.20 (s, 4H), 4.18 (m, 1H), 3.80 (m, 7H), 3.29 (d, J=9.2 Hz, 1H), 3.08 (s, 3H).

Step 8: (2S,3S,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-carbaldehyde Oxalyl chloride (263 mg, 1.38 mmol) was dissolved in dichloromethane (3 mL), then a solution of DMSO (215 mg, 2.76 mmol) in dichloromethane (2 mL) was added after it was cooled to −78° C. The reaction mixture was stirred at this temperature for 30 minutes, then a solution of ((2R,3R,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-yl)methanol (1.0 g, 1.38 mmol) in dichloromethane (4 mL) was added. The reaction mixture was stirred at −78° C. for 1 hour, then triethylamine (697 mg, 6.9 mmol) was added. The reaction mixture was slowly warmed up to room temperature, and stirred at room temperature for another 30 minutes. 1M hydrochloric acid was added in an ice-water bath. The reaction solution was separated, and the aqueous phase was extracted with dichloromethane. The organic phases were combined and washed with saturated brine, and then dried over anhydrous sodium sulfate and concentrated to give the crude title product (902 mg, yield: 90%).

Step 9: ((3S,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2,2-diyl)dimethanol (2S,3S,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2-carbaldehyde (200 mg, 0.28 mmol) was dissolved in 1,4-dioxane (10 mL), then paraformaldehyde (40 mg, 1.5 mmol) and 85% KOH aqueous solution (containing KOH (68 mg, 1.2 mmol)) were added under stirring under $N_2$. The reaction mixture was heated to 50° C. and stirred for 2 hours, then cooled and filtered. The filtrate was concentrated by rotary evaporation (the bath temperature was below 50° C.). The resulting residue was dissolved in dichloromethane, the mixture was washed with saturated brine, then dried over anhydrous sodium sulfate and concentrated. The resulting residue was purified by column chromatography to give the title product (116 mg, yield: 55%).
$^1$H NMR (400 MHz, CDCl$_3$) δ 7.44-7.16 (m, 16H), 7.02 (m, 2H), 6.77 (d, J=8.2 Hz, 1H), 6.59 (m, 2H), 4.95 (m, 3H), 4.64 (m, 2H), 4.41 (m, 2H), 4.22 (s, 4H), 4.00 (m, 4H), 3.83 (m, 3H), 3.66 (t, J=11.4 Hz, 1H), 3.24 (d, J=9.9 Hz, 1H), 3.07 (s, 3H), 2.95 (dd, J=11.4, 2.2 Hz, 1H).

Step 10: (1S,2S,3S,4R,5S)-5-(4-chloro-3-((2,3-dihydrobenzo[b][1,4]dioxin-6-yl)methyl)phenyl)-1-(hydroxymethyl)-6,8-dioxabicyclo[3.2.1]octane-2,3,4-triol ((3S,4S,5R)-3,4,5-tris(benzyloxy)-6-(4-chloro-3-((2,3-dihydrobenzo[b][1,4]dioxin-6-yl)methyl)phenyl)-6-methoxytetrahydro-2H-pyran-2,2-diyl)dimethanol (50 mg, 0.066 mmol) was dissolved in a mixed solvent of tetrahydrofuran (0.5 mL) and methanol (5 mL), then o-dichlorobenzene (147 mg, 1 mmol) and Pd/C catalyst (25 mg, 10%) were added successively under $N_2$. The reaction mixture was purged three times with hydrogen and stirred at room temperature under normal pressure under hydrogen for 3 hours. The reaction mixture was filtered through celite, and the filtrate was concentrated to dryness. The resulting residue was purified by column chromatography to give the final product (21.7 mg, yield: 73%).
MS m/z (ESI): 450.8 [M+1].
$^1$H NMR (400 MHz, MeOD) δ 7.36 (d, J=2.0 Hz, 1H), 7.27 (m, 2H), 6.59 (dd, J=11.6, 1.2 Hz), 6.53 (m, 2H), 4.07 (s, 4H), 4.04 (d, J=7.8 Hz, 1H), 3.87 (s, 2H), 3.73 (m, 2H), 3.53 (m, 4H).

Example 2: (1S,2S,3S,4R,5S)-5-(4-cyclopropyl-3-((2,3-dihydrobenzo[b][1,4]dioxin-6-yl)methyl)phenyl)-1-(hydroxymethyl)-6,8-dioxabicyclo[3.2.1]octane-2,3,4-triol

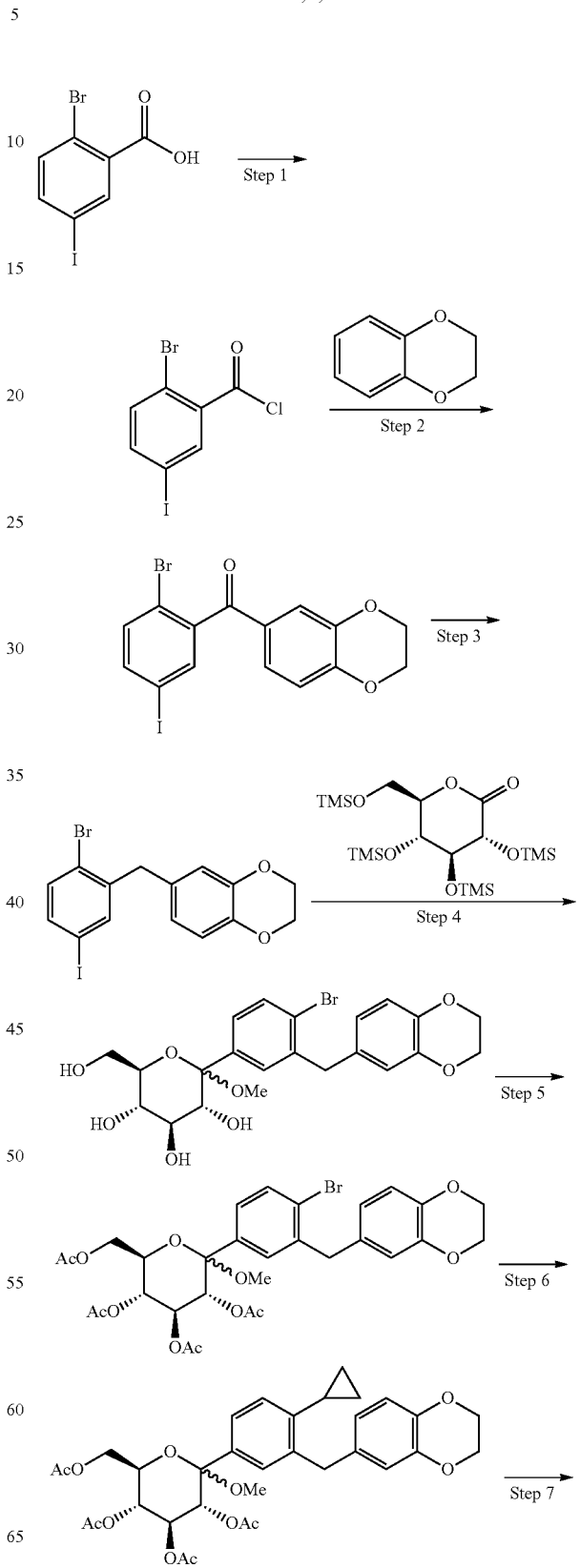

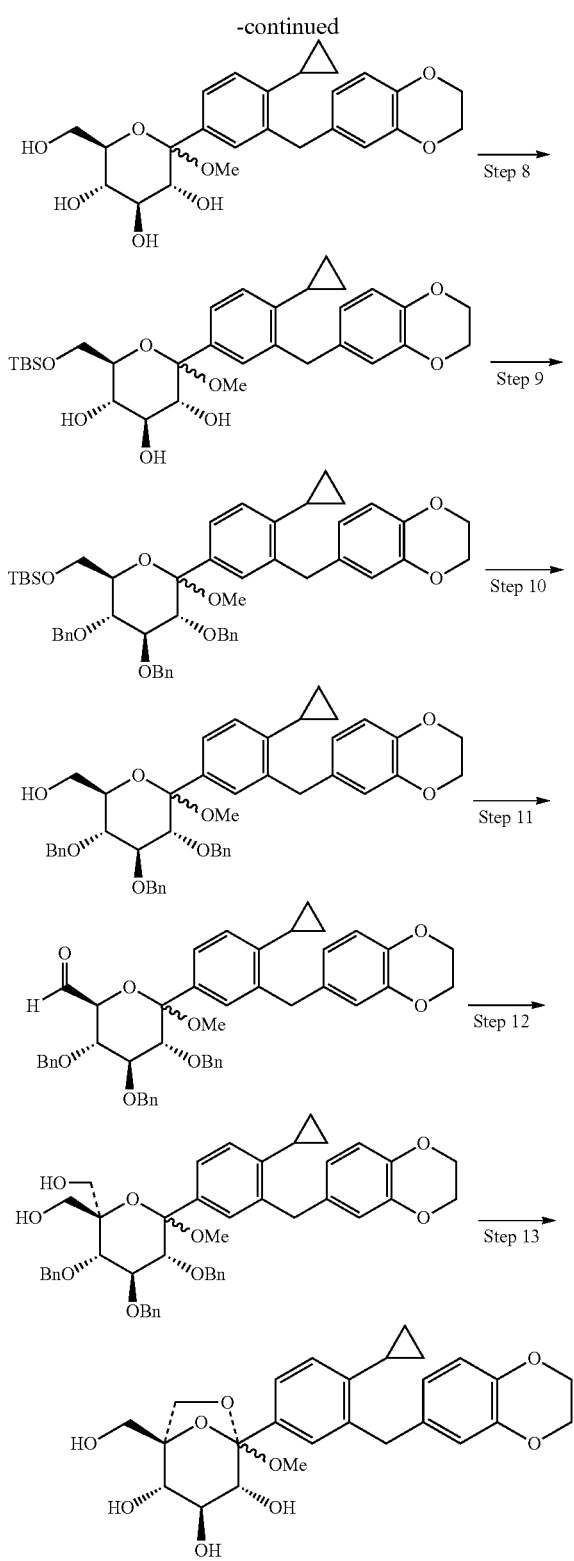

Step 1: 2-bromo-5-iodobenzoyl chloride

To a 50 mL flask, 2-bromo-5-iodobenzoic acid (50 g, 150 mmol) was added, then purged with $N_2$ three times and anhydrous dichloromethane (500 mL) was added. The reaction mixture was cooled to 0° C., then a catalytic amount of DMF (2.0 mL) was added, and then oxalyl chloride (19.4 mL, 229 mmol) was slowly added. The reaction mixture was warmed up to room temperature and stirred for 3 hours. When the reaction system became a clear solution, the stirring was stopped. Then, dichloromethane and excess oxalyl chloride were removed by rotary evaporation. The resulting residue was used directly in the next step.

Step 2: (2-bromo-5-iodophenyl)-(2,3-dihydrobenzo [b][1,4]dioxin-6-yl)methanone

The crude product obtained above was dissolved in anhydrous dichloromethane (500 mL) after purging with $N_2$, then benzodioxine (21.9 ml, 181 mmol) was added. The reaction mixture was cooled to 0° C., then $AlCl_3$ (24 g) was added in batches. The reaction mixture was slowly warmed up to room temperature overnight. The reaction mixture was poured into ice, and then extracted with dichloromethane (300 ml×3). The reaction solvent was removed by rotary evaporation to give a white solid (68 g), which was used directly in the next step.

Step 3: 6-(2-bromo-5-iodobenzyl)-2,3-dihydrobenzo [b][1,4]dioxine (2-bromo-5-iodophenyl)-(2, 3-dihydrobenzo[b][1,4]dioxin-6-yl)methanone (68 g) was dissolved in acetonitrile (500 mL). Then, triethylsilane (76.8 mL, 481 mmol) was added after the reaction mixture was cooled to 0° C., and then boron trifluoride etherate (58.8 mL, 464 mmol) was slowly added. The reaction mixture was stirred at room temperature overnight. The reaction was quenched with a saturated solution of $NaHCO_3$, then extracted with ethyl acetate (300 mL×3). The reaction solvent was removed by rotary evaporation. The resulting residue was purified by column chromatography, then further recrystallized with ethyl acetate and petroleum ether to give a white solid (40 g, total yield of three steps: 62%).

$^1$H NMR (400 MHz, $CDCl_3$) δ 7.43 (d, J=2.2 Hz, 1H), 7.37 (dd, J=8.3, 2.2 Hz, 1H), 7.24 (d, J=2.7 Hz, 1H), 6.82-6.76 (m, 1H), 6.69-6.61 (m, 2H), 4.23 (s, 4H), 3.92 (s, 2H).

Step 4: (3R,4S,5S,6R)-2-(4-bromo-3-((2,3-dihydrobenzo[b][1,4]dioxin-6-yl)methyl)phenyl)-6-(hydroxymethyl)-2-methoxytetrahydro-2H-pyran-3,4,5-triol 6-(2-bromo-5-iodobenzyl)-2,3-dihydrobenzo[b][1,4]dioxine (5 g, 11.6 mmol) was dissolved in a mixed solvent of THF (20 mL) and toluene (20 mL) in a dry ice-acetone bath, then n-BuLi in n-hexane (1.6M, 11 mL, 17.6 mmoL) was slowly added. The reaction mixture was stirred at this temperature for 1 hour. A solution of (3R,4S,5R,6R)-3,4,5-tris(trimethylsilyloxy)-6-trimethyl silyloxymethyltetrahydropyran-2-one (6 g, 12.8 mmol) in toluene (10 mL) was slowly added. The reaction mixture was stirred at −70° C. for 2 hours, and a solution of MsOH (2.7 g, 27.8 mmol) in methanol (5 mL) was added. The reaction mixture was naturally warmed up to room temperature and stirred overnight. Saturated sodium bicarbonate solution was added, and the aqueous phase was extracted with EtOAc. The organic phase was washed three times with saturated brine, and then dried over anhydrous sodium sulfate and concentrated. The resulting residue was purified by column chromatography to give a pale yellow foamy solid (2.52 g, yield: 43.7%).

¹H NMR (400 MHz, CDCl₃) δ 7.47 (d, J=8.3 Hz, 1H), 7.34 (t, J=11.0 Hz, 1H), 7.18 (d, J=8.2 Hz, 1H), 6.75 (d, J=8.1 Hz, 1H), 6.65 (dd, J=10.5, 2.1 Hz, 2H), 4.17 (d, J=30.4 Hz, 4H), 4.06-3.78 (m, 5H), 3.62 (dt, J=19.7, 9.4 Hz, 2H), 3.23 (d, J=9.3 Hz, 1H), 2.97 (s, 3H).

Step 5: (3R,4S,5R,6R)-6-(acetoxymethyl)-2-(4-bromo-3-((2,3-dihydrobenzo[b][1,4]dioxin-6-yl)methyl)phenyl)-2-methoxytetrahydro-2H-pyran-3,4,5-triyl triacetate (3R,4S,5S,6R)-2-(4-bromo-3-((2,3-dihydrobenzo[b][1,4]dioxin-6-yl)methyl)phenyl)-6-(hydroxymethyl)-2-methoxytetrahydro-2H-pyran-3,4,5-triol was dissolved in dichloromethane (20 mL), then pyridine (3.2 g, 40 mmol), Ac₂O (4.1 g, 40 mmol) and DMAP (61 mg, 0.5 mmol) were added successively. The reaction mixture was stirred at room temperature for 2 hours. The solvent was removed under reduced pressure. The resulting residue was dissolved in EtOAc, the mixture was washed successively with 1M hydrochloric acid (two times) and saturated brine, then dried over anhydrous sodium sulfate and concentrated to give a yellow foamy solid (2.9 g, yield: 87.2%).

¹H NMR (400 MHz, CDCl₃) δ 7.48 (dd, J=14.0, 7.3 Hz, 1H), 7.17-7.06 (m, 2H), 6.71 (d, J=8.2 Hz, 1H), 6.63-6.45 (m, 2H), 5.49 (t, J=9.7 Hz, 1H), 5.15 (t, J=9.8 Hz, 1H), 4.87 (d, J=10.0 Hz, 1H), 4.27 (dd, J=12.2, 5.0 Hz, 1H), 4.20-4.10 (m, 5H), 3.02 (s, 3H), 2.04 (s, 3H), 1.98 (d, J=2.8 Hz, 3H), 1.89 (d, J=8.3 Hz, 3H), 1.75 (s, 3H).

Step 6: (3R,4S,5R,6R)-6-(acetoxymethyl)-2-(4-cyclopropyl-3-((2,3-dihydrobenzo[b][1,4]dioxin-6-yl)methyl)phenyl)-2-methoxytetrahydro-2H-pyran-3,4,5-triyl triacetate (3R,4S,5R,6R)-6-(acetoxymethyl)-2-(4-bromo-3-((2,3-dihydrobenzo[b][1,4]dioxin-6-yl)methyl)phenyl)-2-methoxytetrahydro-2H-pyran-3,4,5-triyl triacetate (595 mg, 0.894 mmol), cyclopropylboronic acid (100 mg, 1.16 mmol), palladium acetate (10 mg, 0.0447 mmol) and K₃PO₄ (663 mg, 3.13 mmol) were dissolved in a mixed solvent of toluene (4 mL) and water (0.2 mL). The reaction mixture was purged with N₂ for 15 minutes, then PCy₃ (25 mg, 0.0894 mmol) was added, and then N₂ was sequentially purged for 30 minutes. The reaction mixture was heated to 100° C. and reacted in a sealed tube for 6 hours, then cooled, diluted with EtOAc, and then washed successively with water and saturated brine, and then dried over anhydrous sodium sulfate and concentrated. The resulting residue was purified by column chromatography to give a white foamy solid (415 mg, yield: 74%).

¹H NMR (400 MHz, CDCl₃) δ 7.33-7.23 (m, 1H), 7.15 (d, J=1.8 Hz, 1H), 6.98 (d, J=8.1 Hz, 1H), 6.75 (d, J=8.2 Hz, 1H), 6.61-6.52 (m, 2H), 5.58 (t, J=9.7 Hz, 1H), 5.28-5.18 (m, 1H), 4.97 (d, J=10.0 Hz, 1H), 4.34 (dd, J=12.2, 4.9 Hz, 1H), 4.29-4.17 (m, 5H), 4.03 (m, 3H), 3.11 (s, 3H), 2.10 (s, 3H), 2.06 (s, 3H), 1.95 (s, 3H), 1.89-1.74 (m, 4H), 0.91-0.76 (m, 2H), 0.70-0.50 (m, 2H).

Step 7: (3R,4S,5S,6R)-2-(4-cyclopropyl-3-((2,3-dihydrobenzo[b][1,4]dioxin-6-yl)methyl)phenyl)-6-(hydroxymethyl)-2-methoxytetrahydro-2H-pyran-3,4,5-triol (3R,4S,5R,6R)-6-(acetoxymethyl)-2-(4-cyclopropyl-3-((2,3-dihydrobenzo[b][1,4]dioxin-6-yl)methyl)phenyl)-2-methoxytetrahydro-2H-pyran-3,4,5-triyl triacetate (1.65 g, 2.63 mmol) was dissolved in a mixed solvent of THF (9 mL), methanol (6 mL) and water (3 mL), then LiOH.H₂O (122 mg, 2.9 mmol) was added. The reaction mixture was stirred at room temperature for 2 hours. The organic solvent was removed under reduced pressure. The resulting residue was dissolved in EtOAc, then washed successively with 5% NaHSO₄ aqueous solution and saturated brine, then dried over anhydrous sodium sulfate and concentrated to give a white foamy solid (1.22 g, yield: 100%).

¹H NMR (400 MHz, CDCl₃) δ 7.39-7.16 (m, 2H), 7.00 (d, J=8.1 Hz, 1H), 6.76 (d, J=8.6 Hz, 1H), 6.68-6.53 (m, 2H), 4.22 (s, 4H), 4.17-3.84 (m, 5H), 3.79-3.59 (m, 2H), 3.24 (d, J=9.3 Hz, 1H), 3.14 (s, 3H), 1.89-1.74 (m, 1H), 0.87 (d, J=6.9 Hz, 2H), 0.63 (t, J=5.2 Hz, 2H).

Step 8: (3R,4S,5S,6R)-6-(((tert-butyldimethylslyl)oxy)methyl)-2-(4-cyclopropyl-3-((2,3-dihydrobenzo[b][1,4]dioxin-6-yl)methyl)phenyl)-2-methoxytetrahydro-2H-pyran-3,4,5-triol (3R,4S,5S,6R)-2-(4-cyclopropyl-3-((2,3-dihydrobenzo[b][1,4]dioxin-6-yl)methyl)phenyl)-6-(hydroxymethyl)-2-methoxytetrahydro-2H-pyran-3,4,5-triol (1.22 g, 2.66 mmol) was dissolved in dichloromethane (15 mL), then imidazole (543 mg, 7.98 mmol) and DMAP (33 mg, 0.27 mmol) were added, and then TBSCl (420 mg, 2.79 mmol) was added in batches under N₂. The reaction mixture was stirred at room temperature overnight. A saturated ammonium chloride aqueous solution was added, the organic phase was separated and washed with saturated brine, then dried over anhydrous sodium sulfate and concentrated to give a pale yellow foamy solid (1.26 g, yield: 82.7%).

¹H NMR (400 MHz, CDCl₃) δ 7.29 (m, 2H), 6.99 (d, J=7.7 Hz, 1H), 6.74 (d, J=8.5 Hz, 1H), 6.60 (m, 2H), 4.22 (s, 4H), 4.18-3.86 (m, 5H), 3.69 (d, J=3.8 Hz, 2H), 3.27 (dd, J=9.2, 7.6 Hz, 1H), 3.13 (s, 3H), 1.80 (m, 1H), 1.02-0.80 (m, 11H), 0.62 (m, 2H), 0.18 (s, 3H), 0.07 (s, 3H).

Step 9: tert-butyldimethyl(((2R,3R,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-yl)methoxy)silane (3R,4S,5 S, 6R)-6-(((tert-butyldimethylslyl)oxy)methyl)-2-(4-cyclopropyl-3-((2,3-dihydrobenzo[b][1,4]dioxin-6-yl)methyl)phenyl)-2-methoxytetrahydro-2H-pyran-3,4,5-triol (1.26 g, 2.2 mmol) was dissolved in a mixed solvent of THF (12 mL) and DMF (4 mL), then NaH (60%, 396 mg, 9.9 mmol) was added in batches in an ice water bath. The reaction mixture was heated to room temperature and stirred for 30 minutes. BnBr (1.88 g, 11 mmol) was added dropwise in an ice water bath, then the reaction mixture was heated to room temperature and stirred overnight. A saturated ammonium chloride aqueous solution and EtOAc were added. The organic phase was separated and washed with water and saturated brine, then dried over anhydrous sodium sulfate and concentrated. The resulting residue was purified by column chromatography to give a white viscous substance (1.38 g, yield: 74%).

Step 10: ((2R,3R,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-yl)methanol Tert-butyldimethyl(((2R,3R,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-yl) methoxy)silane (1.38 g, 1.6 mmol) was dissolved in methanol (15 mL), then AcCl (0.02 mL, 0.25 mmol)) was added in an ice-water bath. The reaction mixture was naturally warmed up to room temperature and stirred for 1 hour, then concentrated under reduced pressure to give a yellow foamy solid (1.2 g, yield: 100%).

Step 11: (2S,3S,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-carbaldehyde Oxalyl chloride (52 mg, 0.41 mmol) was dissolved in DCM (1.5 mL) at room temperature in a dry ice-acetone bath. Then, a solution of DMSO (42 mg, 0.54 mmol) in DCM (1.5 mL) was added dropwise, and the temperature was controlled at about −70° C. The reaction mixture was stirred for 25 minutes, then a solution of ((2R,3R,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-yl)methanol (200 mg, 0.27 mmol) in DCM (2 mL) was added. The reaction mixture was stirred at −70° C. for 1 hour, then triethylamine (136 mg, 1.35 mmol) was added dropwise. The reaction mixture was stirred at room temperature for 30 minutes. 1M hydrochloric acid was added in an ice-water bath. The mixture was extracted with DCM, the organic phase was washed twice with saturated brine, and then dried over anhydrous sodium sulfate and concentrated to give a white foamy solid, which was used directly in the next step.

Step 12: ((3S,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2,2-diyl)dimethanol (2S,3S,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2-carbaldehyde (170 mg, 0.23 mmol) was dissolved in 1,4-dioxane (6 mL), then paraformaldehyde solution (33 mg, 1.1 mmol) and potassium hydroxide (55 mg, 0.98 mmol) were added under $N_2$. The reaction mixture was heated to 50° C. for 2 hours. The reaction solution was left to stand, filtered, then the filtrate was concentrated to dryness below 50° C. The resulting residue was dissolved in dichloromethane (50 mL), the mixture was washed with saturated brine (50 mL×2), then dried over anhydrous sodium sulfate and filtered. The filtrate was concentrated. The resulting residue was purified by column chromatography (eluent PE:EA=5:1~3:1) to give the title product ((3S,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2,2-diyl)dimethanol (100 mg, a yellow oil, yield: 56%).

$^1$H NMR (400 Hz, CDCl$_3$): δ 7.22-7.47 (m, 15H), 7.08-7.14 (m, 2H), 7.01 (d, J=8.0 Hz, 1H), 6.69 (d, J=8.0 Hz, 1H), 6.58-6.67 (m, 2H), 4.90 (m, 3H), 4.73 (q, J=8.0 Hz, 1H), 4.56 (d, J=8.0 Hz, 1H), 4.35-4.48 (m, 2H), 4.17-4.26 (m, 6H), 4.15 (t, J=4.0 Hz, 1H), 4.07 (d, J=9.6 Hz, 1H), 3.92-4.02 (m, 2H), 3.90 (s, 2H), 3.69-3.77 (m, 1H), 3.33 (d, J=9.6 Hz, 1H), 3.16 (s, 3H), 1.84-1.93 (m, 1H), 0.87-1.00 (m, 2H), 0.63-0.73 (m, 2H).

Step 13: (1S,2S,3S,4R,5S)-5-(4-cyclopropyl-3-((2,3-dihydrobenzo[b][1,4]dioxin-6-yl)methyl)phenyl)-1-(hydroxymethyl)-6,8-dioxabicyclo[3.2.1]octane-2,3,4-triol ((3S,4S,5R)-3,4,5-tris(benzyloxy)-6-(4-cyclopropyl-3-((2,3-dihydrobenzo[b][1,4]dioxin-6-yl)methyl)phenyl)-6-methoxytetrahydro-2H-pyran-2,2-diyl)dimethanol (50 mg, 0.066 mmol) was dissolved in a mixed solvent (6 mL) of tetrahydrofuran and methanol (v:v=1:5), then 10% Pd/C (25 mg) was added. The reaction mixture was purged with hydrogen three times and stirred at room temperature for 3 hours, then filtered. The filtrate was concentrated under reduced pressure. The resulting residue was purified by column chromatography (CH$_2$Cl$_2$:MeOH=25:1-15:1) to give the title product (1S,2S,3S,4R,5S)-5-(4-cyclopropyl-3-((2,3-dihydrobenzo[b][1,4]dioxin-6-yl)methyl)phenyl)-1-(hydroxymethyl)-6,8-dioxabicyclo[3.2.1]octane-2,3,4-triol (25 mg, a white solid, yield: 83%).

MS m/z (ESI): 457.0 [M+1].
$^1$H NMR (400 Hz, CD$_3$OD): δ 7.31-7.36 (m, 2H), 6.97 (d, J=8.4 Hz, 1H), 6.69 (d, J=8.0 Hz, 1H), 6.56-6.63 (m, 2H), 4.17 (s, 4H), 4.15 (d, J=7.2 Hz, 1H), 4.05 (s, 2H), 3.76-3.87 (m, 2H), 3.57-3.72 (m, 4H), 1.78-1.88 (m, 1H), 0.81-0.87 (m, 2H), 0.53-0.58 (m, 2H).

Example 3: (2S,3R,4R,5S,6R)-2-(7-((2,3-dihydrobenzo[b][1,4]dioxin-6-yl)methyl)-2,3-dihydrobenzofuran-5-yl)-6-(hydroxymethyl)tetrahydro-2H-thiopyran-3,4,5-triol

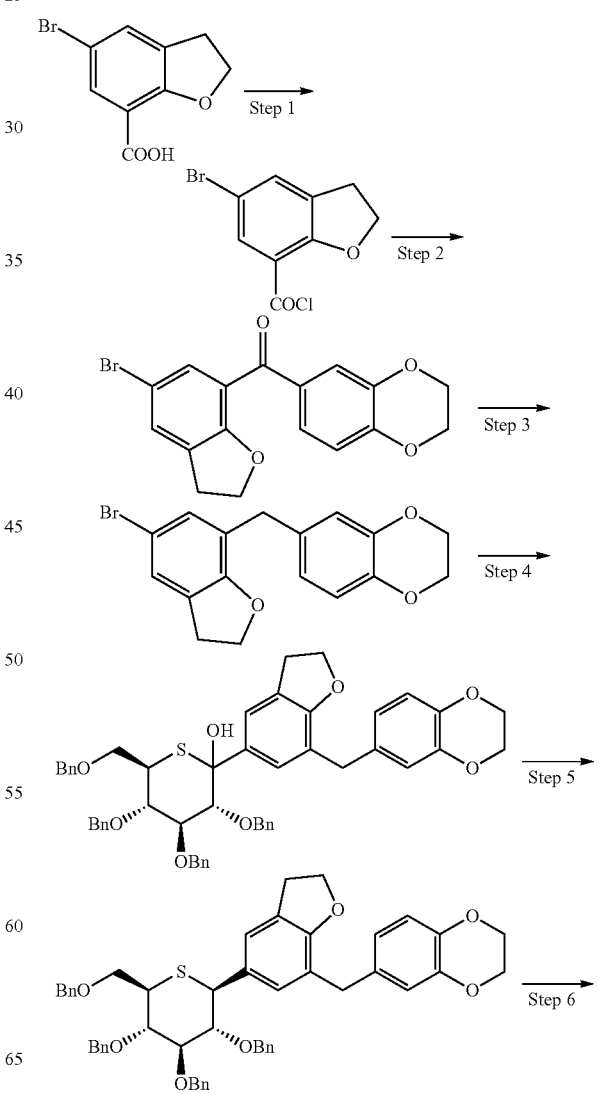

-continued

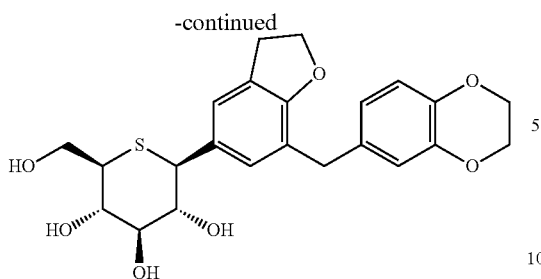

Step 1: 5-bromo-2,3-dihydrobenzofuran-7-carbonyl chloride

To a 50 mL flask, 5-bromo-2,3-dihydrobenzofuran-7-carboxylic acid (1.0 g, 4.1 mmol) was added, then anhydrous dichloromethane (15 mL) was added after purging with $N_2$ three times. The reaction mixture was cooled to 0° C., then a catalytic amount of DMF (1 drop) was added, and then oxalyl chloride (0.53 mL, 6.1 mmol) was slowly added. The reaction mixture was warmed up to room temperature and stirred for 3 hours. When the reaction solution became a clear solution, the stirring was stopped. Dichloromethane and excess oxalyl chloride were removed by rotary evaporation, and the crude product was used directly in the next step.

Step 2: (5-bromo-2,3-dihydrobenzofuran-7-yl)-(2,3-dihydrobenzo[b][1,4]dioxin-6-yl)methanone The crude product obtained above was dissolved in anhydrous dichloromethane (20 mL) after purging with $N_2$, then benzodioxine (0.6 ml, 5.0 mmol) was added. The reaction mixture was cooled to 0° C., then $AlCl_3$ (0.65 g, 5.0 mmol) was added in batches. The reaction mixture was slowly warmed up to room temperature and stirred overnight, then poured into ice. The mixture was extracted with dichloromethane (30 ml×3), and the organic phase was removed by rotary evaporation. The resulting residue was purified by column chromatography to obtain a white solid (1 g, yield: 68%).

$^1$H NMR (400 MHz, $CDCl_3$) δ 7.37-7.31 (m, 3H), 7.29 (dd, J=8.4, 2.1 Hz, 1H), 6.83 (d, J=8.4 Hz, 1H), 4.53 (t, J=8.8 Hz, 2H), 4.23 (ddd, J=8.1, 6.1, 2.8 Hz, 4H), 3.16 (t, J=8.8 Hz, 2H).

Step 3: 6-((5-bromo-2,3-dihydrobenzofuran-7-yl)methyl)-2,3-dihydrobenzo[b][1,4]dioxine (5-bromo-2,3-dihydrobenzofuran-7-yl)-(2,3-dihydrobenzo[b][1,4]dioxin-6-yl)methanone (1 g, 2.8 mmol) was dissolved in acetonitrile (20 mL). The reaction mixture was cooled to 0° C., then triethylsilane (1.4 mL, 9.0 mmol) was added, and then boron trifluoride etherate (1.1 mL, 9.0 mmol) was slowly added. The reaction mixture was stirred at room temperature overnight. The reaction was quenched with a saturated solution of $NaHCO_3$, then extracted with ethyl acetate (30 mL×3), and the reaction solvent was removed by rotary evaporation. The resulting residue was purified by column chromatography to give a colorless oily liquid (810 mg, yield: 85%).

$^1$H NMR (400 MHz, $CDCl_3$) δ 7.18-7.08 (m, 1H), 6.97 (dd, J=6.9, 5.5 Hz, 1H), 6.81-6.73 (m, 1H), 6.72-6.64 (m, 2H), 4.55 (dd, J=10.8, 6.7 Hz, 2H), 4.30-4.17 (m, 4H), 3.74 (s, 2H), 3.18 (t, J=8.7 Hz, 2H).

Step 4: (3R,4S,5S,6R)-3,4,5-tris(benzyloxy)-6-((benzyloxy)methyl)-2-(7-((2,3-di hydrobenzo[b][1,4]dioxin-6-yl)methyl)-2,3-dihydrobenzo furan-5-yl)tetrahydro-2H-thio pyran-2-ol To a 50 mL flask, the product obtained in the previous step was added (400 mg, 1.16 mmol), then dissolved in anhydrous THF (15 mL) after purging with $N_2$. The reaction mixture was cooled in a dry ice-acetone bath, then n-BuLi solution (1.2 mmol) was slowly added dropwise. The reaction mixture was stirred for 1.0 hour, then a solution of 6-((5-bromo-2,3-dihydrobenzofuran-7-yl)methyl)-2,3-dihydrobenzo[b][1,4]dioxine (664 mg, 1.2 mmol) in toluene (5.0 mL) was slowly added dropwise. The reaction mixture was slowly warmed up to room temperature and stirred for 3 hours. The reaction mixture was quenched with ammonium chloride aqueous solution and extracted with ethyl acetate (30 mL×3), then dried over anhydrous sodium sulfate, and then the solvent was removed by rotary evaporation. The resulting residue was purified by column chromatography to give a colorless oily liquid (190 mg, yield: 20%).

Step 5: 6-((5-((2S,3R,4R,5S,6R)-3,4,5-tris(benzyloxy)-6-((benzyloxy)methyl)tetrahydro-2H-thiopyran-2-yl)-2,3-dihydrobenzofuran-7-yl)methyl)-2,3-dihydrobenzo[b][1,4]dioxine To a 25 mL flask, the product obtained in the previous step (190 mg, 0.25 mmol) was added, then dissolved in acetonitrile (10 mL) after purging with $N_2$. The reaction mixture was stirred and cooled in an ice-salt bath, then triethylsilane (0.35 mL, 2.25 mmol) was added, and then boron trifluoride etherate (0.2 mL, 1.5 mmol) was slowly added. The reaction mixture was stirred for 2.0 hours, then the reaction was quenched with a saturated solution of $NaHCO_3$. The reaction mixture was extracted with ethyl acetate (20 mL×3), the organic phase was dried over anhydrous sodium sulfate, and the solvent was removed by rotary evaporation. The resulting residue was purified by column chromatography to give a colorless oily liquid (80 mg, yield: 43%).

Step 6: (2S,3R,4R,5S,6R)-2-(7-((2,3-dihydrobenzo[b][1,4]dioxin-6-yl)methyl)-2,3-dihydrobenzo furan-5-yl)-6-(hydroxymethyl)tetrahydro-2H-thiopyran-3,4,5-triol To a 25 mL flask, the product obtained in the previous step (80 mg, 0.1 mmol) and pentamethylbenzene (280 mg, 1.5 mg) were added, then dissolved in anhydrous dichloromethane (10 mL) after purging with $N_2$. The reaction mixture was stirred and cooled in a dry ice-acetone bath, then boron trichloride (0.8 mL, 0.6 mmol) was slowly added dropwise. The reaction mixture was stirred for 2.0 hours, then methanol (10 mL) was added, and the solvent was removed by rotary evaporation. The resulting residue was purified by column chromatography to give the title product (4.5 mg, yield: 10%).

$^1$H NMR (400 MHz, MeOD) δ 7.05 (s, 1H), 6.87 (s, 1H), 6.71-6.62 (m, 3H), 4.53 (t, J=8.7 Hz, 2H), 4.19 (s, 4H), 3.98-3.89 (m, 1H), 3.57 (dd, J=10.2, 9.1 Hz, 1H), 3.34 (s, 2H), 3.26-3.13 (m, 3H), 2.96 (ddd, J=10.2, 6.4, 3.7 Hz, 1H).

MS: calculated value ($C_{23}H_{26}O_7S$) (M+HCOO$^-$): 491.1376; measured value: 490.9.

Example 4: (2S,3R,4R,5S,6R)-2-(3-((2,3-dihydrobenzo[b][1,4]dioxin-6-yl)methyl)-4-methylphenyl)-6-(hydroxymethyl)tetrahydro-2H-thiopyran-3,4,5-triol

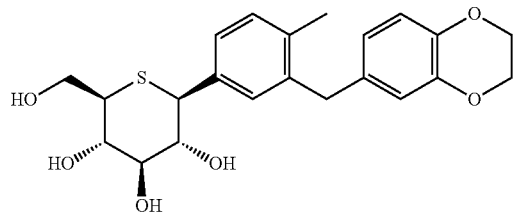 [SMILES: Cc1ccc([C@@H]2S[C@H](CO)[C@@H](O)[C@H](O)[C@H]2O)cc1Cc1ccc2c(c1)OCCO2]

The specific experimental procedure is the same as Example 3.

$^1$H NMR (400 MHz, CDCl$_3$) δ 7.11 (m, 3H), 6.75 (d, J=8.0 Hz, 1H), 6.58-6.56 (m, 2H), 4.19 (s, 4H), 3.92-3.77 (m, 8H), 3.71 (s, 1H), 3.42 (t, J=8.4 Hz, 1H), 3.10-3.07 (m, 1H), 2.85 (s, 1H), 2.79 (s, 1H), 2.19 (s, 3H).

Example 5: (2S,3R,4R,5S,6R)-2-(4-cyclopropyl-3-((2,3-dihydrobenzo[b][1,4]dioxin-6-yl)methyl)phenyl)-6-(hydroxymethyl)tetrahydro-2H-thiopyran-3,4,5-triol

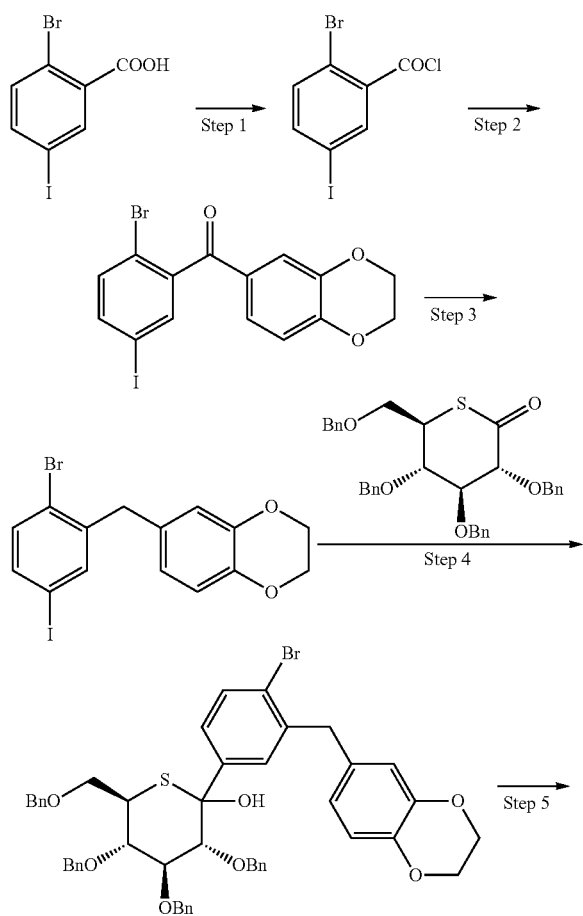

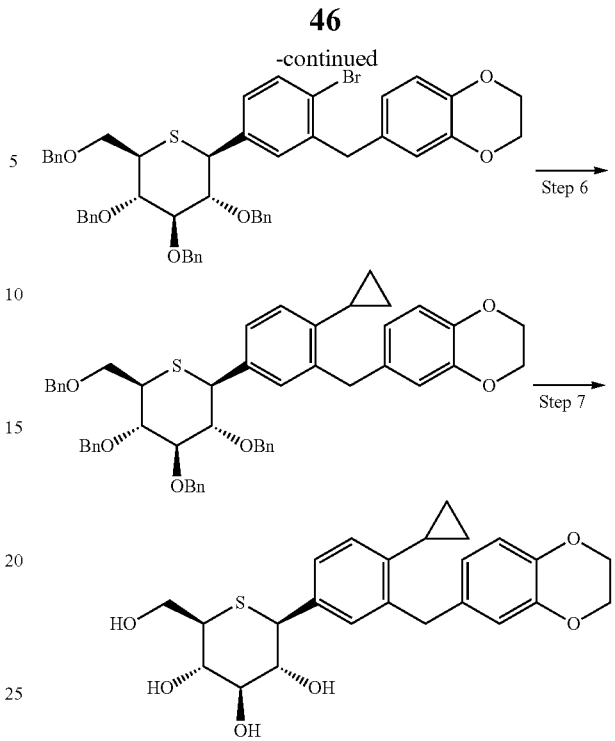

Step 1: 2-bromo-5-iodobenzoyl chloride 2-bromo-5-iodo-benzoic acid (5.0 g, 15.3 mmol) and oxalyl chloride (4.0 mL, 46.5 mmol) were dissolved in dichloromethane (30 mL), then the reaction mixture was cooled to 0° C., and then 2 drops of N, N-dimethylformamide were slowly added. The reaction mixture was naturally warmed up to room temperature and then stirred for 1 hour until the reaction system became clear. The solvent and excess oxalyl chloride were removed under reduced pressure. The resulting residue was dried in vacuo to give 2-bromo-5-iodobenzoyl chloride (5.25 g, a pale yellow oil, yield: nearly 100%).

Step 2: (2-bromo-5-iodophenyl)-(2,3-dihydrobenzo[b][1,4]dioxin-6-yl)methanone 2-bromo-5-iodobenzoyl chloride (5.25 g, 15.2 mmol) was dissolved in dichloromethane (20 mL), then 1,4-benzodioxine (2.14 g, 15.7 mmol) was added, and then aluminium trichloride (2.4 g, 18 mmol) was added in batches in an ice bath. When the reaction mixture was naturally warmed up to room temperature, the reaction system became black, and then stirred for another 3 hours. The reaction mixture was poured into ice water, the organic phase was separated, and the aqueous phase was extracted with dichloromethane. The organic phases were combined, then dried over anhydrous potassium carbonate, and the desiccant was filtered off. The filtrate was concentrated to give the title product (2-bromo-5-iodophenyl)-(2,3-dihydrobenzo[b][1,4]dioxin-6-yl)methanone (6.95 g, a pale yellow oil, yield: early 100%).

Step 3: 6-(2-bromo-5-iodobenzyl)-2,3-dihydrobenzo[b][1,4]dioxine (2-bromo-5-iodophenyl)-(2,3-dihydrobenzo[b][1,4]dioxin-6-yl)methanone (6.95 g, 15.6 mmol) was dissolved in a mixed solvent of dichloromethane (60 mL) and acetonitrile (60 mL). Then, an aqueous solution of triethylsilane (9 mL, 56 mmol) was added in an ice bath after purging with N₂, and then boron trifluoride etherate (7 mL, 55 mmol) was slowly added dropwise. The reaction mixture was naturally warmed up to room temperature, and slowly became clear. After 4 hours, the solvent and excess triethylsilane was removed. The crude product was purified by column chromatography (petroleum ether) to give 6-(2-bromo-5-iodobenzyl)-2,3-dihydrobenzo[b][1,4]dioxine (6.1 g, a white solid, yield: nearly 91%).

$^{1}$H NMR (400 MHz, CDCl$_3$): δ 7.45 (s, 1H), 7.38 (d, J=8.4 Hz, 1H), 7.27 (s, 1H), 6.80 (d, J=8.7 Hz, 1H), 6.66 (d, J=6.8 Hz, 2H), 4.25 (s, 4H), 3.93 (s, 2H).

Step 4: (3R,4S,5S,6R)-3,4,5-tris(benzyl oxy)-6-((benzyloxy)methyl)-2-(4-bromo-3-((2,3-dihydrobenzo[b][1,4]dioxin-6-yl)methyl)phenyl)tetrahydro-2H-thiopyran-2-ol To a 100 mL flask, 6-(2-bromo-5-iodobenzyl)-2,3-dihydrobenzo[b][1,4]dioxine (1.68 g, 3.89 mmol) was added, then THF (10 mL) and toluene (10 mL) were added as a solvent after purging with N₂. The reaction mixture was placed in a dry ice-acetone bath for 5 minutes, then n-BuLi (2.5 mL, 3.90 mmol) was slowly added dropwise. The reaction mixture was stirred for 0.5 hour, then a solution of (3R,4S,5S,6R)-3,4,5-tribenzyloxy-6-benzyloxymethyltetrahydrothiopyran-2-one (1.80 g, 3.24 mmol) in tetrahydrofuran was added. After the reaction mixture was stirred for 3 hours, the solvent was removed. The resulting residue was purified by flash column chromatography to give (3R,4S,5S,6R)-3,4,5-tris(benzyloxy)-6-((benzyloxy)methyl)-2-(4-bromo-3-((2,3-dihydrobenzo[b][1,4]dioxin-6-yl)methyl)phenyl)tetrahydro-2H-thiopyran-2-ol (a foamy solid 1.58 g, yield: 55%).

$^{1}$H NMR (400 MHz, CDCl$_3$): δ 7.56-7.46 (m, 2H), 7.38-7.23 (m, 14H), 7.15 (dt, J=15.3, 7.6 Hz, 5H), 6.71 (dd, J=13.8, 6.6 Hz, 4H), 6.61 (d, J=8.2 Hz, 1H), 4.95-4.77 (m, 3H), 4.64 (d, J=10.7 Hz, 1H), 4.51 (s, 2H), 4.46 (d, J=10.4 Hz, 1H), 4.16 (d, J=11.8 Hz, 4H), 4.12 (d, J=7.1 Hz, 1H), 4.05 (dd, J=16.8, 8.6 Hz, 2H), 3.94 (dd, J=17.0, 8.4 Hz, 3H), 3.85 (d, J=10.3 Hz, 1H), 3.61 (d, J=9.8 Hz, 1H), 3.49 (d, J=10.4 Hz, 1H).

Step 5: 6-(2-bromo-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine To a 50 mL flask, (3R,4S,5S,6R)-3,4,5-tris(benzyloxy)-6-((benzyloxy)methyl)-2-(4-bromo-3-((2,3-dihydrobenzo[b][1,4]dioxin-6-yl)methyl)phenyl)tetrahydro-2H-thiopyran-2-ol (2.0 g, 2.30 mmol) was added, then dichloromethane (15 mL) and acetonitrile (15 mL) were added as a solvent after purging with N₂. The reaction mixture was placed in an ice bath for 10 minutes, then triethylsilane (3.0 mL, 18.8 mmol) and boron trifluoride etherate (1.8 mL, 14.3 mmol) was added. After the reaction mixture was stirred for 3 hours, the solvent was removed. The resulting residue was purified by flash column chromatography to give 6-(2-bromo-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (1.20 g, an oil, yield: 62%).

$^{1}$H NMR (400 MHz, CDCl$_3$, ppm): δ 7.51 (d, J=8.2 Hz, 1H), 7.35-7.24 (m, 15H), 7.19-7.09 (m, 5H), 6.74-6.66 (m, 4H), 6.60 (dd, J=8.2, 2.1 Hz, 1H), 4.93-4.84 (m, 3H), 4.60 (t, J=8.5 Hz, 1H), 4.50 (d, J=10.9 Hz, 3H), 4.26-4.15 (m, 4H), 4.04 (d, J=15.4 Hz, 1H), 3.89 (ddd, J=15.2, 13.5, 9.0 Hz, 4H), 3.82-3.75 (m, 2H), 3.69 (dd, J=9.7, 2.8 Hz, 1H), 3.51 (t, J=8.9 Hz, 1H), 3.09 (ddd, J=10.4, 5.2, 2.9 Hz, 1H).

Step 6: 6-(2-cyclopropyl-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine To a 25 mL flask, 6-(2-bromo-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (0.4 g, 0.47 mmol), cyclopropylboronic acid (60 mg, 0.62 mmol), tricycloethylphosphine (60 mg, 0.22 mmol) and potassium phosphate (365 mg, 1.72 mmol) were added, then toluene (8 mL) and water (0.4 mL) were added after purging with N₂. Then, palladium acetate (30 mg, 0.13 mmol) was added under N₂. The reaction mixture was heated to 100° C. and refluxed overnight, then poured into water and extracted with ethyl acetate. The organic phases were combined, and washed with saturated brine, then dried over anhydrous sodium sulfate, and the solvent was removed. The resulting residue was purified by flash column chromatography to give the title product 6-(2-cyclopropyl-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (260 mg, an oil, yield: 69%).

$^{1}$H NMR (400 MHz, CDCl$_3$, ppm): δ 7.34-7.23 (m, 16H), 7.21-7.08 (m, 4H), 6.98 (d, J=7.9 Hz, 1H), 6.70-6.62 (m, 4H), 6.55 (dd, J=8.3, 2.1 Hz, 1H), 4.93-4.84 (m, 3H), 4.60 (d, J=10.8 Hz, 1H), 4.54-4.45 (m, 4H), 4.25-4.11 (m, 4H), 4.05 (d, J=38.2 Hz, 1H), 3.92 (td, J=15.5, 7.4 Hz, 3H), 3.81 (dt, J=8.4, 6.3 Hz, 2H), 3.74-3.66 (m, 1H), 3.51 (t, J=9.0 Hz, 1H), 3.09 (ddd, J=10.3, 5.2, 2.9 Hz, 1H), 1.85 (m, 1H) 0.87 (dt, J=15.8, 7.1 Hz, 2H), 0.62 (dd, J=5.4, 1.7 Hz, 2H).

Step 7: (2S,3R,4R,5S,6R)-2-(4-cyclopropyl-3-((2,3-dihydrobenzo[b][1,4]dioxin-6-yl)methyl)phenyl)-6-(hydroxymethyl)tetrahydro-2H-thiopyran-3,4,5-triol To a 50 mL flask, 6-(2-cyclopropyl-5-((2S,3R,4R,5S,6R)-3,4,5-tris(benzyloxy)-6-((benzyloxy)methyl)tetrahydro-2H-thiopyran-2-yl)benzyl)-2,3-dihydrobenzo[b][1,4]dioxine (260 mg, 0.32 mmol) and pentamethylbenzene (715 mg, 4.81 mmol) were added. Then, dichloromethane (10 mL) was added after purging with N₂. The reaction mixture was placed in a dry ice-acetone bath and stirred for 10 minutes, then boron trichloride (2.0 mL, 2.0 mmol) was slowly added. The reaction mixture was stirred for 3 hours, then the reaction was quenched with anhydrous methanol, and the reaction system became yellow. After the reaction mixture was stirred for 0.5 hour, the solvent was removed. The resulting residue was purified by reverse phase column chromatography to give (2S,3R,4R,5S,6R)-2-(4-cyclopropyl-3-((2,3-dihydrobenzo[b][1,4]dioxin-6-yl)methyl)phenyl)-6-(hydroxymethyl)tetrahydro-2H-thiopyran-3,4,5-triol (65 mg, an oil, yield: 45%).

MS m/z (ESI): 427.0.

$^{1}$H NMR (400 MHz, MeOD): δ 7.07-6.97 (m, 2H), 6.84 (d, J=7.9 Hz, 1H), 6.59 (d, J=8.3 Hz, 1H), 6.52-6.45 (m, 2H), 4.06 (s, 4H), 3.92 (s, 2H), 3.84 (dd, J=11.5, 3.6 Hz, 1H), 3.71-3.56 (m, 3H), 3.54-3.47 (m, 1H), 3.15 (t, J=8.4 Hz,

1H), 2.89 (ddd, J=10.1, 6.4, 3.7 Hz, 1H), 1.71 (tt, J=8.4, 5.4 Hz, 1H), 0.82-0.63 (m, 2H), 0.53-0.34 (m, 2H).

Example 6: (2S,3R,4R,5S,6R)-2-(5-((2,3-dihydrobenzo[b][1,4]dioxin-6-yl)methyl)-2-hydroxy-4-methylphenyl)-6-(hydroxymethyl)tetrahydro-2H-thiopyran-3,4,5-triol

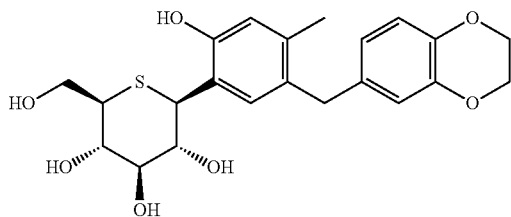 [SMILES: Cc1cc(O)c([C@@H]2S[C@H](CO)[C@@H](O)[C@H](O)[C@H]2O)cc1Cc1ccc2c(c1)OCCO2]

Step 1: Benzenemethyl 4-benzyloxy-2-methyl-benzoate 2-methyl-4-hydroxybenzoic acid (20.0 g, 0.13 mol), benzyl bromide (58.5 g, 0.34 mol) and potassium carbonate (46.9 g, 0.34 mol) were dissolved in acetone (500 mL). The reaction mixture was heated to 60° C. and refluxed overnight. After the reaction mixture was cooled to room temperature, anhydrous potassium carbonate was filtered off, and the filtrate was concentrated to give a pale yellow solid. The solid was further recrystallized to give benzenemethyl 4-benzyloxy-2-methyl-benzoate (34 g, a white solid, yield: 79%).

$^1$H NMR (400 MHz, CDCl$_3$): δ 7.98 (d, J=8.7 Hz, 1H), 7.49-7.29 (m, 10H), 6.87-6.77 (m, 2H), 5.31 (s, 2H), 5.10 (s, 2H), 2.61 (s, 3H).

Step 2: Benzenemethyl 4-(benzyloxy)-5-bromo-2-methylbenzoate and benzenemethyl 4-(benzyloxy)-3-bromo-2-methylbenzoate Benzenemethyl 4-benzyloxy-2-methyl-benzoate (34 g, 0.1 mol), sodium bromide (11.64 g, 0.11 mol) and potassium hydrogen persulfate (70 g, 0.11 mol) were dissolved in a mixed solvent of acetone (250 mL) and water (250 mL). After the reaction mixture was stirred at room temperature for 3 hours, the color of the reaction system changed from red to white. Sodium sulfite solution and ethyl acetate were added to the reaction mixture, the organic phase was separated and washed with saturated brine, and then dried and concentrated to give a mixture of benzenemethyl 4-(benzyloxy)-5-bromo-2-methylbenzoate and benzenemethyl 4-(benzyloxy)-3-bromo-2-methylbenzoate (35 g, an oil, yield: 85%).

Step 3: 4-benzyloxy-5-bromine-2-methylbenzoic acid

The mixture of benzenemethyl 4-(benzyloxy)-5-bromo-2-methylbenzoate and benzenemethyl 4-(benzyloxy)-3-bromo-2-methylbenzoate (35 g, 85.2 mmol) was dissolved in the mixed solvent of tetrahydrofuran (50 mL) and sodium hydroxide (150 mL). The reaction mixture was heated to 100° C. and refluxed overnight. The reaction mixture was cooled to room temperature, then hydrochloric acid aqueous solution was added, and then ethyl acetate was added. The organic phase was separated, then dried over anhydrous sodium sulfate and concentrated to give a pale yellow solid. The solid was further recrystallized with ethyl acetate to give 4-benzyloxy-5-bromine-2-methylbenzoic acid (13 g, a white solid, yield: 48%).

$^1$H NMR (400 MHz, DMSO-d$_6$): δ 12.77 (s, 1H), 8.03 (s, 1H), 7.49 (d, J=7.1 Hz, 2H), 7.42 (t, J=7.4 Hz, 2H), 7.35 (t, J=7.2 Hz, 1H), 7.15 (s, 1H), 5.27 (s, 2H), 3.36 (s, 3H).

Step 4: Methyl 4-benzyloxy-5-bromine-2-methylbenzoate

To a 100 mL flask, 4-benzyloxy-5-bromine-2-methylbenzoic acid (4.3 g, 13.4 mmol) and methanol (30 mL) were added, then 10 drops of concentrated sulfuric acid were added as a catalyst. The reaction mixture was heated to 80° C. and refluxed overnight. The reaction mixture was cooled to room temperature, then the solvent was removed. The resulting residue was dissolved in ethyl acetate, the organic phase was washed successively with saturated sodium bicarbonate solution and saturated brine, and then dried over anhydrous sodium sulfate and concentrated to give a white solid. The solid was purified by flash column chromatography to give methyl 4-benzyloxy-5-bromine-2-methylbenzoate (3.4 g, white solid, yield: 75%).

$^1$H NMR (400 MHz, CDCl$_3$): δ 8.11 (s, 1H), 7.40 (d, J=7.0 Hz, 2H), 7.37-7.30 (m, 2H), 7.30-7.23 (m, 1H), 6.71 (s, 1H), 5.13 (s, 2H), 3.79 (d, J=3.1 Hz, 3H), 2.50 (s, 3H).

Step 5: 4-benzyloxy-5-bromine-2-methylbenzenemethanol

To a 50 mL flask, methyl 4-benzyloxy-5-bromine-2-methyl-benzoate (2.0 g, 6.0 mmol) was added, then dichloromethane (40 mL) was added as a solvent after purging with N$_2$. The reaction mixture was placed in a dry ice-acetone bath for 10 minutes, then diisobutylaluminium hydride (12 mL, 12 mmol) was slowly added. The reaction mixture was stirred for 1.5 hours, then methanol (5 mL) was added. The reaction mixture was stirred for 5 minutes, then a saturated solution of sodium tartrate was added. After the reaction mixture was stirred at room temperature for 0.5 hour, ethyl acetate and water were added. The organic phase was separated and washed with saturated brine, then dried and concentrated to give 4-benzyloxy-5-bromine-2-methylbenzenemethanol (1.88 g, a white solid, yield: nearly 100%).

$^1$H NMR (400 MHz, CDCl$_3$): δ 7.46 (s, 1H), 7.41 (d, J=7.3 Hz, 2H), 7.36-7.29 (m, 2H), 7.19 (s, 1H), 6.70 (s, 1H), 5.07 (s, 2H), 4.53 (s, 2H), 2.23 (s, 3H).

Step 6: 4-benzyloxy-5-bromine-2-methylbenzaldehyde

To a 100 mL flask, 4-benzyloxy-5-bromine-2-methylbenzenemethanol (1.88 g, 6 mmol) and 2-iodoxybenzoic acid (3.4 g, 12 mmol) were added, then dimethyl sulfoxide (20 mL) and tetrahydrofuran (20 mL) were added as a solvent. The reaction mixture was heated to 40° C. and stirred for 2 hours. Water and ethyl acetate were added, then the organic phase was separated and washed successively with water, saturated sodium bicarbonate solution and saturated brine, and then dried over anhydrous sodium sulfate and concentrated to give 4-benzyloxy-5-bromine-2-methylbenzaldehyde (1.82 g, a white solid, yield: nearly 100%).

$^1$H NMR (400 MHz, CDCl$_3$, ppm): δ 10.01 (s, 1H), 7.93 (s, 1H), 7.41 (d, J=6.9 Hz, 2H), 7.38-7.28 (m, 2H), 7.19 (s, 1H), 6.71 (s, 1H), 5.16 (s, 2H), 2.55 (s, 3H).

Step 7: (4-benzyloxy-5-bromine-2-methylphenyl)-(2,3-dihydrobenzo[b][1,4]dioxin-6-yl)-methanol To a 50 mL flask, fresh magnesium ribbon (100 mg, 4.2 mmol) was added, then tetrahydrofuran (4 mL) and a small amount of iodine were added after purging with $N_2$, and then a small amount of a solution of 6-bromine-2,3-dihydrobenzo[b][1,4]dioxine in tetrahydrofuran was added. The reaction mixture was heated to 40° C., then the remaining 6-bromo-2,3-dihydro-benzo[b][1,4]dioxine (645 mg, 3 mmol) was added dropwise after successfully initiating the reaction. The reaction mixture was stirred for about 40 minutes, then a solution of 4-benzyloxy-5-bromine-2-methylbenzaldehyde (305 mg, 1 mmol) in tetrahydrofuran was added in an ice bath. The reaction mixture was stirred for 3 hours, then inorganic substance was filtered off through short column of silica gel, and then the filtrate was concentrated. The resulting residue was purified by flash column chromatography to give (4-benzyloxy-5-bromine-2-methylphenyl)-(2,3-dihydrobenzo[b][1,4]dioxin-6-yl)-methanol (430 mg, an oil, yield: nearly 97%).

$^1$H NMR (400 MHz, $CDCl_3$): δ 7.73 (s, 1H), 7.48 (d, J=7.1 Hz, 2H), 7.39 (dd, J=10.0, 4.7 Hz, 2H), 7.32 (t, J=7.3 Hz, 1H), 6.85-6.74 (m, 3H), 6.72 (d, J=5.6 Hz, 1H), 5.79 (s, 1H), 5.14 (d, J=7.5 Hz, 2H), 4.24 (s, 4H), 2.15 (s, 3H).

Step 8: 6-(4-benzyloxy-5-bromine-2-methylbenzyl)-2,3-dihydrobenzo[b][1,4]dioxine (4-benzyloxy-5-bromine-2-methylphenyl)-(2,3-dihydrobenzo[b][1,4]dioxin-6-yl)-methanol (430 mg, 0.98 mmol) was dissolved in a mixed solvent of dichloromethane (8 mL) and acetonitrile (7 mL), then triethylsilane (1 mL, 6.26 mmol) and boron trifluoride etherate (0.6 mL, 4.75 mmol) were added successively in an ice bath after purging with $N_2$. The reaction mixture was naturally warmed up to room temperature, and the color of the reaction system slowly became light. After the reaction mixture was stirred for 2 hours, the solvent and excess triethylsilane was removed. The crude product was purified by column chromatography (12% ethyl acetate) to give 6-(4-benzyloxy-5-bromine-2-methylbenzyl)-2,3-dihydrobenzo[b][1,4]dioxine (200 mg, a white solid, yield: nearly 48%).

$^1$H NMR (400 MHz, $CDCl_3$): δ 7.48 (d, J=7.2 Hz, 2H), 7.39 (dd, J=10.1, 4.7 Hz, 2H), 7.31 (dd, J=13.4, 6.1 Hz, 1H), 7.27 (d, J=6.1 Hz, 1H), 6.80-6.73 (m, 2H), 6.59 (dd, J=5.6, 2.1 Hz, 2H), 5.12 (s, 2H), 4.23 (s, 4H), 3.77 (s, 2H), 2.17 (s, 3H).

Step 9: (3R,4S,5S,6R)-3,4,5-tribenzyl oxy-2-[2-benzyloxy-5-(2,3-dihydrobenzo[b][1,4]dioxin-6-yl)methyl-4-methylphenyl]-6-benzyloxymethyltetrahydrothiopyran-2-ol To a 50 mL flask, 6-(4-benzyloxy-5-bromine-2-methylbenzyl)-2,3-dihydrobenzo[b][1,4]dioxine (400 mg, 0.94 mmol) was added, then THF (4 mL) and toluene (4 mL) were added as a solvent after purging with $N_2$. The reaction mixture was placed in a dry ice-acetone bath for 5 minutes, then n-BuLi (0.75 mL, 1.5 mmol) was slowly added. After the reaction mixture was stirred for 0.5 hour, a solution of (3R,4S,5S,6R)-3,4,5-tribenzyloxy-6-benzyloxymethyltetrahydrothiopyran-2-one (573 mg, 1.03 mmol) in tetrahydrofuran was added. After the reaction mixture was stirred for another 2 hours, the solvent was removed. The resulting residue was purified by flash column chromatography to give (3R,4S,5S,6R)-3,4,5-tribenzyloxy-2-[2-benzyloxy-5-(2,3-dihydrobenzo[b][1,4]dioxin-6-yl)methyl-4-methylphenyl]-6-benzyloxymethyltetrahydrothiopyran-2-ol (210 mg, a foamy solid, yield: 25%).

Step 10: 6-[4-benzyloxy-2-methyl-5-((2S,3R,4R,5S,6R)-3,4,5-tribenzyloxy-6-benzyloxymethyltetrahydrothiopyran-2-yl)benzyl]-2,3-dihydrobenzo[b][1,4]dioxine To a 50 mL flask, (3R,4S,5 S, 6R)-3,4,5-tribenzyloxy-2-[2-benzyloxy-5-(2,3-dihydrobenzo[b][1,4]dioxin-6-yl)methyl-4-methylphenyl]-6-benzyloxymethyltetrahydrothiopyran-2-ol (210 mg, 0.23 mmol) was added, then dichloromethane (7 mL) and acetonitrile (5 mL) were added as a solvent after purging with $N_2$. The reaction mixture was placed in an ice bath for 10 mintures, then triethylsilane (1 mL, 6.26 mmol) and boron trifluoride etherate (0.6 mL, 4.75 mmol) were added. After the reaction mixture was stirred for another 3 hours, a saturated sodium bicarbonate solution was added to quench the reaction. The organic phase was separated, and the aqueous phase was extracted with ethyl acetate (50 mL×2). The organic phases were combined, then dried and concentrated. The resulting residue was purified by flash column chromatography (10% ethyl acetate) to give 6-[4-benzyloxy-2-methyl-5-((2S,3R,4R,5S,6R)-3,4,5-tribenzyloxy-6-benzyloxymethyltetrahydrothiopyran-2-yl)benzyl]-2,3-dihydrobenzo[b][1,4]dioxine (100 mg, an oil, yield: 48%).

Step 11: (2S,3R,4R,5S,6R)-2-(5-((2,3-dihydrobenzo[b][1,4]dioxin-6-yl)methyl)-2-hydroxy-4-methylphenyl)-6-(hydroxymethyl)tetrahydro-2H-thiopyran-3,4,5-triol To a 50 mL flask, 6-[4-benzyloxy-2-methyl-5-((2S,3R,4R,5S,6R)-3,4,5-tribenzyloxy-6-benzyloxymethyltetrahydrothiopyran-2-yl)benzyl]-2,3-dihydrobenzo[b][1,4]dioxine (98 mg, 0.11 mmol) and pentamethylbenzene (297 mg, 2 mmol) were added, then dichloromethane (8 mL) was added as a solvent after purging with $N_2$. The reaction mixture was placed in a dry ice-acetone bath for 10 minutes, then boron trichloride (1 mL, 1 mmol) was slowly added. After the reaction mixture was stirred for 3 hours, the reaction was quenched with anhydrous methanol, and the color of the reaction system became yellow. The reaction mixture was stirred for another 0.5 hour, then the solvent was removed. The resulting residue was purified by reverse phase column chromatography to give (2S,3R,4R,5S,6R)-2-(5-((2,3-dihydrobenzo[b][1,4]dioxin-6-yl)methyl)-2-hydroxy-4-methylphenyl)-6-(hydroxymethyl)tetrahydro-2H-thiopyran-3,4,5-triol (15 mg, an oil, yield: 31%).

MS m/z (ESI): 416.9.

$^1$H NMR (400 MHz, MeOD, ppm): δ 7.06 (s, 1H), 6.69 (d, J=8.1 Hz, 1H), 6.64 (s, 1H), 6.59-6.51 (m, 2H), 4.31 (t, J=13.5 Hz, 1H), 4.18 (s, 4H), 4.02-3.93 (m, 1H), 3.93-3.84 (m, 1H), 3.77 (q, J=6.4 Hz, 3H), 3.64 (t, J=9.6 Hz, 1H), 3.36-3.27 (m, 1H), 3.02 (ddd, J=10.1, 6.3, 3.8 Hz, 1H), 2.09 (s, 3H).

Example 7: (1S,2S,3S,4R,5S)-5-(3-((2,3-dihydrobenzo[b][1,4]dioxin-6-yl)methyl)-4-propylphenyl)-1-(hydroxymethyl)-6,8-dioxabicyclo[3.2.1]octane-2,3,4-triol

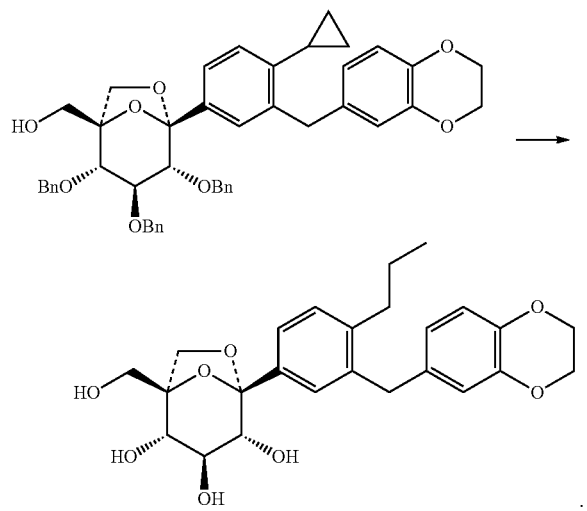

{(3S,4S,5R)-3,4,5-tribenzyloxy-6-[4-cyclopropyl-3-(2,3-dihydrobenzo[b][1,4]dioxin-6-ylmethyl)phenyl]-2-hydroxymethyl-6-methoxytetrahydropyran-2-yl}-methanol (256 mg, 0.34 mmol) was dissolved in a mixed solvent of tetrahydrofuran (5 mL) and methanol (20 mL) (v:v=1:10), then 10% Pd/C (50 mg) was added, and then the reaction mixture was purged with hydrogen three times. The reaction mixture was stirred at room temperature for 4 hours, then filtered. Then, the filtrate was concentrated under reduced pressure. The resulting residue was purified by column chromatography to give the title product (93 mg, a white solid, yield: 60%).

MS m/z (ESI): 459.2 [M+1].

$^1$H NMR (400 MHz, MeOD) δ 7.41-7.34 (m, 2H), 7.16 (d, J=8.6 Hz, 1H), 6.70 (d, J=8.2 Hz, 1H), 6.61-6.53 (m, 2H), 4.18 (d, J=5.3 Hz, 5H), 3.91 (s, 2H), 3.84 (dd, J=14.3, 10.3 Hz, 2H), 3.75-3.59 (m, 4H), 2.60-2.49 (m, 2H), 1.47 (dd, J=15.4, 7.5 Hz, 2H), 0.91 (t, J=7.3 Hz, 3H).

Example 8: (1S,2S,3S,4R,5S)-5-(3-((2,3-dihydrobenzo[b][1,4]dioxin-6-yl)methyl)-4-methylphenyl)-1-(hydroxymethyl)-6,8-dioxabicyclo[3.2.1]octane-2,3,4-triol

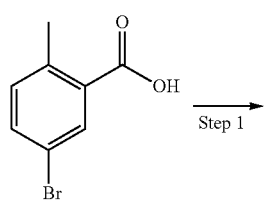

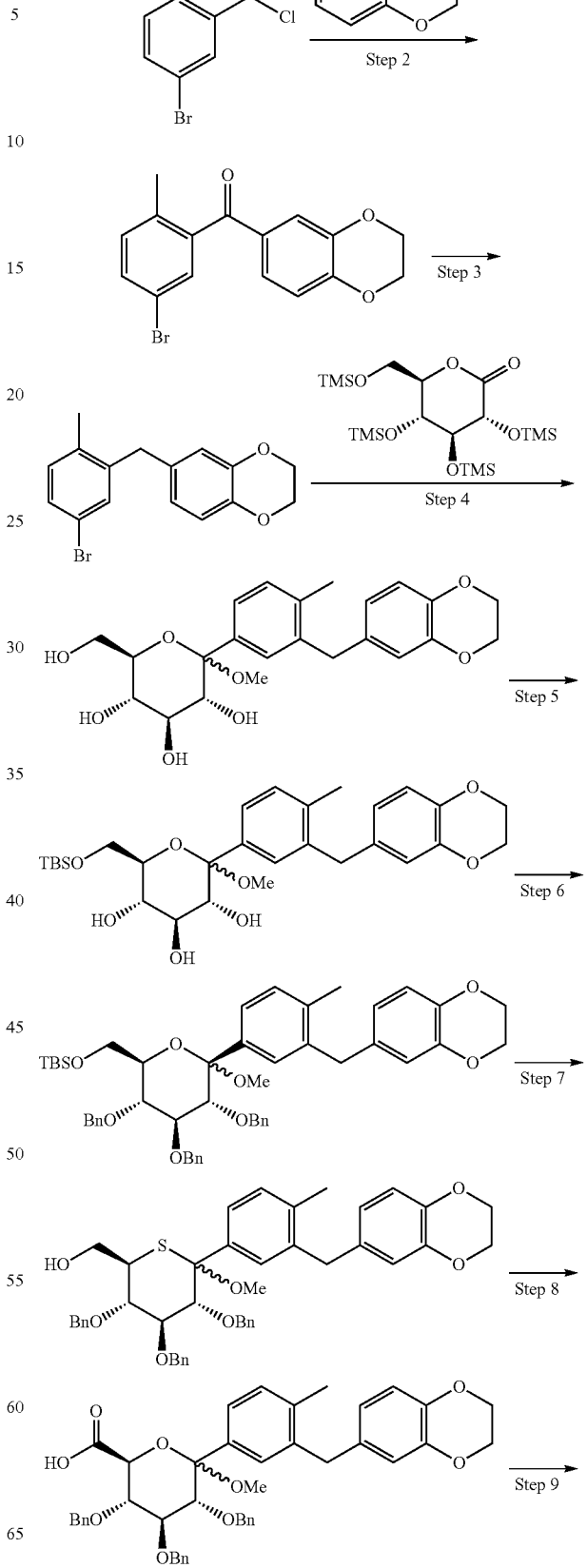

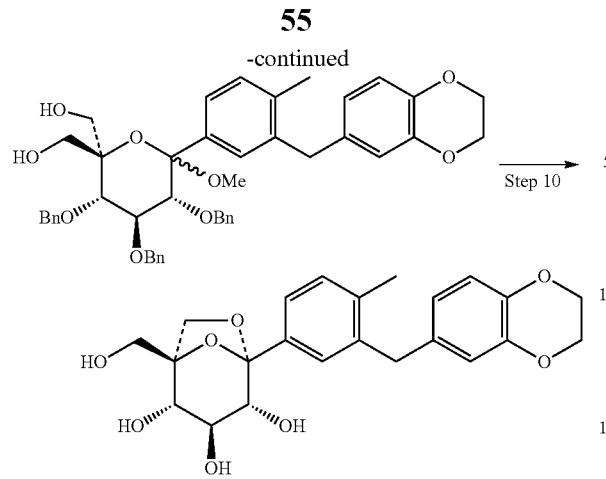

Step 1: 5-bromo-2-methylbenzoyl chloride

To a 50 mL flask, 5-bromo-2-methylbenzoic acid (4.3 g, 20 mmol) was added, then anhydrous dichloromethane (30 mL) was added after purging with $N_2$. The reaction mixture was cooled to 0° C., then a catalytic amount of DMF (0.5 mL) was added, and then oxalyl chloride (5 mL, 58 mmol) was slowly added. The reaction mixture was warmed up to room temperature and stirred for 3 hours until the reaction solution became a clear solution, and then the stirring was stopped. Dichloromethane and excess oxalyl chloride were removed by rotary evaporation to give a pale yellow oil (4.8 g, 100.0%), which was used directly in the next step.

Step 2: (5-bromo-2-methylphenyl)-(2,3-dihydrobenzo[b][1,4]dioxin-6-yl)methanone

The crude product obtained above was dissolved in anhydrous dichloromethane (120 mL) after purging with $N_2$, then benzodioxine (2.72 g, 20 mmol) was added. The reaction mixture was cooled to 0° C., then $AlCl_3$ (3.5 g, 26 mmol) was added in batches. The reaction mixture was slowly warmed up to room temperature and stirred overnight. The reaction mixture was poured into ice and extracted with dichloromethane (150 ml×3). The reaction solvent was removed by rotary evaporation to give a white solid (6.4 g, yield: 96.0%), which was used directly in the next step.

Step 3: 6-(5-bromo-2-methylbenzyl)-2,3-dihydrobenzo[b][1,4]dioxine (5-bromo-2-methylphenyl)-(2,3-dihydrobenzo[b][1,4]dioxin-6-yl)methanone (6.4 g, 19.2 mmol) was dissolved in acetonitrile (100 mL). The reaction mixture was cooled to 0° C., then triethylsilane (11.0 mL, 67.2 mmol) was added, and then boron trifluoride etherate (7.5 mL, 58 mmol) was slowly added. The reaction mixture was stirred at room temperature overnight. The reaction was quenched with a saturated solution of $NaHCO_3$, then the reaction mixture was extracted with ethyl acetate (100 mL×3). Then, the solvent was removed by rotary evaporation. The resulting residue was purified by column chromatography to give the title product (5.6 g, yield: 92.0%).

$^1$H NMR (400 MHz, $CDCl_3$) δ 7.23 (dd, J=9.7, 2.1 Hz, 2H), 7.01 (d, J=8.0 Hz, 1H), 6.78 (d, J=8.8 Hz, 1H), 6.59 (dt, J=3.9, 2.0 Hz, 2H), 4.23 (s, 4H), 3.82 (s, 2H), 2.18 (s, 3H).

Step 4: (3R,4S,5S,6R)-2-(3-((2,3-dihydrobenzo[b][1,4]dioxin-6-yl)methyl)-4-methylphenyl)-6-(hydroxymethyl)-2-methoxytetrahydro-2H-pyran-3,4,5-triol 6-(5-bromo-2-methylbenzyl)-2,3-dihydrobenzo[b][1,4]dioxine (5.5 g, 17.2 mmol) was dissolved in a mixed solvent of THF (20 mL) and toluene (20 mL). The reaction mixture was placed in a dry ice-acetone bath, then n-BuLi in n-hexane (1.6M, 20 mL, 31 mmol) was slowly added. After the reaction mixture was stirred at this temperature for 1 hour, a solution of (3R,4S,5R,6R)-3,4,5-tris(trimethylsilyloxy)-6-trimethylsilyloxymethyltetrahydropyran-2-one (8 g, 17.2 mmol) in toluene (10 mL) was added. The reaction mixture was stirred at −70° C. for 2 hours, then a solution of MsOH (4.5 g, 46.8 mmol) in methanol was added, and then naturally warmed up to room temperature and stirred overnight. A saturated sodium bicarbonate solution was added, the aqueous phase was extracted with EtOAc, the organic phase was washed three times with saturated brine, and then dried over anhydrous sodium sulfate and concentrated. The resulting residue was purified by column chromatography to give a pale yellow foamy solid. (3.8 g, yield: 52.0%).

$^1$H NMR (400 MHz, $CDCl_3$) δ 7.26-7.21 (m, 2H), 7.07 (d, J=7.9 Hz, 1H), 6.72 (d, J=8.2 Hz, 1H), 6.55 (dd, J=12.3, 3.9 Hz, 2H), 5.30 (s, 1H), 4.16 (d, J=11.3 Hz, 4H), 3.96-3.80 (m, 5H), 3.63 (s, 2H), 3.27 (d, J=9.1 Hz, 1H), 3.04 (s, 3H), 2.17 (s, 3H).

Step 5: (3R,4S,5S,6R)-6-(((tert-butyldimethylsilyl)oxy)methyl)-2-(3-((2,3-dihydrobenzo[b][1,4]dioxin-6-yl)methyl)-4-methylphenyl)-2-methoxytetrahydro-2H-pyran-3,4,5-triol (3R,4S,5S,6R)-2-(3-((2,3-dihydrobenzo[b][1,4]dioxin-6-yl)methyl)-4-methylphenyl)-6-(hydroxymethyl)-2-methoxytetrahydro-2H-pyran-3,4,5-triol (3.8 g, 8.7 mmol) was dissolved in dichloromethane (30 mL), then imidazole (1.8 g, 26.4 mmol) and DMAP (106.3 mg, 0.87 mmol) were added, and then TBSCl (1.46 g, 9.7 mmol) was added in batches under $N_2$. The reaction mixture was stirred at room temperature overnight. A saturated aqueous ammonium chloride solution was added, the organic phase was separated and washed with saturated brine, and then dried over anhydrous sodium sulfate and concentrated to give a pale yellow foamy solid (4.2 g, yield: 88.0%).

Step 6: tert-butyldimethyl(((2R,3R,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2-yl)methoxy)silane (3R,4S,5S,6R)-6-(((tert-butyldimethylsilyl)oxy)methyl)-2-(3-((2,3-dihydrobenzo[b][1,4]dioxin-6-yl)methyl)-4-methylphenyl)-2-methoxytetrahydro-2H-pyran-3,4,5-triol (4.2 g, 7.7 mmol) was dissolved in a mixed solvent of THF (36 mL) and DMF (12 mL). The reaction mixture was placed in an ice-water bath, then NaH (60%, 1.54 g, 38.4 mmol) was added in batches under $N_2$. The reaction mixture was warmed up to room temperature and stirred for 30 minutes, then BnBr (7.23 g, 42.3 mmol) was added dropwise in an ice-water bath. The reaction mixture was warmed up to room temperature and stirred overnight. A saturated aqueous ammonium chloride solution and EtOAc was added, the organic phase was separated and washed successively with water and saturated brine, and then dried over anhydrous sodium sulfate and concentrated. The resulting residue was purified by column chromatography to give a white solid (3.9 g, yield: 63%).

Step 7: ((2R,3R,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2-yl)methanol Tert-butyldimethyl(((2R,3R,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2-yl)methoxy)silane (3.9 g, 4.8 mmol) was dissolved in methanol (30 mL), then AcCl (21 mg, 0.15 mmol)) was added in an ice-water bath. The reaction mixture was naturally warmed up to room temperature and stirred for 1 hour, then concentrated under reduced pressure to give a white foamy solid (3.2 g, yield: 95.0%).

Step 8: (2S,3S,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2-carbaldehyde Oxalyl chloride (762 mg, 6 mmol) was dissolved in DCM (10 mL) at room temperature. The reaction mixture was placed in a dry ice-acetone bath, a solution of DMSO (625 mg, 8 mmol) in DCM (10 mL) was added dropwise, and the temperature was controlled at about −70° C. The reaction mixture was stirred for 25 minutes, then a solution of ((2R,3R,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2-yl)methan of (1.4 g, 2.0 mmol) in DCM (5 mL) was added. The reaction mixture was stirred at −70° C. for 1 hour, then triethylamine (2 g, 20 mmol) was added dropwise. The reaction mixture was stirred at room temperature for 30 minutes, then 1M hydrochloric acid was added in an ice-water bath. The mixture was extracted with DCM, the organic phase was washed twice with saturated brine, and then dried over anhydrous sodium sulfate and concentrated to give a white foamy solid (1.4 g, yield: 98%), which was used directly in the next step.

Step 9: ((3S,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2,2-diyl)dimethanol (2S,3S,4S,5R)-3,4,5-tris(benzyloxy)-6-(3-((2,3-dihydrobenzo[1,4]dioxin-6-yl)methyl)-4-methylphenyl)-6-methoxytetrahydro-2H-pyran-2-carbaldehyde (1.4 g, 2.0 mmol) was dissolved in 1,4-dioxane (30 mL), then paraformaldehyde solution (300 mg, 10 mmol) and potassium hydroxide (504 mg, 9 mmol) were added under $N_2$. The reaction mixture was heated to 50° C. and stirred for 2 hours. The reaction solution was left to stand overnight, then filtered, and then the filtrate was concentrated below 50° C. The resulting residue was dissolved in dichloromethane (200 mL) and washed with saturated brine (100 mL×2), and then dried over anhydrous sodium sulfate and filtered. The filtrate was concentrated. The resulting residue was purified by column chromatography to give the title product (130 mg, a yellow oil, yield: 9.0%).

Step 10: (1S,2S,3S,4R,5S)-5-(3-((2,3-dihydrobenzo[b][1,4]dioxin-6-yl)methyl)-4-methylphenyl)-1-(hydroxymethyl)-6, 8-dioxabicyclo[3.2.1]octane-2,3,4-triol ((3S,4S,5R)-3,4,5-tris(benzyloxy)-6-(3-((2,3-dihydrobenzo[b][1,4]dioxin-6-yl)methyl)-4-methylphenyl)-6-methoxytetrahydro-2H-pyran-2,2-diyl)dimethanol (74 mg, 0.1 mmol) was dissolved in a mixed solvent of tetrahydrofuran (3 mL) and methanol (30 mL) (v:v=1:10), then 10% Pd/C (50 mg) was added. The reaction mixture was purged with hydrogen three times and stirred at room temperature for 3 hours. The reaction mixture was filtered, then the filtrate was concentrated under reduced pressure. The resulting residue was purified by column chromatography to give the title product (40 mg, a white solid, yield: 93%).

MS m/z (ESI): 431.2 [M+1].

$^1$H NMR (400 MHz, MeOD) δ 7.36 (dd, J=9.1, 4.6 Hz, 2H), 7.14 (d, J=7.8 Hz, 1H), 6.70 (d, J=8.2 Hz, 1H), 6.61-6.54 (m, 2H), 4.18 (s, 5H), 3.89 (s, 2H), 3.84 (dd, J=15.6, 10.3 Hz, 2H), 3.67 (ddd, J=16.1, 10.1, 2.4 Hz, 4H), 2.20 (s, 3H).

Example 9: (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol

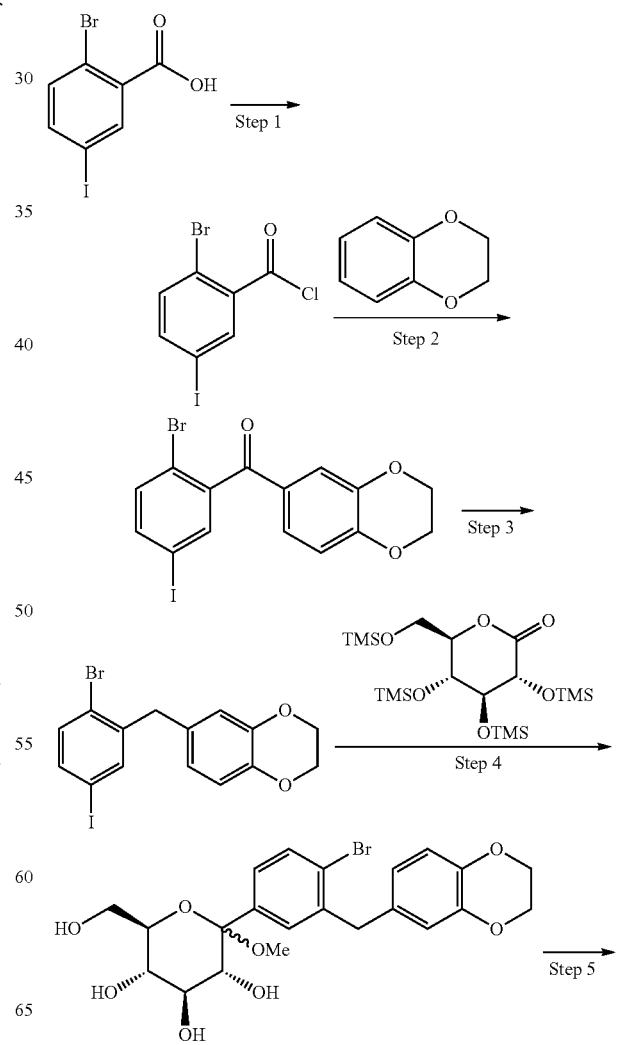

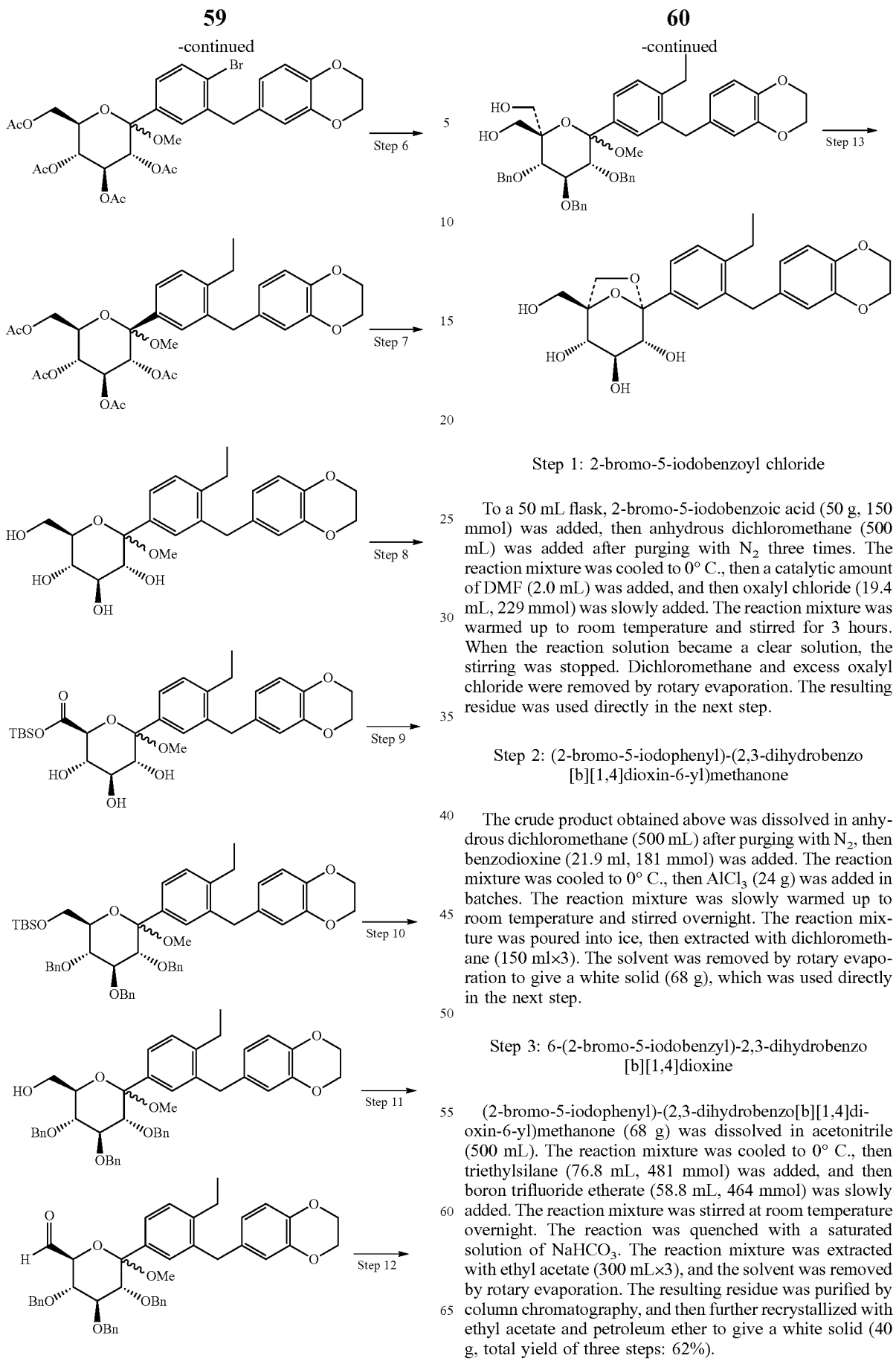

Step 1: 2-bromo-5-iodobenzoyl chloride

To a 50 mL flask, 2-bromo-5-iodobenzoic acid (50 g, 150 mmol) was added, then anhydrous dichloromethane (500 mL) was added after purging with $N_2$ three times. The reaction mixture was cooled to 0° C., then a catalytic amount of DMF (2.0 mL) was added, and then oxalyl chloride (19.4 mL, 229 mmol) was slowly added. The reaction mixture was warmed up to room temperature and stirred for 3 hours. When the reaction solution became a clear solution, the stirring was stopped. Dichloromethane and excess oxalyl chloride were removed by rotary evaporation. The resulting residue was used directly in the next step.

Step 2: (2-bromo-5-iodophenyl)-(2,3-dihydrobenzo [b][1,4]dioxin-6-yl)methanone

The crude product obtained above was dissolved in anhydrous dichloromethane (500 mL) after purging with $N_2$, then benzodioxine (21.9 ml, 181 mmol) was added. The reaction mixture was cooled to 0° C., then $AlCl_3$ (24 g) was added in batches. The reaction mixture was slowly warmed up to room temperature and stirred overnight. The reaction mixture was poured into ice, then extracted with dichloromethane (150 ml×3). The solvent was removed by rotary evaporation to give a white solid (68 g), which was used directly in the next step.

Step 3: 6-(2-bromo-5-iodobenzyl)-2,3-dihydrobenzo [b][1,4]dioxine (2-bromo-5-iodophenyl)-(2,3-dihydrobenzo[b][1,4]dioxin-6-yl)methanone (68 g) was dissolved in acetonitrile (500 mL). The reaction mixture was cooled to 0° C., then triethylsilane (76.8 mL, 481 mmol) was added, and then boron trifluoride etherate (58.8 mL, 464 mmol) was slowly added. The reaction mixture was stirred at room temperature overnight. The reaction was quenched with a saturated solution of $NaHCO_3$. The reaction mixture was extracted with ethyl acetate (300 mL×3), and the solvent was removed by rotary evaporation. The resulting residue was purified by column chromatography, and then further recrystallized with ethyl acetate and petroleum ether to give a white solid (40 g, total yield of three steps: 62%).

¹H NMR (400 MHz, CDCl₃) δ 7.43 (d, J=2.2 Hz, 1H), 7.37 (dd, J=8.3, 2.2 Hz, 1H), 7.24 (d, J=2.7 Hz, 1H), 6.82-6.76 (m, 1H), 6.69-6.61 (m, 2H), 4.23 (s, 4H), 3.92 (s, 2H).

Step 4: (3R,4S,5S,6R)-2-(4-bromo-3-((2,3-dihydrobenzo[b][1,4]dioxin-6-yl)meth yl)phenyl)-6-(hydroxymethyl)-2-methoxytetrahydro-2H-pyran-3,4,5-triol 6-(2-bromo-5-iodobenzyl)-2,3-dihydrobenzo[b][1,4]dioxine (5 g, 11.6 mmol) was dissolved in a mixed solvent of THF (20 mL) and toluene (20 mL). The reaction mixture was placed in a dry ice-acetone bath, then n-BuLi in n-hexane (1.6M, 11 mL, 17.6 mmoL) was slowly added. After the reaction mixture was stirred at this temperature for 1 hour, a solution of (3R,4S,5R,6R)-3,4,5-tris(trimethylsilyloxy)-6-trimethylsilyloxymethyltetrahydropyran-2-one (6 g, 12.8 mmol) in toluene (10 mL) was added. The reaction mixture was stirred at −70° C. for 2 hours, and a solution of MsOH (2.7 g, 27.8 mmol) in methanol (5 mL) was added. The reaction mixture was naturally warmed up to room temperature and stirred overnight. A saturated sodium bicarbonate solution was added, the aqueous phase was extracted with EtOAc, the organic phase was washed three times with saturated brine, and then dried over anhydrous sodium sulfate and concentrated. The resulting residue was purified by column chromatography to give a pale yellow foamy solid (2.52 g, yield: 43.7%).
¹H NMR (400 MHz, CDCl₃) δ 7.47 (d, J=8.3 Hz, 1H), 7.34 (t, J=11.0 Hz, 1H), 7.18 (d, J=8.2 Hz, 1H), 6.75 (d, J=8.1 Hz, 1H), 6.65 (dd, J=10.5, 2.1 Hz, 2H), 4.17 (d, J=30.4 Hz, 4H), 4.06-3.78 (m, 5H), 3.62 (dt, J=19.7, 9.4 Hz, 2H), 3.23 (d, J=9.3 Hz, 1H), 2.97 (s, 3H).

Step 5: (3R,4S,5R,6R)-6-(acetoxymethyl)-2-(4-bromo-3-((2,3-dihydrobenzo[b][1,4]dioxin-6-yl)methyl)phenyl)-2-methoxytetrahydro-2H-pyran-3,4,5-triyl triacetate (3R,4S,5S,6R)-2-(4-bromo-3-((2,3-dihydrobenzo[b][1,4]dioxin-6-yl)methyl)phenyl)-6-(hydroxymethyl)-2-methoxytetrahydro-2H-pyran-3,4,5-triol (2.5 g, 5 mmol) was dissolved in dichloromethane (20 mL), then pyridine (3.2 g, 40 mmol), Ac₂O (4.1 g, 40 mmol) and DMAP (61 mg, 0.5 mmol) were successively added. The reaction mixture was stirred at room temperature for 2 hours. The solvent was removed under reduced pressure. The resulting residue was dissolved in EtOAc, and washed twice with 1M hydrochloric acid, then washed with saturated brine, and then dried over anhydrous sodium sulfate and concentrated to give a yellow foamy solid (2.9 g, yield: 87.2%).
¹H NMR (400 MHz, CDCl₃) δ 7.48 (dd, J=14.0, 7.3 Hz, 1H), 7.17-7.06 (m, 2H), 6.71 (d, J=8.2 Hz, 1H), 6.63-6.45 (m, 2H), 5.49 (t, J=9.7 Hz, 1H), 5.15 (t, J=9.8 Hz, 1H), 4.87 (d, J=10.0 Hz, 1H), 4.27 (dd, J=12.2, 5.0 Hz, 1H), 4.20-4.10 (m, 5H), 3.02 (s, 3H), 2.04 (s, 3H), 1.98 (d, J=2.8 Hz, 3H), 1.89 (d, J=8.3 Hz, 3H), 1.75 (s, 3H).

Step 6: (3R,4S,5R,6R)-6-(acetoxymethyl)-2-(3-((2,3-dihydrobenzo[b][1,4]dioxin-6-yl)methyl)-4-ethylphenyl)-2-methoxytetrahydro-2H-pyran-3,4,5-triyl triacetate (3R,4S,5R,6R)-6-(acetoxymethyl)-2-(4-bromo-3-((2,3-dihydrobenzo[b][1,4]dioxin-6-yl)methyl)phenyl)-2-methoxytetrahydro-2H-pyran-3,4,5-triyl triacetate (3.0 g, 4.51 mmol), ethylboronic acid (666 mg, 9.01 mmol), palladium acetate (202 mg, 0.902 mmol) and K₃PO₄ (3.35 g, 15.79 mmol) were dissolved in a mixed solvent of toluene (50 mL) and water (10 mL). The reaction mixture was purged with N₂ for 15 minutes, then PCy₃ (505 mg, 1.8 mmol) was added, and then N₂ was sequentially purged for 30 minutes. The reaction mixture was heated to 100° C. and reacted in a sealed tube for 6 hours, then cooled, diluted with EtOAc, washed successively with water and saturated brine, and then dried over anhydrous sodium sulfate and concentrated. The resulting residue was purified by column chromatography to give a white foamy solid (2.5 g, yield: 90%).
¹H NMR (400 MHz, CDCl₃) δ 7.30 (dd, J=8.0, 1.7 Hz, 1H), 7.20 (d, J=8.0 Hz, 1H), 7.15 (d, J=1.5 Hz, 1H), 6.75 (d, J=8.1 Hz, 1H), 6.56-6.47 (m, 2H), 5.58 (t, J=9.7 Hz, 1H), 5.23 (t, J=9.8 Hz, 1H), 4.98 (d, J=10.0 Hz, 1H), 4.35 (dd, J=12.2, 4.9 Hz, 1H), 4.28-4.18 (m, 5H), 4.04 (ddd, J=10.2, 4.8, 2.4 Hz, 1H), 3.91 (d, J=16.5 Hz, 2H), 3.13 (s, 3H), 2.57 (q, J=7.5 Hz, 2H), 2.11 (s, 3H), 2.06 (s, 3H), 1.95 (s, 3H), 1.84 (s, 3H), 1.14 (t, J=7.5 Hz, 3H).

Step 7: (3R,4S,5S,6R)-2-(3-((2,3-dihydrobenzo[b][1,4]dioxin-6-yl)methyl)-4-ethylphenyl)-6-(hydroxymethyl)-2-methoxytetrahydro-2H-pyran-3,4,5-triol (3R,4S,5R,6R)-6-(acetoxymethyl)-2-(3-((2,3-dihydrobenzo[b][1,4]dioxin-6-yl)methyl)-4-ethylphenyl)-2-methoxytetrahydro-2H-pyran-3,4,5-triyl triacetate (2.88 g, 4.7 mmol) was dissolved in a mixed solvent of THF (15 mL), methanol (10 mL) and water (5 mL), then LiOH.H₂O (236 mg, 5.6 mmol) was added. The reaction mixture was stirred at room temperature for 2 hours. The organic solvent was removed under reduced pressure. The resulting residue was dissolved in EtOAc, washed successively with 5% NaHSO₄ aqueous solution and saturated brine, and then dried over anhydrous sodium sulfate and concentrated to give a white foamy solid (2.0 g, yield: 95%).

Step 8: (3R,4S,5S,6R)-6-(((tert-butyldimethylsilyl)oxy)methyl)-2-(3-((2,3-dihydrobenzo[b][1,4]dioxin-6-yl)methyl)-4-ethylphenyl)-2-methoxytetrahydro-2H-pyran-3,4,5-triol (3R,4S,5S,6R)-2-(3-((2,3-dihydrobenzo[b][1,4]dioxin-6-yl)methyl)-4-ethylphenyl)-6-(hydroxymethyl)-2-methoxytetrahydro-2H-pyran-3,4,5-triol (2.0 g, 4.48 mmol) was dissolved in dichloromethane (30 mL), then imidazole (915 mg, 13.44 mmol) and DMAP (55 mg, 0.45 mmol) were added, and then TBSCl (743 mg, 4.93 mmol) was added in batches under N₂. The reaction mixture was stirred at room temperature overnight. A saturated ammonium chloride aqueous solution was added, the organic phase was separated and washed with saturated brine, then dried over anhydrous sodium sulfate and concentrated to give a pale yellow foamy solid (2.5 g, yield: 98%).
¹H NMR (400 MHz, CDCl₃) δ 7.24-7.17 (m, 2H), 7.07 (dd, J=5.5, 2.4 Hz, 1H), 6.45 (dd, J=4.2, 2.4 Hz, 2H), 4.08 (s, 4H), 3.88-3.77 (m, 5H), 3.62-3.50 (m, 2H), 3.16 (d, J=9.3 Hz, 2H), 2.99 (ddd, J=8.9, 4.1, 1.7 Hz, 4H), 2.46 (q, J=7.5 Hz, 2H), 1.01 (t, J=7.5 Hz, 3H), 0.02-0.04 (m, 6H).

Step 9: Tert-butyldimethyl(42R,3R,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2-yl)methoxy)silane (3R,4S,5S,6R)-6-(((tert-butyldimethylsilyl)oxy)methyl)-2-(3-((2,3-dihydrobenzo[b][1,4]dioxin-6-yl)methyl)-4-ethylphenyl)-2-methoxytetrahydro-2H-pyran-3,4,5-triol (2.5 g, 4.5 mmol) was dissolved in a mixed solvent of THF (15 mL) and DMF (5 mL). The reaction mixture was placed in an ice-water bath, then NaH (60%, 802 mg, 20.06 mmol) was added in batches. The reaction mixture was warmed up to room temperature and stirred for 30 minutes, then BnBr (7.23 g, 42.3 mmol) was added dropwise in an ice-water bath. The reaction mixture was warmed up to room temperature and stirred overnight. A saturated ammonium chloride aqueous solution and EtOAc were added, the organic phase was separated and washed successively with water and saturated brine, then dried over anhydrous sodium sulfate and concentrated. The resulting residue was purified by column chromatography to give a white viscous substance (2.9 g, yield: 79%).

$^1$H NMR (400 MHz, CDCl$_3$) δ 7.36-7.30 (m, 2H), 7.23-7.14 (m, 10H), 7.10 (dd, J=4.4, 2.3 Hz, 4H), 6.96 (dd, J=6.6, 2.9 Hz, 2H), 6.60 (d, J=8.1 Hz, 1H), 6.48-6.41 (m, 2H), 4.86-4.78 (m, 3H), 4.65 (d, J=10.7 Hz, 1H), 4.33 (d, J=10.3 Hz, 1H), 4.13-4.05 (m, 5H), 3.90-3.70 (m, 6H), 3.63-3.54 (m, 1H), 3.25 (d, J=9.6 Hz, 1H), 3.03 (d, J=3.7 Hz, 3H), 2.51 (ddd, J=14.8, 7.4, 3.9 Hz, 2H), 1.06 (t, J=7.5 Hz, 3H), 0.86-0.83 (m, 9H), 0.04 (s, 3H), 0.00 (s, 3H).

Step 10: ((2R,3R,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2-yl)methanol Tert-butyldimethyl(((2R,3R,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2-yl)methoxy)silane (1.5 g, 1.81 mmol) was dissolved in methanol (15 mL), then AcCl (21 mg, 0.15 mmol)) was added in an ice-water bath. The reaction mixture was naturally warmed up to room temperature and stirred for 1 hour, then concentrated under reduced pressure to give a yellow foamy solid (1.2 g, yield: 93%).

$^1$H NMR (400 MHz, CDCl$_3$) δ 7.38-7.28 (m, 12H), 7.18 (dd, J=6.7, 3.6 Hz, 4H), 7.06-6.99 (m, 2H), 6.72 (d, J=8.1 Hz, 1H), 6.58-6.51 (m, 2H), 4.99-4.82 (m, 3H), 4.69 (d, J=10.7 Hz, 1H), 4.39 (d, J=10.3 Hz, 1H), 4.23-4.16 (m, 5H), 3.99-3.64 (m, 8H), 3.35 (d, J=9.5 Hz, 1H), 3.14 (s, 3H), 2.67-2.55 (m, 2H), 1.17 (t, J=7.5 Hz, 3H).

Step 11: (2S,3S,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2-carbaldehyde Oxalyl chloride (318 mg, 2.51 mmol) was dissolved in DCM (15 mL) at room temperature. The reaction mixture was placed in a dry ice-acetone bath, then a solution of DMSO (260 mg, 3.34 mmol) in DCM (5 mL) was added dropwise, and the temperature was controlled at about −70° C. The reaction mixture was stirred for 25 minutes, then a solution of ((2R,3R,4S,5R)-3,4,5-tris(benzyloxy)-6-(3-((2,3-dihydrobenzo[b][1,4]dioxin-6-yl)meth yl)-4-ethylphenyl)-6-methoxytetrahydro-2H-pyran-2-yl)methanol (1.2 g, 1.67 mmol) in DCM (5 mL) was added. The reaction mixture was stirred at −70° C. for 1 hour, then triethylamine (843 mg, 8.35 mmol) was added dropwise. The reaction mixture was stirred at room temperature for 30 minutes, then 1M hydrochloric acid was added in an ice-water bath. The mixture was extracted with DCM, the organic phase was washed twice with saturated brine, then dried over anhydrous sodium sulfate and concentrated to give a white foamy solid (1.2 g, yield: 100%), which was used directly in the next step.

Step 12: ((3S,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2,2-diyl)dimethanol (2S,3S,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2-carbaldehyde (1.2 g, 1.67 mmol) was dissolved in 1,4-dioxane (15 mL), then paraformaldehyde solution (230 mg, 7.68 mmol) and potassium hydroxide (393 mg, 7.01 mmol)) were added under N$_2$. The reaction mixture was heated to 50° C. for 2 hours. The reaction solution was left to stand and filtered, then the filtrate was concentrated below 50° C. The resulting residue was dissolved in dichloromethane (50 mL), and washed with saturated brine (50 mL×2), then dried over anhydrous sodium sulfate and filtered, the filtrate was concentrated. The resulting residue was purified by column chromatography (eluent PE:EA=5:1~3:1) to give the title product ((3S,4S,5R)-3,4,5-tris(benzyloxy)-6-(3 ((2,3-dihydrobenzo[b][1,4]dioxin-6-yl)methyl)-4-ethylphenyl)-6-methoxytetrahydro-2H-pyran-2,2-diyl)dimethanol (200 mg, a yellow oil, yield: 16.6%).

Step 13: (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol ((3S,4S,5R)-3,4,5-tris(benzyloxy)-6-(3-((2,3-dihydrobenzo[b][1,4]dioxin-6-yl)methyl)-4-ethylphenyl)-6-methoxytetrahydro-2H-pyran-2,2-diyl)dimethanol (180 mg, 0.24 mmol) was dissolved in a mixed solvent of tetrahydrofuran (5 mL) and methanol (10 mL) (v:v=1:10), then 10% Pd/C (90 mg) was added. The reaction mixture was purged with hydrogen three times and stirred at room temperature for 3 hours, then filtered, and then the filtrate was concentrated under reduced pressure. The resulting residue was purified by column chromatography (CH$_2$Cl$_2$:MeOH=25:1~15:1) to give the title product (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol (80 mg, a white solid, yield: 76%).

MS m/z (ESI): 445.1 [M+1].

$^1$H NMR (400 MHz, MeOD) δ 7.43-7.34 (m, 2H), 7.19 (d, J=7.9 Hz, 1H), 6.70 (d, J=8.2 Hz, 1H), 6.64-6.53 (m, 2H), 4.24-4.13 (m, 5H), 3.93 (s, 2H), 3.84 (dd, J=19.4, 10.2 Hz, 2H), 3.76-3.60 (m, 4H), 2.60 (q, J=7.5 Hz, 2H), 1.10 (t, J=7.6 Hz, 3H).

Activity Assay of SGLT1 and SGLT2:

The following method was used to determine the inhibitory activity of the compounds of the present invention on SGLT1 and SGLT2. The experimental method is summarized as follows:

SGLT1 and SGLT2 transiently transferred HEK293 cells (prepared according to the existing literature "Diabetes, 57, 1723-1729, 2008", wherein cDNA of SGLT1 and SGLT2 was purchased from Origene company) were seeded in a 96-well plate. The density of the cells was 1-1.5×10$^4$. The cells were cultured at 37° C. and 5% CO$_2$ for 48 hours, and then washed twice with 200 μL sodium-free buffer. 90 μL sodium-containing buffer of the test compound at different concentrations was added to the well. Each test compound was repeated in three wells for each concentration. The cells were cultured at 37° C. for 15 minutes, then 10 μL (in number 0.1 μCi [$^{14}$C]) Methyl α-D-glucopyranoside was added to each well of the 96-well plate. The cells were further cultured at 37° C. for 2 hours, then the supernatant was discarded. The cells were washed twice with pre-chilled sodium-free buffer and then dissolved in 100 μL NaOH (200 mM). 100 μL scintillation solution was added, and mixed well. Scintiloscope was used for the quantitative detection of $^{14}$C.

$IC_{50}$ values of the compounds of various examples were calculated from the aggregation rate at different concentrations.

| Example No. | $IC_{50}$ (SGLT2)/nM | $IC_{50}$ (SGLT1)/nM |
|---|---|---|
| 1 | 0.58 | 952.90 |
| 2 | 3.67 | 15.72 |
| 3 | 19.77 | 2559.00 |
| 4 | 132.30 | 89.01 |
| 5 | 4.30 | 301.00 |
| 6 | 2.59 | 99.91 |
| 7 | 1.82 | 17.19 |
| 8 | 583.2 | 1.21 |
| 9 | 1.49 | 16.6 |

CONCLUSION

The compounds of the present invention had significant inhibition effects on SGLT2; some compounds also inhibited SGLT1, especially compounds of Examples 2, 4, 6, 7, and 9.

Finally, it should be noted that the above examples are merely provided for describing the technical solution of the present invention, but are not intended to limit the scope of the present invention. Although the present invention has been described in detail with reference to the preferred examples, the person skilled in the art would understand that modifications or equivalent substitutions of the technical solution of the present invention can be made without departure from the spirit and scope of the present invention, which should be included into the claims of the present invention.

What is claimed is:

1. A compound of formula (I-a3), or a tautomer, enantiomer, diastereomer, or racemate thereof, or a pharmaceutically acceptable salt thereof:

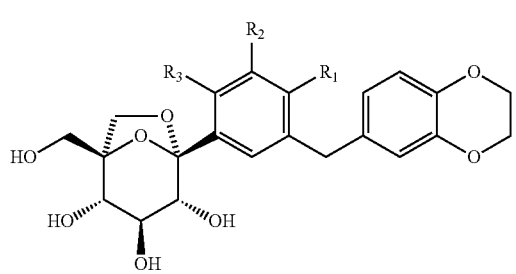

I-a3 wherein:
$R_1$, $R_2$ and $R_3$ are each independently selected from the group consisting of hydrogen, halogen, hydroxy, cyano, nitro, $C_{1-8}$alkyl, $C_{3-8}$cycloalkyl, $C_{1-8}$alkoxy, $C_{3-8}$cycloalkoxy, —S(O)$_p$R$_{11}$, —C(O)R$_{11}$, —C(O)OR$_{11}$, —NR$_{12}$R$_{13}$ and —C(O)NR$_{12}$;

$R_{11}$, $R_{12}$ and $R_{13}$ are each independently selected from the group consisting of hydrogen and $C_{1-4}$ alkyl; and each p is independently 0, 1, or 2.

2. A process for preparing the compound of formula (I-a3) according to claim 1, comprising: condensing a compound of formula (II) with a compound of formula (III) to provide a compound of formula (IV), converting the compound of formula (IV) into a compound of formula (V), and then deprotecting the compound of formula (V) to give the compound of formula (I-a3) as follows:

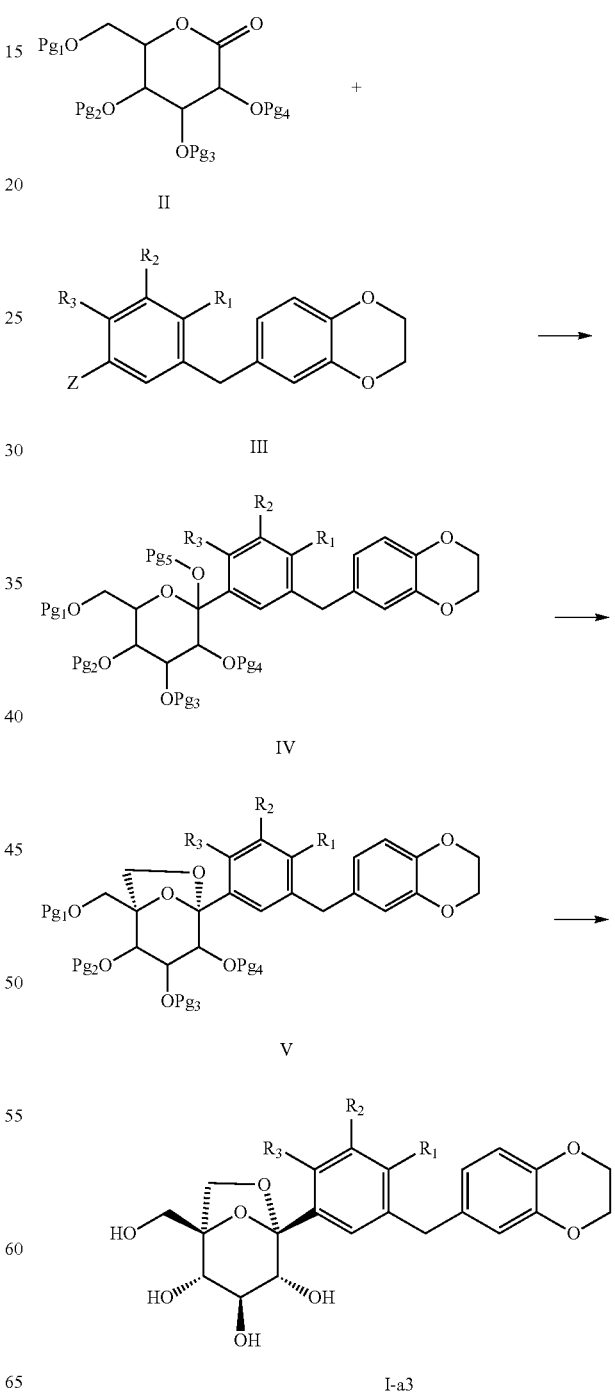

wherein:

Z is halogen, $Pg_1$, $Pg_2$, $Pg_3$ and $Pg_4$ are each independently a hydroxy protecting group that can be the same or different; and $Pg_5$ is selected from the group consisting of hydrogen and hydroxy protecting group.

3. The process according to claim 2, wherein Z is selected from the group consisting of bromine and iodine; $Pg_1$, $Pg_2$, $Pg_3$, and $Pg_4$ are each independently selected from the group consisting of benzyl, trimethylsilyl, and acetyl; and $Pg_5$ is selected from the group consisting of hydrogen and $C_{1-3}$alkyl.

4. A pharmaceutical composition comprising a therapeutically effective amount of the compound, or the tautomer, enantiomer, diastereomer, or racemate thereof, or the pharmaceutically acceptable salt thereof according to claim 1, and a pharmaceutically acceptable carrier.

5. A method of treating diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetic complications, atherosclerosis, or hypertension, comprising a step of administering to a patient in need thereof the pharmaceutical composition according to claim 4.

6. A method of inhibiting a sodium-dependent glucose co-transporter (SGLT) protein, the method comprising administering to the SGLT protein the compound of formula (I), or the tautomer, enantiomer, diastereomer, or racemate thereof, or the pharmaceutically acceptable salt thereof according to claim 1.

7. A compound selected from the group consisting of:

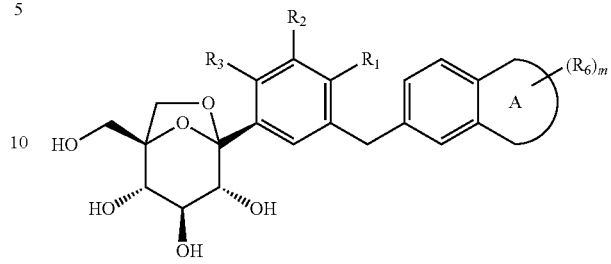

I-a2 or a tautomer, enantiomer, diastereomer, or racemate thereof, or a pharmaceutically acceptable salt thereof.

8. A pharmaceutical composition comprising a therapeutically effective amount of the compound, or the tautomer, enantiomer, diastereomer, or racemate thereof, or the pharmaceutically acceptable salt thereof according to claim 7, and a pharmaceutically acceptable carrier.

9. A method of treating diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetic complications, atherosclerosis, or hypertension, comprising a step of administering to a patient in need thereof the pharmaceutical composition according to claim 8.

10. A method of inhibiting a sodium-dependent glucose co-transporter (SGLT) protein, the method comprising administering to the SGLT protein the compound of formula (I), or the tautomer, enantiomer, diastereomer, or racemate thereof, or the pharmaceutically acceptable salt thereof according to claim 7.

* * * * *